(12) United States Patent
Schentag et al.

(10) Patent No.: US 9,443,060 B2
(45) Date of Patent: *Sep. 13, 2016

(54) METHOD AND SYSTEM TO PROVIDE PERSONALIZED PHARMACEUTICAL COMPOSITIONS AND DOSAGES

(71) Applicant: Volant Holdings GMBH, Feusisberg (CH)

(72) Inventors: Jerome J. Schentag, Buffalo, NY (US); Joseph M. Fayad, Las Vegas, NV (US); Scott V. Monte, West Seneca, NY (US)

(73) Assignee: VOLANT HOLDINGS GMBH, Feusisberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/677,044

(22) Filed: Apr. 2, 2015

(65) Prior Publication Data
US 2015/0235002 A1 Aug. 20, 2015

Related U.S. Application Data

(63) Continuation of application No. 13/754,855, filed on Jan. 30, 2013, now Pat. No. 8,999,721, which is a continuation-in-part of application No. 12/911,497, filed on Oct. 25, 2010, now Pat. No. 8,367,418.

(60) Provisional application No. 61/254,373, filed on Oct. 23, 2009, provisional application No. 62/039,017, filed on Aug. 19, 2014.

(51) Int. Cl.
*G01N 33/66* (2006.01)
*A61K 31/7004* (2006.01)
*A61K 45/06* (2006.01)
*G06F 19/00* (2011.01)

(52) U.S. Cl.
CPC ....... *G06F 19/3431* (2013.01); *A61K 31/7004* (2013.01); *A61K 45/06* (2013.01); *G01N 33/66* (2013.01); *G01N 2800/042* (2013.01); *G01N 2800/52* (2013.01); *Y10T 436/144444* (2015.01)

(58) Field of Classification Search
CPC .................. G01N 2800/042; G01N 2800/52; G01N 33/48; G01N 33/66; Y10T 436/144444; A61K 31/70; A61K 31/7004; A61K 45/06; G06F 19/3431

USPC ....... 436/63, 67, 71, 95, 14, 15; 435/14, 15; 424/9.2, 490, 451; 514/6.8, 6.9, 16.4, 514/23, 1.1, 6.5; 702/19
See application file for complete search history.

(56) References Cited

U.S. PATENT DOCUMENTS

| | | | |
|---|---|---|---|
| 8,367,418 B2 | 2/2013 | Monte et al. | |
| 8,999,721 B2 * | 4/2015 | Schentag et al. | ............... 436/95 |
| 2011/0268795 A1 | 11/2011 | Fayad | |
| 2013/0273154 A1 | 10/2013 | Fayad et al. | |

FOREIGN PATENT DOCUMENTS

| | | |
|---|---|---|
| WO | 2010/027498 A2 | 3/2010 |
| WO | 2014110090 A1 | 7/2014 |
| WO | 2016011335 A1 | 1/2016 |

OTHER PUBLICATIONS

Fayad, J., et al., The FS Index, A Quantitative Means of Describing Progression of Metabolic Syndrome in Patients, The American Journal of Gastroenterology, Oct. 2012, vol. 107, supplement 1, p. S576, abstract No. 1445.
Monte, S.V., et al., Glucose Supply and Insulin Demand Dynamics of Antidiabetic Agents, Journal of Diabetes Science and Technology, Mar. 2010, vol. 4, issue 2, pp. 365-381.
Monte, S.V., et al., Characterization of Cardiovascular Outcomes in a Type 2 Diabetes Glucose Supply and Insulin Demand Model, Journal of Diabetes Science and Technology, Mar. 2010, vol. 4, issue 2, pp. 382-390.
Monte SV, et al. Glucose Supplnd Insulin Demand Dynamics of Antidiabetic Agents. Journal of Diabetes Science and Technology, 2010;4(2):365-381.
Monte SV, et al. Characterization of Cardiovascular Outcomes in a Type 2 Diabetes Glucose Supply and Insulin Demand Model. Journal of Diabetes Science and Technology, 2010;4(2):382-390.

* cited by examiner

*Primary Examiner* — Maureen Wallenhorst
(74) *Attorney, Agent, or Firm* — Henry D. Coleman; R. Neil Sudol

(57) ABSTRACT

Provided is a method for assessing cardiovascular risk in Metabolic Syndrome and Type 2 Diabetes patients. The method involves obtaining data from a Type 2 diabetes patient or a Metabolic Syndrome patient and determining a Fayad/Schentag index which includes a Glucose Supply Index (S) to an Insulin Demand Index (D) ratio. The Fayad/Schentag index is used in scoring cardiovascular risks of Metabolic Syndrome patients and for recommending and implementing therapeutic interventions that can be shown to lower cardiovascular risk.

10 Claims, 17 Drawing Sheets

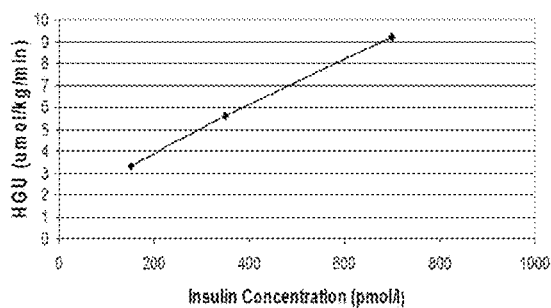
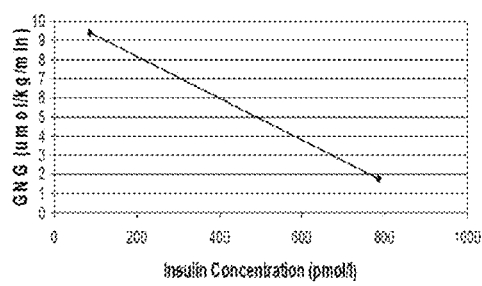
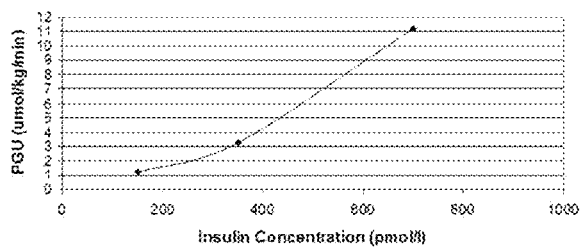
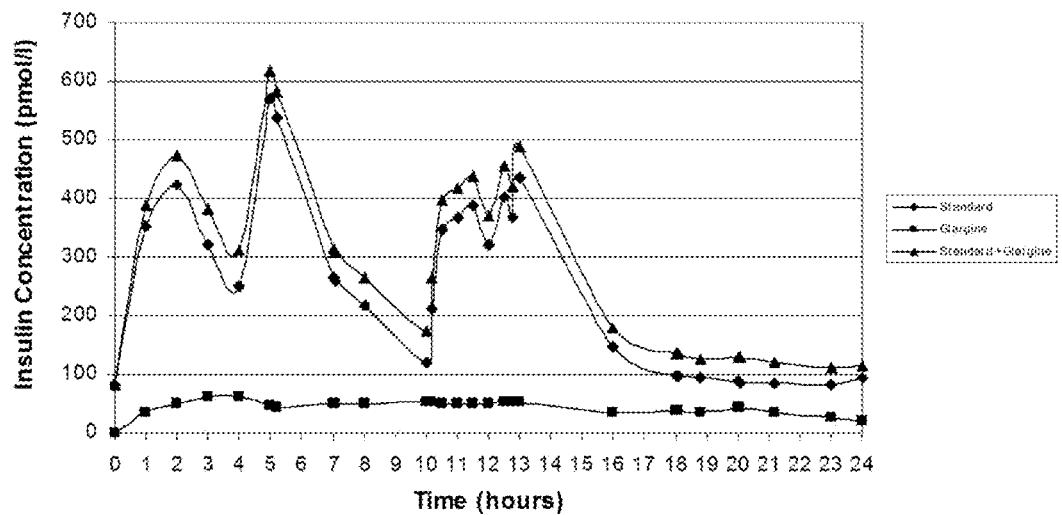
Figure 4

Lookup Table

| Parameter | 0 | 1 | 2 | 3 | 4 |
|---|---|---|---|---|---|
| Age (years) | <40 | ≥40 to <55 | 55 to <65 | 65 to <75 | ≥75 |
| Gender | Female | Male | - | - | - |
| Duration of T2D (years) | 0 to <2 | 2 to <5 | 5 to <10 | 10 to <15 | ≥15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease ≥1 artery | PCI or CABG of ≥1 artery | MI, Ischemic Stroke |
| Body Mass Index (kg/m²) | <25 | 25 to <30 | 30 to <35 | 35 to <40 | ≥40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A1C (%) | <6 | 6 to <7 | 7 to <7.5 | 7.5 to <8 | ≥8 |
| Supply/Demand Ratio | ≥2 | 1.25 to <2 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | >160 |
| HDL-Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |
| Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention ||||||

Figure 6

Baseline Scoring for Patient AB:

| Parameter | 0 | 1 | 2 | 3 | 4 |
|---|---|---|---|---|---|
| Age (years) | <40 | 40 to <55 | 55 to <65 | 65 to <75 | >75 |
| Gender | Female | Male | -- | -- | -- |
| Duration of T2D (years) | 0 to <2 | 2 to <5 | 5 to <10 | 10 to <15 | >15 |
| Smoking History | Never | Quit >5 years ago | Quit 0 to <5 yrs ago | Current, <1 PPD | Current ≥1 PPD |
| Vascular Disease Status | None | Peripheral Arterial Obstructive Disease | Coronary Artery Stenosis of 1 artery | PCI or CABG of >1 artery | MI, Ischemic Stroke |
| Body Mass Index (kg/m²) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 89 | SBP: 140 to 149 -OR- DBP: 85 to 89 | SBP: 150 to 159 -OR- DBP: 90 to 99 | SBP: ≥160 -OR- DBP: ≥100 |
| Hemoglobin A1C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | -- | Intermediate Fat, Intermediate Carb | -- | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | ≥160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEI/ARB, Antiplatelet, Beta-blocker, Statin) | 4/4 | 3/4 | 2/4 | 1/4 | 0/4 |
| Abbreviations: ACEI = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention ||||||

Total Points = 24

| Parameter | 0 | 1 | 2 | 3 | 4 |
|---|---|---|---|---|---|
| Age (years) | <40 | 40 to <55 | 55 to <65 | 65 to <75 | >75 |
| Gender | Female | Male | - | - | - |
| Duration of T2D (years) | 0 to <2 | 2 to <5 | 5 to <10 | 10 to <15 | >15 |
| Smoking History | Never | Quit ≥5 years ago | Quit 0 to <5 yrs ago | Current, <1 PPD | Current ≥1 PPD |
| Vascular Disease Status | None | Peripheral Arterial Obstructive Disease | Coronary Artery Disease ≥1 artery | PCI or CABG of >1 artery | MI, Ischemic Stroke |
| Body Mass Index (kg/m²) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A1C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | >90 to 150 min/wk moderate aerobic | >60 to 90 min/wk moderate aerobic | 30 to 60 min/wk moderate aerobic | Sedentary (<30 minutes/wk) |
| LDL-Cholesterol | <70 | 70 to 99 | 100 to 129 | 130 to 159 | ≥160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEi/ARB, Antiplatelet, Beta-blocker, Statin) | 4/4 | 3/4 | 2/4 | 1/4 | 0/4 |

Abbreviations: ACEi = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention Total Points = 22

Figure 9

Management Scenario 3: Roux-en-Y Gastric Bypass

| Parameters | 0 | 1 | 2 | 3 | 4 |
|---|---|---|---|---|---|
| Age (years) | <45 | 45 to <55 | 55 to <65 | 65 to <75 | >75 |
| Gender | Female | Male | - | - | - |
| Duration of T2D (years) | 0 to <2 | 2 to <5 | 5 to <10 | 10 to <15 | >15 |
| Smoking History | Never | Quit ≥5 years ago | Quit 0 to <5 yrs ago | Current, <1 PPD | Current, ≥1 PPD |
| Vascular Disease Status | None | Peripheral Arterial Obstructive Disease | Coronary Artery Disease ≥1 artery | PCI or CABG of ≥1 artery | MI, Ischemic Stroke |
| Body Mass Index (kg/m²) | <25 | 25 to <30 | 30 to <35 | 35 to <40 | >40 |
| Blood Pressure (mmHg) | SBP: <120 -AND- DBP: <80 | SBP: 120 to 139 -OR- DBP: 80 to 84 | SBP: 140 to 149 -OR- DBP: 85 to 89 | SBP: 150 to 159 -OR- DBP: 90 to 99 | SBP: ≥160 -OR- DBP: ≥100 |
| Hemoglobin A₁C (%) | <6 | 6 to <7 | 7 to <7.5 | 7.5 to <8 | >8 |
| Supply/Demand Ratio | ≥3 | 1.25 to <3 | 1 to <1.25 | 0.75 to <1 | <0.75 |
| Patient Reported Hypoglycemia | None | Infrequent w/o objective evidence | Infrequent w/ objective evidence | Frequent w/o objective evidence | Frequent w/ objective evidence |
| Practitioner Evaluated Dietary Habits | Low Fat, Low Carb | - | Intermediate Fat, Intermediate Carb | - | High Fat, High Carb |
| Practitioner Evaluated Physical Activity Habits | ≥150 min/wk moderate aerobic | 90 to 150 min/wk moderate aerobic | 60 to 90 min/wk moderate aerobic | 30 to 60 min/wk moderate aerobic | Sedentary (<30 minutes/wk) |
| LDL Cholesterol | <70 | 70 to 99 | 100 to 129 | 130 to 159 | ≥160 |
| HDL Cholesterol | ≥50 | 45 to 49 | 40 to 44 | 35 to 39 | <35 |
| Triglycerides | <150 | 150 to 249 | 250 to 399 | 400 to 999 | ≥1000 |
| Appropriate Utilization of Concomitant Cardiovascular Therapy (ACEi/ARB, Antiplatelet, Beta-blocker, Statin) | 4/4 | 3/4 | 2/4 | 1/4 | 0/4 |

Abbreviations: ACEi = Angiotensin Converting Enzyme Inhibitor, ARB = Angiotensin Receptor Blocker, CABG = Coronary Artery Bypass Graft, HDL = High Density Lipoprotein, LDL = Low Density Lipoprotein, MI = Myocardial Infarction, PCI = Percutaneous Intervention Total Points = 15

Figure 10

METHOD AND SYSTEM TO PROVIDE PERSONALIZED PHARMACEUTICAL COMPOSITIONS AND DOSAGES

CROSS-REFERENCE TO RELATED APPLICATIONS

This application is a continuation of U.S. patent application Ser. No. 13/754,855, filed Jan. 20, 2013, now U.S. Pat. No. 8,999,721, which is a continuation in part of U.S. patent application Ser. No. 12/911,497, filed on Oct. 25, 2010, now U.S. Pat. No. 8,367,418, issued Feb. 5, 2013, which claims priority to U.S. Provisional application No. 61/254,373, filed on Oct. 23, 2009. This application also claims the benefit of priority of U.S. provisional application No. 62/039,017, filed Aug. 19, 2014. The disclosures of each of the above patent applications are incorporated by reference in their entirety herein.

FIELD OF THE INVENTION

The present invention in one aspect relates to management of Type 2 diabetes and in another aspect relates to management of Metabolic syndrome. In particular embodiments, the invention relates to modulating drug therapies to improve cardiovascular outcomes for Type 2 diabetics and/or for individuals who have or are at risk for developing Metabolic syndrome.

BACKGROUND OF THE INVENTION

The most prevalent form of diabetes is Type 2 diabetes. Type 2 diabetes accounts for approximately 90-95% of all diagnosed cases of diabetes. Type 2 diabetes was previously known as non-insulin-dependent diabetes mellitus (NIDDM). Type 2 diabetes was also previously known as adult-onset diabetes. However, this form of diabetes is becoming increasingly prevalent in the growing population of overweight and clinically obese children and adults. Type 2 diabetes typically begins with insulin resistance, a disorder in which the body's cells do not respond to insulin properly, followed by a gradual loss on part of the pancreas to produce and secrete insulin in at least some patients. Type 2 diabetes is associated with a variety of factors including older age, obesity, family history of diabetes, history of gestational diabetes, impaired glucose metabolism, dietary intake of carbohydrates and glucose, low physical inactivity, and various races or ethnicities. Further conditions considered consequences of diabetes itself include hypertension and cardiovascular disease, especially atherosclerosis and vascular clotting and inflammation that may lead to ischemia of the heart tissues.

According to the American Diabetes Association, 20.6% of adults over the age of 60 have diabetes and 34.8% of all adults have either diabetes or pre-diabetes. A major goal of therapeutic treatment of diabetic patients is to delay or prevent the complications associated with chronic hyperglycemia. Cardiovascular complications are the most frequent cause of morbidity and mortality in diabetic patients. These complications include microangiopathy, retinopathy, neuropathy, nephropathy, and macroangiopathy, which is an accelerated form of atherosclerosis. Most patients with Type 2 diabetes die from cardiovascular disease, and it has only recently been demonstrated that some diabetes medicaments accelerate the development of cardiovascular disease in Type 2 diabetics, while others may prevent or slow down the rate of injury.

Another condition that is widely prevalent and which has multiple relationships and causal connections with cardiovascular disease is Metabolic Syndrome (MS). MS has many different manifestations such as Type 2 Diabetes, hyperlipidemia, obesity and Non-alcoholic fatty liver disease (NAFLD), but heretofore there has been no means of tracking progression of MS in patient populations that may have any or all of these conditions to varying degrees. Thus, there is an ongoing need for improved cardiovascular risk scoring processes for metabolic syndrome manifestation diseases, as well as for Type 2 diabetes. The present invention meets these and other needs.

SUMMARY OF THE INVENTION

The present invention comprises two main, related aspects. These in general relate to assessing, scoring, treating, monitoring treatment, adjustments and changes in drug therapy, and pharmaceutical preparations used for disorders which have in common with one another various effects on, and relationships with, the cardiovascular system. The first main aspect relates to Type 2 diabetes and the second main aspect relates to MS. Those skilled in the art will recognize that characterizing the invention by way of the term "aspects" is not intended to mean that these disorders are mutually exclusive. To the contrary, they have multiple relationships with each other and certain overlapping etiologies, conditions, signs and symptoms as will be more fully described herein.

In the first aspect, the invention provides a method for determining a suitable drug combination for the treatment of Type 2 diabetes by obtaining data from a Type 2 diabetes population in which all of the Type 2 diabetics are not taking any Type-2 diabetes drugs and obtaining reference levels of glucose supply parameters that include: carbohydrate exposure (CE), hepatic glucose uptake (HGU), hepatic gluconeogenesis (GNG) and insulin resistance (IR). From the data the following insulin demand parameters are also determined: peripheral glucose uptake (PGU) and peripheral insulin exposure (PIE). Data from discrete samples of Type-2 diabetes populations in which all individuals are being treated with one or more Type 2 diabetes drugs at a therapeutic dose are also obtained, and the effects of the drugs on the glucose supply and insulin demand parameters are used to determine adjustment factors which represent the effect of each of the drugs at the therapeutic dosage. The adjustment factors are used to determine a Glucose Supply Index (S) for each drug calculated as follows:

1+CE+HGU+GNG+IR, and an Insulin Demand Index (D) calculated as follows:

1+PGU+PIE.

The Glucose Supply Index and the Insulin Demand Index form a ratio which is indicative of the relationship between the effect on the glucose supply and on the insulin demand parameters for the drugs, and it is considered that an SD ratio of above 1.0 is indicative that the drug or drug combination for which the SD ratio is calculated functions on the glucose supply side of Type 2 diabetes management, while an SD ratio of below 1.0 is indicative that the drug or drug combination for which the SD ratio is calculated functions on the insulin demand supply side of Type 2 diabetes management.

In another embodiment, the invention also provides a method for determining modulation of cardiovascular risk for a Type 2 diabetic who is being treated with at least one drug. This embodiment comprises a) obtaining one or more physiological parameters from the Type 2 diabetic at a first time point and determining the SD ratio for the drug with that is being used to treat the Type 2 diabetic and b) assigning a first cardiovascular risk score for the individual by summing values for one or more physiological parameters that are presented in a Look-Up table. The Look-Up table is provided in FIG. 6. The SD ratio is also used to assign the first cardiovascular risk score. Steps a) and b) are repeated after a period of time, after which a second cardiovascular risk score is obtained. A lower second cardiovascular risk score compared to the first cardiovascular risk score is considered to be indicative of a reduced risk of cardiovascular disease, while a higher second cardiovascular risk score compared to the first cardiovascular risk score is considered to be indicative of an increased risk of cardiovascular disease.

If a higher second cardiovascular risk score is obtained, the invention provides for i) adjusting the dosage of the drug(s), or ii) prescribing and/or administering an additional drug(s) for; or iii) performing a surgical intervention, such as bariatric surgery.

In a second aspect, the invention provides compositions and tools for assessment, therapy, monitoring and treatment of MS. Those skilled in the art will recognize, given the benefit of the present disclosure, that the tools for addressing Type 2 diabetes and MS as disclosed herein have similarities in that they both encompass personalized scoring systems which have in common determining all of or portions the SD ratio. In connection with this, the invention provides for determination and use of the SD ratio in an index, termed herein the "FS index" (for Fayad/Schentag index). In particular, the invention provides compositions and methods of treatment for patients with MS and reducing the cardiovascular risk thereof, wherein patient specific calculations of SD ratio and FS index as further described below enable application of treatments which improve or resolve metabolic syndrome and lower associated cardiovascular risk, and also identify drug therapy beneficial to the resolution or control of metabolic syndrome, as defined by FS index measurements.

In one embodiment, the FS index is calculated and used in a method for determining cardiovascular risk for an individual suspected of having, at risk for, or diagnosed with MS. The method comprises some or all of the following steps:

a) obtaining from an individual one or more biological parameters, and from the biological parameters:

b) determining the FS index, wherein the FS index is calculated as:

$$\frac{0.11\left((FBG+TG)+HBA1c\times\dfrac{HBA1c\times 20}{5}+BMI\times\dfrac{FBG+TG}{150}+AST\times\dfrac{TG\times 4}{100}+FB\text{ insulin}\times(BMI-22)\right)}{S/D\text{ ratio}}$$

wherein the FBG is Fasting Blood Glucose in mg/dl; the TG is Triglycerides in mg/dl; the HBA1c is hemoglobin A1c in %; the BMI is body mass index in kg/m$^2$; AST is Aspartate Transferase in IU/liter; FB insulin is fasting Blood insulin concentration in nmol/liter.

The SD ratio, as explained above, is a ratio of Glucose Supply Index (S) to Insulin Demand Index (D) calculated as follows:

1+[aggregate of carbohydrate exposure (CE)+hepatic glucose uptake (HGU)+hepatic gluconeogenesis (GNG) and +insulin resistance (IR)], and (D) calculated as follows:

1+[aggregate of peripheral glucose uptake (PGU)+ peripheral insulin exposure (PIE)].

The FS ratio results in a numerical value that is assigned to the individual. An FS index value of greater than 60 is indicative that the individual is in need of therapy for MS or at risk for at least one cardiovascular complication associated with MS. Upon determining an FS index value of greater than 60, the invention further comprises administering a drug to the individual. It is preferable that the drug be pH-encapsulated glucose, wherein the glucose is released in the intestine at jejunum or ileum wherein the conditions for release of pH encapsulated glucose are a pH reading at or above a pH of 7.0. pH encapsulated glucose meeting these functional criteria is also referred to herein from time to time as BRAKE, or Brake. In one embodiment, the pH encapsulated glucose delivered in this manner so as to provide an SD value of 3.5 (in contrast to an individual who is not undergoing any drug therapy, wherein the SD value is assigned as "1.0"). In another embodiment, the individual is treated with bariatric surgery, which provides an SD value of 4.0. The SD values of 3.5 for Brake and 4.0 for bariatric surgery were defined from experiments conducted on patients with metabolic syndrome as disclosed herein. The SD values for the diabetes drugs are derived from the data of patients treated and used to develop the lookup table disclosed herein. Values for SD and FS are predictive of cardiovascular risk in metabolic syndrome patients.

In additional embodiments, combinations of pH encapsulated glucose can be used alone or in combination with additional anti-diabetes and/or anti-MS drugs. Combining such agents result in a higher SD ratio, which in turn results in a lowering of the FS index, which is favorable to the patient in need of lower cardiovascular risk. In certain embodiments, drug combinations have an additive, or greater than additive effect on the SD value. In certain embodiments, pH encapsulated glucose is beneficially additive on SD when combined with either Metformin or Sitagliptin, or with any member of the class of DPP-IV inhibitors in said combinations thereof. Additional agents that can be used in drug combinations include but are not necessarily limited to statin drugs, Insulins, hormones, GLP-1 drugs, lipids, proteins, amino-acids, and other sugars or carbohydrates, and combinations thereof.

The invention includes applications for individuals who have been diagnosed with MS, and who are being treated for MS with at least one drug which may be intended for therapy of MS or any of its individual manifestations. For such patients, a first FS index value can be obtained and the patient can continue treatment with the drug for a period of time, after which (or during) a second FS index value is determined by repeating the steps used for determination of the first FS index value. A lower second FS value relative to the first FS index value indicates the drug is effective for treating individual's MS. However, a higher second FS value relative to the first FS index value indicates that the individual is in need of a change in dosing of the first drug, or a change to a different drug, or is a candidate for bariatric surgery.

BRIEF DESCRIPTION OF THE DRAWINGS

FIG. 3A is a graphical representation of HGU insulin-dose response relationship. FIG. 3B is a graphical representation of PGU insulin-dose response relationship. FIG. 3C is a graphical representation of GNG insulin-dose response relationship.

FIG. 4 is a graphical representation of standard+insulin glargine concentration time profile (T2D).

FIG. 6 is the Look-Up table.

FIG. 7 provides baseline risk scoring for illustrative patient AB.

FIG. 8 provides risk scoring for illustrative patient AB under insulin glargine therapy.

FIG. 9 provides risk scoring for illustrative patient AB under metformin therapy.

FIG. 10 provides risk scoring for illustrative patient AB as if Roux-en Y gastric bypass surgery had been performed.

DETAILED DESCRIPTION OF THE INVENTION

Figure 1:
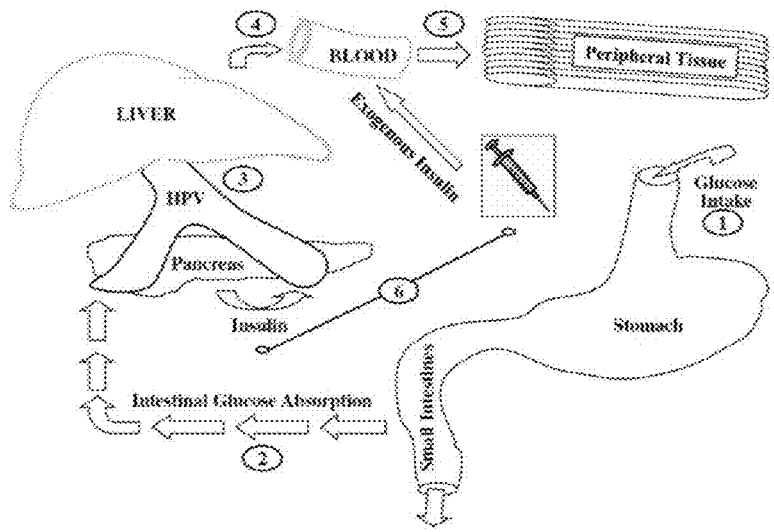
FIG. 1 is a pictorial representation of the glucose supply and insulin demand model set forth in the instant invention.

Traditional treatments of Type 2 diabetes either increase the release of insulin from the pancreas, attempt to sensitize the peripheral cells to insulin, or give additional insulin to drive more glucose into cells. We term these treatments insulin demand methods. Based on the underlying mechanisms at work in Type 2 diabetes, the insulin demand methods are less than optimal, and are likely at least partly responsible for increased cardiovascular injury in Type 2 diabetics, since cardiovascular injury is associated with abnormal increases in glucose inside the endothelial cells lining blood vessels, and the insulin demand methods all operate by increasing the glucose inside endothelial cells. In this regard, the common theme of the historical and contemporary cardiovascular outcome trials in Type 2 diabetics has been a focus on the intensive reduction of the primary biomarker, HbA1C, which is a measure of glucose in red blood cells. The American Diabetes Association (ADA)/European Association for the Study of Diabetes (EASD) consensus algorithm has been a guiding tool for the reduction of HbA1C. This algorithm advocates the initial use of metformin with subsequent addition and intensification of sulfonylurea and/or insulin therapies. Inherent to this pharmacotherapeutic approach, as well as those utilized prior to the guidelines, is an imbalance toward increased insulin exposure and increased peripheral glucose disposal, but these methods for lowering glycemia have adverse long term effects on the cardiovascular complications of diabetes patients. Thus, according to the present invention, more desirable methods for control of glycemia involve lowering the supply of glucose to endovascular cells and lowering systemic inflammation, which we term the glucose supply side of diabetes management. This methodology focuses treatments for Type 2 diabetes on the gastrointestinal tract and the liver, and moves the treatment approach away from more insulin given to Type 2 diabetics, who typically already produce excess insulin. The present invention accordingly facilitates analysis of relationships between the effect on glucose supply and insulin demand for Type 2 diabetes drugs, and furthermore provides methods for determining and modulating cardiovascular risk for Type 2 diabetics so that adjustments and/or changes in drug regimens, and/or surgical interventions can be recommended to improve cardiovascular risk by managing diabetes on the glucose supply side.

With respect to MS, and as disclosed in U.S. provisional application No. 61/254,373, filed Oct. 23, 2009 ("the '373 application"), to which the present application claims priority and the disclosure of which is incorporated herein by reference, it has become increasingly common in the United States, and at the time of filing the '373 application, it was estimated that about 20-25 percent of U.S. adults were affected with MS. MS is characterized by a group of metabolic risk factors in one person which include but are not necessarily limited to (a) central obesity, indicated by excessive fat tissue in and around the abdomen; (b) atherogenic dyslipidemia, indicated by blood fat disorders, mainly high triglycerides and low HDL cholesterol, that foster plaque buildups in artery walls; (c) elevated blood pressure (130/85 mmHg or higher); (d) insulin resistance or glucose intolerance; and (e) pro-inflammatory state (e.g., elevated C-reactive protein in the blood). The syndrome is closely associated with a generalized metabolic disorder called insulin resistance, in which the body cannot use insulin efficiently. Metabolic syndrome is also called insulin resistance syndrome, which can lead to Type 2 diabetes, which is diagnosed when hyperglycemia is present for sufficient time to elevate blood hemoglobin A1c fraction. As also disclosed in the '373 application, a goal of the Glucose Supply Side system is to lower the risk of cardiovascular complications associated with the treatment of diabetes in individuals, but also includes prevention or treatment of cardiovascular, cardiopulmonary, pulmonary or renal diseases in both individuals and in the population by improving endothelial function and achieving protection of organs, tissues and blood vessels in indications in which control of blood pressure and lipid levels are necessary, and for the treatment of Metabolic Syndrome and insulin resistance in patients. As will be evident from the following description and examples, the present invention includes use of the SD ratio for assessing, monitoring, and developing and/or implementing MS therapies by way of its use in the FS index.

In one embodiment, the invention provides a method for determining a suitable drug combination for the treatment of Type 2 diabetes that is able to decrease cardiovascular risk. The method comprises obtaining data from a Type 2 diabetes population, which in one embodiment in a Type 2 diabetes population in which all of the Type 2 diabetics are taking Type-2 diabetes drugs. The data are used to obtain reference levels of the following glucose supply parameters: carbohydrate exposure (CE), hepatic glucose uptake (HGU), hepatic gluconeogenesis (GNG) and insulin resistance (IR). The data are also used to obtain reference levels of the following insulin demand parameters: peripheral glucose uptake (PGU) and peripheral insulin exposure (PIE). The method further entails obtaining data from discrete samples of Type-2 diabetes populations in which all individuals are being treated with one or more Type 2 diabetes drugs at a therapeutic dose. The effects of the drugs on the glucose supply and insulin demand parameters are used to determine adjustment factors which represent the effect of each of the drugs at the therapeutic dosage. Adjustment factors for representative Type 2 diabetes drugs are presented in Table 1. The adjustment factors for each of the drugs on each of the glucose supply and insulin demand parameters are then used to determine a Glucose Supply Index (S) for each drug calculated as follows:

1+CE+HGU+GNG+IR, and an Insulin Demand Index (D) calculated as follows:

1+PGU+PIE.

The Glucose Supply Index and the Insulin Demand Index form a ratio (the SD ratio) which is indicative of the relationship between the effect on the glucose supply and on the insulin demand parameters for the one or more drugs. SD ratios for representative Type 2 diabetes drugs are presented in Table 1. Without intending to be bound by any particular theory, it is considered that an SD ratio of above 1.0 is indicative that the drug or drug combination for which the SD ratio is calculated functions on the glucose supply side of Type 2 diabetes management, and is therefore beneficial to the cardiovascular system for an individual receiving the drug or drug combination. It is also considered that an SD ratio of below 1.0 is indicative that the drug or drug combination for which the SD ratio is calculated functions on the insulin demand supply side of Type 2 diabetes management, and is therefore not as beneficial for an individual receiving the drug or drug combination as compared to a drug that affects the glucose supply side. Adjustment factors for pH encapsulated glucose and for Roux-en-Y gastric bypass bariatric surgery are also shown in Table 1. It will be recognized by those in the art that the present invention is not necessarily limited to determining suitable combinations of drugs because the invention could also be used for analysis of SD ratios for single drugs.

TABLE 1

| Antidiabetic | CE inhibition | HGU uptake | GNG inhibition | IR reduction | PIE | PGU | Therapeutic Dose | SD Radio |
|---|---|---|---|---|---|---|---|---|
| Roux-en-Y gastric bypass | 0.75 | 0.85 | 0.75 | 0.45 | −0.35 | 0.15 | N/A | 4.75 |
| pH encapsulated glucose | 0.45 | 0.75 | 0.45 | 0.20 | −0.15 | 0.5 | N/A | 2.85 |
| Miglitol | 0.30 | 0.15 | 0.05 | 0.15 | 0.05 | 0.25 | 300 mg | 1.25 |
| Acarbose | 0.30 | 0.15 | 0.05 | 0.15 | 0.05 | 0.25 | 300 mg | 1.25 |
| Metformin | 0.15 | 0.40 | 0.35 | 0.38 | −0.10 | 0.14 | 2000 mg | 2.20 |
| Acetohexamide | 0.00 | 0.14 | 0.07 | 0.00 | 0.21 | 0.36 | 1500 mg | 0.77 |
| Chlorpropamide | 0.00 | 0.14 | 0.07 | 0.00 | 0.21 | 0.36 | 500 mg | 0.77 |
| Tolazamide | 0.00 | 0.14 | 0.07 | 0.00 | 0.21 | 0.36 | 1000 mg | 0.77 |
| Tolbutamide | 0.00 | 0.14 | 0.07 | 0.00 | 0.21 | 0.36 | 2000 mg | 0.77 |
| Glimepiride | 0.00 | 0.18 | 0.08 | 0.00 | 0.24 | 0.39 | 8 mg | 0.77 |
| Glipizide | 0.00 | 0.18 | 0.08 | 0.00 | 0.24 | 0.39 | 10 mg | 0.77 |
| Glyburide | 0.00 | 0.14 | 0.07 | 0.00 | 0.21 | 0.36 | 10 mg | 0.77 |
| Nateglinide | 0.00 | 0.21 | 0.11 | 0.00 | 0.34 | 0.60 | 360 mg | 0.69 |
| Repaglinide | 0.00 | 0.16 | 0.07 | 0.00 | 0.20 | 0.31 | 12 mg | 0.81 |
| Pioglitazone | 0.00 | 0.40 | 0.21 | 0.35 | −0.10 | 0.59 | 45 mg | 1.32 |
| Rosiglitazone | 0.00 | 0.40 | 0.23 | 0.39 | −0.10 | 0.70 | 8 mg | 1.27 |
| Troglitazone | 0.00 | 0.40 | 0.22 | 0.35 | −0.10 | 0.67 | 600 mg | 1.25 |
| Insulin Aspart | 0.00 | 0.23 | 0.14 | 0.00 | 0.42 | 0.80 | 0.5 U/kg | 0.62 |
| Insulin Lispro | 0.00 | 0.23 | 0.14 | 0.00 | 0.42 | 0.80 | 0.5 U/kg | 0.62 |
| Insulin Regular | 0.00 | 0.21 | 0.11 | 0.00 | 0.33 | 0.64 | 0.5 U/kg | 0.67 |
| Insulin Isophane | 0.00 | 0.23 | 0.10 | 0.00 | 0.28 | 0.40 | 0.5 U/kg | 0.79 |
| Insulin Aspart Protamine | 0.00 | 0.23 | 0.10 | 0.00 | 0.28 | 0.40 | 0.5 U/kg | 0.79 |
| Insulin Lispro Protamine | 0.00 | 0.23 | 0.10 | 0.00 | 0.28 | 0.40 | 0.5 U/kg | 0.79 |
| Insulin Lente | 0.00 | 0.23 | 0.10 | 0.00 | 0.28 | 0.40 | 0.5 U/kg | 0.79 |
| Insulin Ultralente | 0.00 | 0.17 | 0.08 | 0.00 | 0.24 | 0.38 | 0.5 U/kg | 0.77 |
| Insulin Glargine | 0.00 | 0.24 | 0.10 | 0.00 | 0.30 | 0.42 | 0.5 U/kg | 0.78 |

In Table 1, under the column "CE inhibition" the adjustment factors represent decreases in carbohydrate exposure caused by the designated drug; under the column "HGU uptake" the adjustment factors represent increases in hepatic glucose uptake; under the "GNG inhibition" the adjustment factors represent decreases in hepatic gluconeogenesis; under the column "IR reduction" the adjustment factors represent decreases in insulin resistance; under the column "PIE" the adjustment factors represent increases in peripheral insulin exposure; and under the column "PGU" the adjustment factors represent increases in peripheral glucose uptake.

In certain embodiments, an SD ratio of greater than 1.1, 1.2, 1.25, 1.3, 1.35, 1.4, 1.45 or 1.5, including all integers to the second decimal place there between, or higher, is indicative that the drug or drug combination for which the SD ratio is calculated functions on the glucose supply side of Type 2 diabetes management, and is therefore beneficial for an individual receiving the drug or drug combination producing these values of the SD ratio.

In another embodiment, the invention provides a method for determining modulation of cardiovascular risk for a Type 2 diabetic who is being treated with at least one drug. The method comprises a) obtaining one or more physiological parameters from the Type 2 diabetic at a first time point and determining the SD ratio for the at least one drug with which the Type 2 diabetic is being treated, and b) assigning a first cardiovascular risk score for the individual by summing values for one or more physiological parameters in the Look-Up table provided in FIG. 6 and the SD ratio. Then steps a) and b) are repeated after a period of time, and from the Look-Up table a second cardiovascular risk score is obtained. A lower second cardiovascular risk score compared to the first cardiovascular risk score is considered to be indicative of a reduced risk of cardiovascular disease. A higher second cardiovascular risk score compared to the first cardiovascular risk score is considered to be indicative of an increased risk of cardiovascular disease.

If a higher second cardiovascular risk score is obtained, the invention provides for the following options: i) adjust the dosage of the drug(s) with which the Type 2 diabetic is being treated, or ii) prescribe and/or administer an additional drug(s) for the Type 2 diabetic; or iii) perform a surgical intervention, such as bariatric surgery, such as Roux-en-Y gastric bypass surgery.

The invention further comprises managing the Type 2 diabetic on the glucose supply side by prescribing and/or administering a composition comprising DPP-IV inhibitors or agents that function in a manner similar to DPP-IV inhibitors. The invention may further comprise administering to the Type 2 diabetic a composition comprising an agent that mimics gastric bypass surgery on the ileum. In one embodiment, an agent capable of mimicking the effects of gastric bypass surgery is a composition comprising pH encapsulated glucose, which formulated so as to be released at a pH of approximately 6.5 to 7.5, i.e., the pH environment of the ileum. Compositions comprising pH encapsulated glucose, as well as other encapsulated agents suitable for use in the invention are described in US Patent Publication No. 20110268795; U.S. Pat. Nos. 5,322,697, 5,753,253, and 6,267,988, the disclosures of each of which are incorporated herein by reference. Alternatively, other supply side nutrients/agents can be similarly pH encapsulated glucose so that the agents are released at pH values between 6.5 and 7.5 so as to target the ileum. Non-limiting examples of such agents include metformin, sitagliptin, saxagliptin, linagliptin, probiotic organisms, statins, antibiotics, and GLP-1 mimetics such as exenatide or liraglutide. Further, any combination of agents and/or bariatric surgical procedures may be performed and/or recommended according to the invention.

Type 2 diabetic drugs that can be used for calculating reference, levels, SD ratios, and cardiovascular risk scores include but are not necessary limited to Metformin, Acetohexamide, Chlorpropamide, Tolazamide, Tolbutamide, Glimepiride, Glipizide, Glyburide, Nateglinide, Repaglinide, Pioglitazone, Rosiglitazone, Troglitazone, Insulin, Aspart, Insulin, Lispro, Insulin, Regular, Insulin, Isophane, Insulin, Aspart, Protamine, Insulin, Lispro, Protamine, Insulin, Lente, Insulin, Ultralente, Insulin, Glargine, and combinations, thereof. It will be recognized by those skilled in the art that, given the benefit of the present disclosure, any Type 2 diabetic drug now known or hereinafter developed can be analyzed and used in the method of the invention.

The Look-Up table presented in FIG. 6 provides physiological parameters which can be used in combination with the SD ratio to develop cardiovascular risk scores that are related to a Type 2 diabetic's therapeutic regimen. Those skilled in the art will recognize that additional physiological parameters may be included in the Look-Up table, or physiological parameters may be removed from it, but any such modified Look-Up table that includes an SD ratio will still be useful for developing cardiovascular risk scores without departing from the scope of the instant invention. In one embodiment, the Look-Up table includes at least the SD ratio and the Hemoglobin $A_1C$ level (also referred to as HbA1c level). Further, those skilled in the art will recognize that the risk scoring parameters (i.e., the 0, 1, 2, 3, and 4 values assigned to increasing severity of risk for each risk scoring parameter) are exemplary and can be modified, adjusted and/or replaced with any other alphanumeric characters or symbols, and in turn the summation of the risk scoring parameters can be designated in various ways that are intended to be encompassed within the invention.

It will also be recognized that any method for determining the physiological parameters, which are also considered to be biomarkers, can be used. For example, in one embodiment, a xerogel sensor can be used for biomarker measurement. Suitable methods of using xerogel sensors for testing, for example the breath blood or body fluids of a Type 2 diabetic are described in U.S. Pat. Nos. 6,241,948 and 6,492,182 and 6,589,438, which are incorporated herein by reference. Determining Type 2 diabetes mellitus biomarkers for use in the invention can include testing of breath biomarkers which include but are not necessarily limited to oxygen, glucose, acetoacetate, betahydroxybutyrate, and other suitable free fatty acids and ketone bodies well known in the art; testing isoprostane and other metabolites of prostaglandins or any other analytes that are considered markers of oxidative stress; Nitrous oxides, methyl nitrous oxide metabolites; cytokines, proteins, incretins, peptides, adiponectin, C-Reactive Protein, procalcitonin, troponin, electrolytes, and other markers of the inflammatory pathways or those of cardiovascular injury.

In various embodiments, the present invention can be carried out using a system, which can include but is not necessarily limited to an input/output (I/O) device coupled to a processor; a communication system coupled to the processor; and/or a medical computer program and system coupled to the processor, the medical system configured to process medical data of a user and generate processed medical information, wherein the medical data includes one or more of anatomical data, diabetes associated biomarkers, test specimen data, biological parameters, health information of the user, wherein the processor is configured to dynamically control operations between the communication system and the medical system. The operations of the communication system may include one or more of a mobile device, wireless communication device, cellular telephone, Internet Protocol (IP) telephone, Wi-Fi telephone, server, personal digital assistant (PDA), tablet device in the manner of an I-pad and portable computer (PC). The communication system is configured to communicate one or more of the medical data and the processed medical information to a remote device located one or more of on the user, in a home, in an office, and at a medical treatment facility, the remote device including one or more of a processor-based device, mobile device, wireless device, server, personal digital assistant (PDA), cellular telephone, wearable device, and portable computer (PC). The system can include an analyzer coupled to xerogel-based substrates for concentration-dependent analyte detection, the analyzer including a xerogel-based sensor coupled to a processor configured to analyze the specimen and generate the processed medical information, wherein analysis of the specimen includes correlating parameters of the specimen with the medical data. The specimen may be a biological sample, which could include any fluid or tissue from a patient, wherein the processed medical information includes one or more of a chemical analysis of the specimen.

A device associated with the system can include a medicament delivery system coupled to the processor, the delivery system including at least one reservoir that contains at least one composition, the delivery system configured to administer at least one composition for use in treating the user, wherein the composition is administered under control of the processor and the processed medical information. The delivery system is configured to automatically or manually administer the composition or medicament.

The following example is given to illustrate the present invention. It should be understood that the invention is not to be limited to the specific conditions or details described in this example.

Example 1

This Example provides a description of various embodiments of the invention that illustrate some of the methods by which data from a Type-2 diabetes population in which all of the individuals are not taking any Type-2 diabetes drugs can be analyzed to obtain reference levels of glucose supply and insulin demand parameters, as well as methods by which discrete samples of Type-2 diabetes populations in which all individuals in each sample are being treated with one Type 2 diabetes drugs at a therapeutic dose can be analyzed to identify adjustment factors for the effect of the dose, and in turn how to calculate and use SD ratios for individual drugs.

Therapeutic targets of the glucose supply (CE, 1+2; HGU, 3; GNG, 4; IR, 5) and insulin demand (PGU, 6; PIE, 7) model are presented in FIG. 1. To identify quantitative differences between antidiabetic agents on CE, HGU, GNG, IR, PGU, and PIE, multidatabase searches (Cochrane Central Register of Controlled Trials and Cochrane Register of Systematic Reviews, Embase, OVID Healthstar, OVID Journals, and PubMed) were conducted cross-referencing title and keywords for all selected antidiabetic therapies and their respective targets.

Alpha-glucosidase, biguanide, and thiazolidinedione (TZD) studies with long-term, pre-post design at maximal therapeutic doses were identified to simulate chronic administration. To maintain consistency with cardiovascular trials and accommodate known influences of hyperglycemia and hyperinsulinemia on the respective targets,[13-16] studies including patients with HbA1c in the range of 6-8% and body mass index (BMI)≥30 kg/m² were preferentially selected. In the event multiple studies were available to identify the effect of an agent on a therapeutic target, the mean percent change was used. Conversely, if there was evidence that an agent would elicit a response on a given target but no mathematical representation of the difference was provided, conservative estimates consistent with the scale of other agents and the degree of glucose regulation were instituted to best represent the expected effect. Individual agents were then characterized for the 24 h percent change from baseline for CE, HGU, GNG, IR, PGU, and PIE. Carbohydrate exposure was determined as the combined effect of caloric intake and intestinal carbohydrate absorption. Hepatic glucose uptake was defined as the reported value obtained immediately following oral glucose loading. Because GNG is known to be enhanced in the fasting state and persistent throughout the prandial phase,[17,18] effect was determined during the fasting state and considered equivalent throughout the prandial phase. For studies evaluating fasting glucose and insulin concentrations, an index of IR was determined by homeostasis model assessment of insulin resistance (HOM-AIR) using the following formula: Insulin (mU/liter)×Glucose (mmol)/22.5.[19] To account for known differences in secretory and uptake dynamics during the fasting and prandial phases, studies identifying the impact of therapies during the fasting state (or simulated hyperinsulinemic euglycemic clamp) and prandial phase (or oral glucose load insulin clamp) were specifically identified for changes in PGU (glucose infusion rate) and PIE (insulin concentrations) according to Equation (1):

$$PIE24/PGU24 = \frac{(\text{Fasting Change})(12) + (\text{Prandial Change})(12)}{24} \quad (1)$$

For sulfonylurea and insulin-based therapies, insulin concentration time profiles were obtained and superimposed on the baseline 24 h insulin concentration time profile of T2D patients (FIG. 2) to calculate the increase in PIE (trapezoidal rule).[20] Calculated increases in incremental and cumulative insulin exposure were correlated to known insulin dose-response effects on HGU, GNG, and PGU (FIG. 3),[18,21] according to the equation y=mx+b. Twenty-four-hour increases in HGU, PGU, and PIE and decreases in GNG were compared to baseline values and percent change calculated.

With alpha-glucosidase, biguanide, TZD, secretagogue, and insulin therapies characterized for their respective impacts on CE, HGU, GNG, IR, PIE, and PGU, identification of their effect on the glucose supply (decrease in CE, increase in HGU, decrease in GNG, decrease in IR) and insulin demand (increase in PIE, increase in PGU) dynamic was assessed according to Equation (2), which provides the SD ratio according to the invention:

$$\text{Glucose Supply }(S)/\text{Insulin Demand }(D) = \frac{1 + ((CE) + (HGU) + (GNG) + (IR))}{1 + (PIE + PGU)} \quad (2)$$

Alpha-Glucosidase Inhibitors (Acarbose and Miglitol). The alpha-glucosidase inhibitors (1) have no significant effect on total caloric intake,[22] (2) delay and decrease carbohydrate absorption,[23-27] (3) have not been directly evaluated for HGU, (4) have negligible effect on hepatic glucose output,[28,29] (5) reduce IR,[22,30-33] (6) have variable effects on PGU,[22,28,30,34-38] and (7) reduce plasma insulin concentrations.[22,39-45] Studies meeting the review criteria for the target effects of the alpha-glucosidase inhibitors on the respective targets are summarized here. Estimates for the effect of alpha-glucosidase inhibitors on the respective targets are presented in Table 1.

Caloric Intake and Intestinal Carbohydrate Absorption

Meneilly and associates evaluated the effects of acarbose on total caloric intake by means of 3-day food recall and dietician interview.[22] Acarbose was administered at an initial dose of 50-100 mg three times daily. At the conclusion of 52 weeks of acarbose therapy, there was no significant change in proportion of calories as carbohydrate (−0.7±0.8%), fat (0.9±0.8%), or protein (−0.5±0.5%), nor was there a significant change in total caloric intake (90±50 kcal). Radziuk evaluated the effect of 0, 50, and 100 mg of acarbose on the absorption of the glucose moiety of sucrose in overnight-fasted subjects receiving labeled 100 g oral sucrose load ([1-$^{14}$C]glucose) and simultaneous intravenous infusion of [3-$^{3}$H]glucose.[24] Acarbose increased malabsorption in a dose-dependent manner; at 50 mg there was a modest effect (6%), whereas at 100 mg it was approximately 30%, and at the highest 150 mg dose approximately 66%. These findings are supported by Sobajima, where carbohydrate malabsorption, measured by hydrogen excretion following 2-month acarbose administration (50-100 mg three times daily) was estimated to be 31.6% of baseline.[25]

Hepatic Glucose Uptake and Hepatic Gluconeogenesis

No studies directly evaluate the impact of alpha-glucosidase inhibitors on HGU. However, evidence does suggest acarbose delays carbohydrate absorption[26,27] and increases glucagon-like peptide-1 secretion.[46,47] Therefore, it would be anticipated that alpha-glucosidase inhibitors would exhibit modest effects on retaining carbohydrate in the splancnic area. Likewise, there is limited data regarding the impact of alpha-glucosidase inhibitors on hepatic GNG. Schnack evaluated the effect of long-term miglitol therapy on hepatic glucose output in poorly controlled T2D patients (HbA1c=9.9%). After eight weeks of therapy (300 mg/day), miglitol had no significant effect on hepatic glucose output versus placebo (0.37±0.15 versus 0.35±0.17 mg/kg$^{-1}$/min$^{-1}$) under euglycemic clamp conditions.[28] Sels evaluated the effects of miglitol on fasting plasma glucose (FPG) in T2D patients. Finding similar results, 200 mg of miglitol at bedtime for 1 week was not associated with a change in hepatic glucose production.[29]

Insulin Resistance

In the study by Meneilly, IR was assessed at baseline and after 12 months of acarbose (HOMAIR). IR was significantly improved following acarbose treatment (6.1±0.5 versus 5.0±0.5).[22] At the same acarbose dose, Calle-Pascual observed reductions in FPG and fasting plasma insulin (FPI) and a slightly greater reduction in IR (~27%), as calculated by HOMAIR, after 16 weeks of therapy.[30] Concurrent with these results, Delgado observed an approximate 15% reduction in IR after 16 weeks of therapy at a lower therapeutic dose of acarbose (100 mg daily).[33] Contradicting the findings of the previous authors, Hanefeld as well as Fischer both found no significant alterations in IR.[38,41]

Peripheral Glucose Uptake

Kinoshita evaluated the effect of acarbose 300 mg daily on glucose utilization rate (M value) (mg/kg$^{-1}$/min$^{-1}$) under euglycemic hyperinsulinemic conditions.[37,48] After allowing the HbA1c to fall to ≤8%, baseline clamp study was performed, with follow-up study at 6 months. At the conclusion of therapy, glucose utilization rate was increased (8.00±1.96 versus 9.94±2.35 mg/kg$^{-1}$/min$^{-1}$). At the same daily dose for 16 weeks, Fischer observed a nonsignificant increase in glucose disposal rate during euglycemic hyperinsulinemic clamp (3.2 versus 2.3 mg/kg$^{-1}$/min$^{-1}$)[38] In the study by Meneilly, glucose infusion rate during the final 20 min of the 2 h hyperglycemic clamp (5.4 mM above basal) was assessed at baseline and after 12 months of therapy. Glucose infusion rate increased significantly after acarbose therapy (1.68±0.19 versus 2.69±0.19 mg/kg$^{-1}$/min$^{-1}$)[22] Despite this evidence, multiple studies under similar experimental conditions do not confirm the observed increases in peripheral glucose disposal after sustained alpha-glucosidase therapy.[28,35,36,49]

Peripheral Insulin Exposure

Numerous studies have identified a reduced postprandial insulin response following acarbose administration to T2D patients.[42-45] Meneilly as well as Hanefeld have both evaluated the combined fasting and postprandial effects of long-term acarbose administration.[22,41] Meneilly assessed fasting and postprandial insulin secretion at baseline and 12 months of acarbose therapy (100 mg three times daily), observing significant decreases in both increments (−13±4 and −271±159 pmol/liter, respectively).[22] Hanefeld evaluated the effect of acarbose therapy (100 mg three times daily) on the 24 h insulin concentration time profile. After 16 weeks of therapy, acarbose was not found to change the 24 h area under the curve of insulin from baseline.[41]

Biguanides (Metformin)

Metformin has been shown to (1) reduce caloric intake, (2) have variable effects on intestinal carbohydrate absorption, (3) increase HGU, (4) diminish hepatic GNG, (5) reduce IR, (6) increase PGU, and (7) reduce insulin exposure. Estimates for the effect of metformin on the respective targets are presented in Table 1.

Caloric Intake and Intestinal Carbohydrate Absorption

Anorexia is occasionally reported following the introduction of metformin therapy to T2D patients.[51] Lee and Morley evaluated the effect of metformin on caloric intake in patients with T2D. Patients were randomly given placebo, 850, or 1700 mg of metformin for 3 days and subsequently evaluated for caloric intake during three consecutive 10 min intake periods. Caloric intake was reduced during each eating interval in a dose-dependent manner. Total caloric intake during the 30 min period was reduced 30% and 50% at 850 and 1700 mg, respectively.[52] Despite the substantial reductions in caloric intake observed at the respective doses, it should be considered that the impact is thought to be sustained with only extremely high doses (>2 g/kg$^{-1}$/day$^{-1}$).[60,79] Animal and human studies to determine the impact of biguanides on intestinal carbohydrate absorption have yielded conflicting results.[53-59] Bailey reviewed the effects of metformin on intestinal glucose handling (absorption and metabolism) in animal and human models.[60] In vitro animal studies have demonstrated metformin to cause a concentration-dependent decrease in glucose transport at concentrations in the millimolar range.[61-64] In vivo, Wilcock and Bailey observed net glucose transfer in the serosal fluid was reduced 12% in mice at a dosage of 50 mg/kg (slightly greater than the maximum 3 g dose).[65] In a preparation of brush border vesicles isolated from rabbit intestine (5 mM metformin), Kessler observed a nominal decrease in glucose uptake.[66] In clinical studies of noninsulin-dependent diabetes mellitus patients, there is evidence to suggest that biguanides may delay the rate, but not the extent of glucose absorption.[58,67] During a 75 g oral glucose load challenge with labeled [1-$^{14}$C glucose], Jackson observed the absorption of glucose to be slightly delayed, but ultimately unaltered over the 3 h study period.[67] Metformin has also been noted to increase intestinal glucose utilization.[68,69] Penicaud administered 350 mg/kg$^{-1}$/day$^{-1}$ to obese fa/fa rats for 8 days, observing an increased glucose utilization by 39% in the jejunum.[68] During intravenous glucose tolerance test, Bailey administered metformin 250 mg/kg$^{-1}$ to normal rats, observing an increased glucose utilization by 30-60% in mucosa from different regions of the intestine.[69] Despite substantial increases in intestinal glucose utilization induced by metformin, it must be considered that evidence suggests an increased lactate exposure in the hepatic portal vein.[70] The increased exposure to lactate may yield increased glucose-lactate cycling between the splanchnic tissues and diminish the impact of intestinal metabolism on overall glycemia.[60]

Hepatic Glucose Uptake

Iozzo evaluated the impact of metformin (2000 mg daily) and rosiglitazone (8 mg daily) therapy on HGU.[71] Positron-emission tomography (PET) studies in combination with [$^{18}$F]2-fluoro-2-deoxyglucose ([$^{18}$F]FDG) and the insulin clamp technique[48] were performed before treatment and at 26 weeks to assess HGU. At 90 min of the 150 min normoglycemic hyperinsulinemic period, patients were intravenously administered [$^{18}$F]FDG and consecutive scans of the liver were obtained at 20 min. Although baseline HGU was not presented, metformin and rosiglitazone similarly and significantly increased HGU (placebo-subtracted value=+0.008±0.004 and +0.007±0.004 μmol/kg$^{-1/}$min$^{-1}$, respectively). Despite the failure of this study to define a specific increase versus baseline in HGU following an oral glucose load, the relationship identified between metformin and TZD would infer a similar impact.

Hepatic Gluconeogenesis

Stumvoll evaluated the metabolic effects of metformin in T2D patients receiving metformin 2550 mg daily.[72] Prior to and at the conclusion of the 16 week treatment period, patients were fasted and assessed for the rate of plasma lactate to plasma glucose conversion (GNG). Metformin was found to reduce the rate of conversion by 37% (7.3±0.7 versus 4.6±0.6 μmol/kg$^{-1/}$min$^{-1}$). Hundal also evaluated the mechanism by which metformin reduces glucose production in patients with T2D.[73] To address known methodological limitations used in previous studies assessing GNG, two independent and complimentary methods (nuclear magnetic resonance spectroscopy and $^2$H$_2$O method) were employed to assess the impact of metformin therapy (2550 mg daily). Supporting the findings of Stumvoll and associates, the rate of hepatic GNG was reduced 36% as evaluated by the nuclear magnetic resonance method (0.59±0.03 versus 0.18±0.03 mmol/m$^{-2/}$min$^{-1}$) and 33% by the $^2$H$_2$O method (0.42±0.04 versus 0.28±0.03 mmol/m$^{-2/}$min$^{-1}$) after 3 months of treatment.

Insulin Resistance

In a meta-analysis of randomized controlled trials in people at risk for T2D, metformin reduced calculated IR (HOMA-IR) by 22.6%. In studies of patients with T2D and maximal therapeutic doses of metformin (Iozzo, Stumvoll, Tiikkainen, and Sharma), calculated IR was reduced 38-44%.[71,72,74,75]

Peripheral Glucose Uptake

In the aforementioned analysis by Stumvoll, it was noted that the rate of plasma glucose turnover (hepatic glucose output and systemic glucose disposal) was reduced with metformin from 2.8±0.2 to 2.0±0.2 mg/kg$^{-1/}$min$^{-1}$.[72] Importantly, the reduction in plasma glucose turnover was attributed to the reduction in hepatic glucose output; systemic glucose disposal did not change.[72] Corroborating evidence that metformin does not substantially increase PGU, both Tiikkainen and Inzucchi observed nominal increases with long-term administration of metformin at therapeutic doses. Tiikkainen clamped patients at 144 mg/dl before and after 16 weeks of metformin 2000 mg daily. The glucose rate of disappearance remained unchanged (0.09±0.01 versus 0.10±0.01 mg/kg$^{-1}$/min$^{-1}$).[74] Inzucchi clamped patients at 100 mg/dl before and after 12 weeks of metformin 2000 mg daily. During the euglycemic hyperinsulinemic clamp period, glucose infusion rate was increased 13% (240 versus 272 mg/m$^{-2}$/min$^{-1}$).[78]

Peripheral Insulin Exposure

Metformin was consistently found to reduce FPI concentrations (range: 10-30%). In the aforementioned studies by Iozzo and Stumvoll, FPI was reduced ~30% (63±12 to 43.0±5.0 pmol/liter) and 17% (12±5 to 10±μU/ml), respectively.[71,72] Tiikkainen observed an ~30% reduction in FPI (13 versus 9 mU/liter), and Sharma found an ~10% reduction (76.0±54.5 to 69.0±45.0 pmol/liter) following administration of metformin 2000 mg daily for 16 weeks.[74,75] Evaluating both the fasting and mealtime effects of metformin, Inzucchi found mean fasting and postprandial plasma insulin concentrations to be slightly, but not significantly reduced with metformin 2000 mg daily for 12 weeks.[78]

Thiazolidinediones (Pioglitazone, Rosiglitazone, and Troglitazone)

The TZD agents (1) have no significant effect on total caloric intake, (2) have no evidence for diminished intestinal absorption, (3) increase HGU,[71,83,84] (4) diminish hepatic GNG, (5) reduce IR, (6) increase PGU, and (7) reduce insulin exposure. Studies meeting review criteria for the target effects of the TZDs are presented here. Estimates for the effect of TZDs on the respective targets are presented in Table 1.

Caloric Intake and Intestinal Carbohydrate Absorption

The effect of TZDs on caloric intake has been evaluated in T2D patients treated with pioglitazone and rosiglitazone. Smith estimated subjective measures of hunger (visual analog scale) and satiety in patients treated with pioglitazone 45 mg/day.[80] At the conclusion of 24-weeks, pioglitazone demonstrated no effect on hunger and satiety. Strowig and Raskin assessed caloric intake via food records in patients administered rosiglitazone 4 mg twice daily.[81] At the conclusion of 32-weeks, mean caloric intake did not differ between treatment groups (rosiglitazone 2066.4±589.2 and 1994.9±726.5 calories/day for baseline and week 32, respectively). The effect of troglitazone on caloric intake in patients with diabetes has not been directly evaluated. However, in healthy volunteers, Cominancini evaluated the effects of troglitazone 400 mg daily.[82] Troglitazone was not associated with changes in carbohydrate or total caloric intake after 2 weeks of therapy.

Hepatic Glucose Uptake

Bajaj and Kawamori have both evaluated the effect of pioglitazone on HGU.[83,84] Kawamori administered pioglitazone 30 mg daily to patients treated with either diet alone or sulfonylurea therapy. Following 12 weeks of therapy, the rate of splanchnic glucose uptake increased from 28.5±19.4% to 59.4±27.1% (p=0.010). Bajaj administered pioglitazone 45 mg once daily after a 48 h medication washout period. At 16 weeks, splanchnic glucose uptake increased from 33.0±2.8% to 46.2±5.1%.[83] As previously mentioned, Iozzo evaluated the effects of rosiglitazone on HGU, utilizing the insulin clamp technique and PET studies. After 26 weeks, rosiglitazone 4 mg twice daily significantly increased HGU versus placebo (+0.007 μmol/min$^{-1}$/kg$^{-1}$). Since the study did not present baseline data to allow for percent change calculation, rosiglitazone was considered to have similar characteristics to pioglitazone for HGU. Troglitazone has not been directly evaluated for impact on HGU and was considered comparable to pioglitazone and rosiglitazone.

Hepatic Gluconeogenesis

Gastaldelli evaluated the fasting and mixed-meal effects of pioglitazone and rosiglitazone on hepatic GNG.[17,85] Pioglitazone 45 mg daily for 16 weeks reduced fasting endogenous glucose production (13.1±0.3 versus 12.0±0.6 7 µmol/min$^{-1}$/kg$^{-1}$) and GNG contribution (73.1±2.4% versus 64.4±3.1%). During the mixed meal, endogenous glucose production was again reduced (6.5±0.7 versus 5.4±0.7 µmol/min$^{-1}$/kg$^{-1}$) as was the contribution of GNG to the total rate of appearance (45.6±1.7% versus 41.3±2.6%).[17] In the second study, rosiglitazone 8 mg daily for 12 weeks reduced fasting endogenous glucose production (18.6±0.9 versus 16.3±0.6 µmol/min$^{-1}$/kg$^{-1}$) and GNG contribution (67±4% versus 59±3%). The direct effect of troglitazone on hepatic GNG has not been evaluated. However, Inzucchi evaluated the effect of troglitazone on endogenous glucose production and found no significant difference after administration of troglitazone 400 mg daily for 12 weeks.[78]

Insulin Resistance

Langenfield evaluated the effect of pioglitazone on IR as determined by HOMA-IR.[86] Pioglitazone at a dose of 45 mg daily for 24 weeks in T2D patients resulted in a decrease in IR from 6.15±4.05 to 3.85±1.92. Comparative analyses have identified similar effects of pioglitazone and rosiglitazone on IR. In a 12-week trial of pioglitazone 45 mg daily and rosiglitazone 4 mg twice daily, Goldberg reported a reduction from 8.2±0.3 to 5.4±0.2 and 7.8±0.4 to 4.8±0.2, respectively.[87] Under the same experimental design, Deeg observed similar reductions in IR for pioglitazone and rosiglitazone (8.3 versus 5.4 and 7.9 versus 4.7, respectively).[88] Yatagai evaluated the effects of troglitazone 400 mg daily on IR (HOMA-IR). After 12 weeks, IR was reduced from 5.7±0.7 to 4.5±0.8.[89]

Peripheral Glucose Uptake

Pioglitazone, rosiglitazone, and troglitazone have been shown to increase basal and incremental PGU. Bajaj observed the glucose infusion rate to be significantly greater during euglycemic insulin clamp (5.6 mmol/liter) after treatment with pioglitazone 45 mg daily for 16 weeks (6.9±0.5 versus 5.0±0.5 mg/kg$^{-1}$/min$^{-1}$)[83] Glucose infusion rate was also significantly increased during the 180-420 min period of the 75 g oral glucose load-insulin clamp (5.3±0.5 versus 2.9±0.5 mg/kg$^{-1}$/min$^{-1}$). Tiikkainen demonstrated that rosiglitazone 4 mg twice daily for 16 weeks increased glucose disposal rate (0.10±0.02 versus 0.17 mg/kg$^{-1}$/min$^{-1}$) with glycemic maintenance at ~8 mmol/liter.[74] Inzucchi found administration of troglitazone 400 mg daily for 12 weeks significantly increased glucose disposal rate (172 versus 265 mg/m$^{-2}$/min$^{-1}$) during the final hour of hyperinsulinemic-euglycemic clamp study (5.6 mmol/liter).[78]

Peripheral Insulin Exposure

Gastaldelli evaluated the effect of pioglitazone 45 mg daily for 16 weeks on the metabolic and hormonal response to a mixed meal in T2D patients.[17] Fasting plasma insulin and plasma insulin during the mixed meal challenge (0-6 h) were similarly reduced versus baseline (88 versus 81 pmol/liter and 268 versus 248 pmol/liter, respectively). Miyazaki evaluated the dose-response effect of 7.5-45 mg of pioglitazone on fasting insulin secretion after 26 weeks. Fasting plasma insulin concentrations were similarly reduced (15-25%) at the respective pioglitazone doses.[90] Miyazaki and DeFronzo have reported that rosiglitazone demonstrates similar effects to pioglitazone on insulin secretion.[91] After 3 months of therapy with rosiglitazone 8 mg daily, FPI was reduced (18±1 versus 13±1 µU/ml) without change in the mean insulin concentration (37±4 versus 36±4 µU/ml) during a 2 h oral glucose tolerance test (OGTT). Pioglitazone similarly reduced FPI (15±1 versus 13±2 µU/ml) and also demonstrated no change in mean insulin concentration during a 2 h OGTT. Yatagai evaluated the effects of troglitazone 400 mg daily on FPI concentration in T2D patients.[89] After 12 weeks of therapy, FPI concentration was found to be slightly reduced (14.3±2.1 to 12.9±2.6 µU/ml). Similarly, Inzucchi evaluated the effects of troglitazone 400 mg daily for 12 weeks.[78] At the conclusion of the study, fasting and postprandial plasma insulin concentrations were reported to be slightly, but not significantly, reduced.

Secretagogues and Exogenous Insulin

Secretagogues and exogenous insulin (1) have variable effects on caloric intake,[92-104] (2) have no evidence for diminished intestinal carbohydrate absorption, (3) increase HGU,[21] (4) diminish GNG,[18,21] (5) have variable effects on IR,[38,103,105-112] (6) increase PGU,[21] and (7) increase PIE.[113-122]

Caloric Intake and Intestinal Carbohydrate Absorption

It has been hypothesized that increased plasma insulin concentrations increase appetite and cause undesirable weight gain.[92-95] The UKPDS and other studies in T2D patients have demonstrated that initiation of insulin is often accompanied by duration and intensity dependent weight gain (5-10%).[96-100] The potential cause of increased weight gain has been attributed to increased caloric intake secondary to hyperinsulinemia or hypoglycemic fear and also a reduction in the basal metabolic rate.[97,101,102] However, it must be considered that weight gain is not a universal finding and that modest reductions in daily caloric intake have been observed.[103,104] Moreover, insulin therapy is commonly, but not unequivocally, associated with increased caloric intake and subsequent weight gain.

Standard and Insulin Concentration Time Profiles

Figure 2:
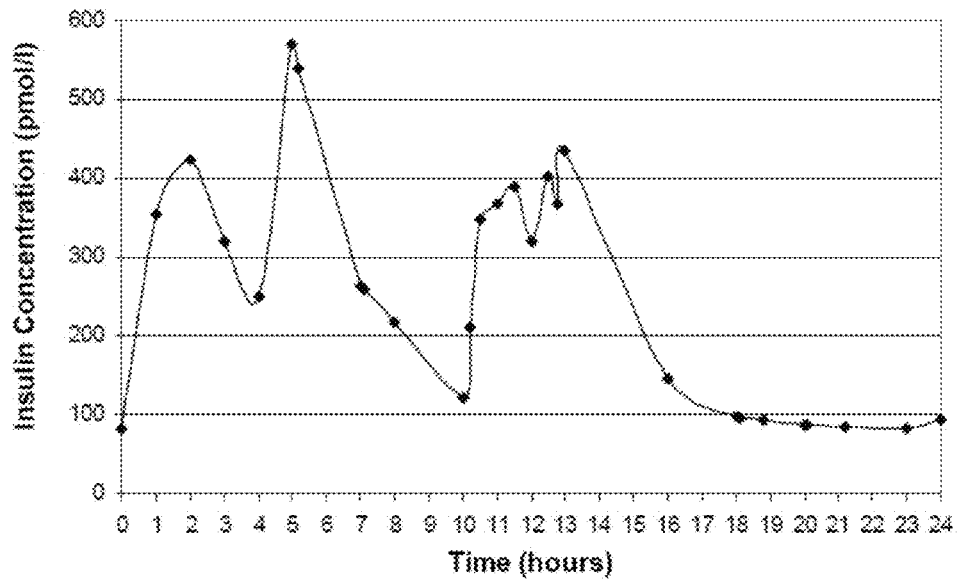
FIG. 2 is a graphical representation of a standard insulin concentration time profile for Type 2 diabetes (T2D).

Gannon and Nuttall identified the 24 h insulin secretion profile in patients with T2D prior to initiating dietary control measures (FIG. 2). On average, patients were aged 63 years (range 51-82), with a 4-year duration of diabetes (range 1-15), BMI of 31 kg/m$^2$ (range 27-36), and a total glycosylated hemoglobin of 9.6% (range 8.6-11.2).[20]

Hepatic Glucose Uptake, Hepatic Gluconeogenesis, and Peripheral Glucose Uptake

Basu evaluated the insulin dose-response curves for stimulation of splanchnic (hepatic) glucose uptake, suppression of endogenous glucose production, and PGU.[21] Patients were fed a standard 10 cal/kg meal (55% carbohydrate, 30% fat, 15% protein) and stabilized overnight at a glucose level of ~5 mmol/liter (90 mg/dl). On the subsequent morning, insulin was infused at variable rates from 0 to 180 min (~0.5 mU/kg$^{-i}$/min$^{-1}$), 181 to 300 min (~1.0 mU/kg$^{-1}$/min$^{-1}$), and 301 to 420 min (~2.0 mU/kg$^{-1}$/min$^{-1}$) The insulin dose-response relationship for splanchnic glucose uptake and PGU during the final 30 min of the low- (~150 pmol/liter), medium- (~350 pmol/liter), and high- (~700 pmol/liter) dose insulin infusions are presented in FIG. 3. To most accurately quantify the hepatic contribution to glucose supply, the insulin dose-response relationship to hepatic GNG was utilized in place of total endogenous glucose production. Gastaldelli evaluated the effect of physiological hyperinsulinemia on GNG in T2D.[18] Under euglycemic clamp conditions, total rates of glucose appearance were calculated from a previously established two-compartmental model.[123] Endogenous glucose output was subsequently calculated as the difference between the rate of glucose appearance and the exogenous glucose rate. Percent contribution of GNG to the plasma glucose was calculated as the ratio of $C5:{}^2H_2O$ enrichments. Under basal conditions, mean plasma insulin concentration was 12.2±1.2 μU/ml (~85 pmol/liter) and increased to 113±6 μU/ml (~780 pmol/liter) during euglycemic hyperinsulinemic clamp. Endogenous glucose output reduced from 15.2±0.4 to 7.1±0.9 and plasma $C5:{}^2H_2O$ ratio declined from 0.60±0.02 to 0.25±0.02. The insulin dose-response relationship for suppression of hepatic GNG is presented in FIG. 3.

Insulin and Sulfonylurea Concentration Time Profiles

Twenty-four-hour insulin concentration time curves were obtained for sulfonylurea, meglitinide, and exogenously administered insulin products.[113-122] Due to a lack of available evidence characterizing the 24 h insulin concentration profile of first generation sulfonylurea agents, comparable dose relationships were drawn with the profile for glyburide. Twenty-four-hour steady state insulin concentration time curves were superimposed on the baseline secretion profile of the standard T2D patient. As an example, the concentration time profile of insulin glargine at a dose of 0.5 U/kg is presented in FIG. 4. Using the trapezoidal rule, glargine increased PIE 30% versus baseline (5765 versus 7495 $pmol/h^{-1}/liter^{-1}$, respectively). Applying the superimposed 24 h insulin concentration time curve to the insulin dose-response relationships for HGU, GNG, and PGU, glargine was observed to increase HGU and PGU (24% and 42%, respectively), while decreasing GNG 10%. Hepatic glucose uptake, GNG, PGU, and PIE values for the remaining exogenously administered insulin products and sulfonylurea agents are presented in Table 1.

Insulin Resistance

In 1993, Hotamisligil and colleagues identified the relationship between inflammation and metabolic conditions, such as obesity and IR, by demonstrating adipocyte expression of the pro-inflammatory cytokine tumor necrosis factor-α (TNF-α) and that expression in the adipocytes of obese animals is markedly increased.[124] Further efforts in the area of obesity have identified obesity to be a state of chronic inflammation, as indicated by increased plasma concentrations of C-reactive protein, interleukin-6 (IL-6), and plasminogen activator inhibitor-1 (PAI-1).[125-127] Dandona has characterized the anti-inflammatory effect of insulin (reduction of reactive oxygen species generation by mononuclear cells, nicotinamide adenine dinucleotide phosphate oxidase suppression, reduced intranuclear NF-κB, suppressed plasma intercellular adhesion molecule-1 and monocyte chemotactic protein-1, reduced intranuclear Egr-1, monocyte chemotactic protein-1 and PAI-1) as well as the link between IR, obesity, and diabetes.[128-130] Crook and Pickup first proposed T2D to be a chronic inflammatory condition characterized by increased concentrations of acute phase reactants (sialic acid, IL-6).[131,132] Indeed, several studies have confirmed the presence of inflammatory mediators predicts T2D.[133-139] It has been noted that the increased concentration of pro-inflammatory cytokines (i.e. TNF-α, IL-6) associated with obesity and T2D may interfere with insulin action by suppressing signal transduction. Therefore, the anti-inflammatory effects of insulin may be blunted, which in turn may promote inflammation.[130]

The extensive characterization of obesity and T2D as inflammatory conditions with blunted anti-inflammatory (and possibly pro-inflammatory) effects of insulin creates inconsistency when characterizing insulin's effect on IR. It has been argued that, by increasing weight gain, insulin therapy would exacerbate IR.[112] So too, there is conflicting evidence that insulin and sulfonylurea agents have no significant effect, or alternatively a beneficial effect, on IR as assessed by HOMA-IR. Contradictory evidence in combination with known pathophysiologic evidence would indicate a net neutral effect of insulin on IR.

References for Example 1

13. DeFronzo R A, Ferrannini E, Hendler R, Wahren J, Felig P. Influence of hyperinsulinemia, hyperglycemia, and the route of glucose administration on splanchnic glucose exchange. Proc Natl Acad Sci USA. 1978; 75(10):5173-7.
14. Toschi E, Camastra S, Sironi A M, Masoni A, Gastaldelli A, Mari A, Ferrannini E, Natali A. Effect of acute hyperglycemia on insulin secretion in humans. Diabetes. 2002; 51 Suppl 1:S130-3.
15. Elahi D, Nagulesparan M, Hershcopf R J, Muller D C, Tobin J D, Blix P M, Rubenstein A H, Unger R H, Andres R. Feedback inhibition of insulin secretion by insulin: relation to the hyperinsulinemia of obesity. N Engl J Med. 1982; 306(20):1196-202.
16. Erdmann J, Mayr M, Oppel U, Sypchenko O, Wagenpfeil S, Schusdziarra V. Weight-dependent differential contribution of insulin secretion and clearance to hyperinsulinemia of obesity. Regul Pept. 2009; 152(1-3):1-7.
17. Gastaldelli A, Casolaro A, Pettiti M, Nannipieri M, Ciociaro D, Frascerra S, Buzzigoli E, Baldi S, Mari A, Ferrannini E. Effect of pioglitazone on the metabolic and hormonal response to a mixed meal in type II diabetes. Clin Pharmacol Ther. 2007; 81(2):205-12.
18. Gastaldelli A, Toschi E, Pettiti M, Frascerra S, Quiñones-Galvan A, Sironi A M, Natali A, Ferrannini E. Effect of physiological hyperinsulinemia on gluconeogenesis in nondiabetic subjects and in type 2 diabetic patients. Diabetes. 2001; 50(8):1807-12.
19. Matthews D R, Hosker J P, Rudenski A S, Naylor B A, Treacher D F, Turner R C. Homeostasis model assessment: insulin resistance and beta-cell function from fasting plasma glucose and insulin concentrations in man. Diabetologia. 1985; 28(7):412-9.
20. Gannon M C, Nuttall F Q. Effect of a high-protein, low-carbohydrate diet on blood glucose control in people with type 2 diabetes. Diabetes. 2004; 53(9):2375-82.
21. Basu R, Basu A, Johnson C M, Schwenk W F, Rizza R A. Insulin dose-response curves for stimulation of splanchnic glucose uptake and suppression of endogenous glucose production differ in nondiabetic humans and are abnormal in people with type 2 diabetes. Diabetes. 2004; 53(8):2042-50.
22. Meneilly G S, Ryan E A, Radziuk J, Lau D C, Yale J F, Morais J, Chiasson J L, Rabasa-Lhoret R, Maheux P, Tessier D, Wolever T, Josse R G, Elahi D. Effect of acarbose on insulin sensitivity in elderly patients with diabetes. Diabetes Care. 2000; 23(8):1162-7.
23. Laube H. Acarbose: an update of its therapeutic use in diabetes treatment. Clin Drug Invest. 2002; 22(3):141-56.
24. Radziuk J, Kemmer F, Morishima T, Berchtold P, Vranic M. The effects of an alpha-glucoside hydrolase inhibitor on glycemia and the absorption of sucrose in man determined using a tracer method. Diabetes. 1984; 33(3):207-13.
25. Sobajima H, Mori M, Niwa T, Muramatsu M, Sugimoto Y, Kato K, Naruse S, Kondo T, Hayakawa T. Carbohydrate malabsorption following acarbose administration. Diabet Med. 1998; 15(5):393-7.
26. Coniff R F, Shapiro J A, Robbins D, Kleinfield R, Seaton T B, Beisswenger P, McGill J B. Reduction of glycosylated hemoglobin and postprandial hyperglycemia by acarbose in patients with NIDDM. A placebo-controlled dose-comparison study. Diabetes Care. 1995; 18(6):817-24.
27. Hanefeld M, Fischer S, Schulze J, Spengler M, Wargenau M, Schollberg K, Fücker K. Therapeutic potentials of acarbose as first-line drug in NIDDM insufficiently treated with diet alone. Diabetes Care. 1991; 14(8):732-7.
28. Schnack C, Prager R J, Winkler J, Klauser R M, Schneider B G, Schernthaner G. Effects of 8-wk alpha-glucosidase inhibition on metabolic control, C-peptide secretion, hepatic glucose output, and peripheral insulin sensitivity in poorly controlled type II diabetic patients. Diabetes Care. 1989; 12(8):537-43.
29. Sels J P, Kingma P J, Wolffenbuttel B H, Menheere P P, Branolte J H, Nieuwenhuijzen Kruseman A C. Effect of miglitol (BAY m-1099) on fasting blood glucose in type 2 diabetes mellitus. Neth J Med. 1994; 44(6):198-201.
30. Calle-Pascual A, Garcia-Honduvilla J, Martin-Alvarez P J, Calle J R, Maranes J P. Influence of 16-week monotherapy with acarbose on cardiovascular risk factors in obese subjects with non-insulin-dependent diabetes mellitus: a controlled, double-blind comparison study with placebo. Diabetes Metab. 1996; 22(3):201-2.
31. Chiasson J L, Josse R G, Leiter L A, Mihic M, Nathan D M, Palmason C, Cohen R M, Wolever T M. The effect of acarbose on insulin sensitivity in subjects with impaired glucose tolerance. Diabetes Care. 1996; 19(11):1190-3.
32. Shinozaki K, Suzuki M, Ikebuchi M, Hirose J, Hara Y, Harano Y. Improvement of insulin sensitivity and dyslipidemia with a new alpha-glucosidase inhibitor, voglibose, in nondiabetic hyperinsulinemic subjects. Metabolism. 1996; 45(6):731-7.
33. Delgado H, Lehmann T, Bobbioni-Harsch E, Ybarra J, Golay A. Acarbose improves indirectly both insulin resistance and secretion in obese type 2 diabetic patients. Diabetes Metab. 2002; 28(3):195-200.
34. Laube H, Linn T, Heyen P. The effect of acarbose on insulin sensitivity and proinsulin in overweight subjects with impaired glucose tolerance. Exp Clin Endocrinol Diabetes. 1998; 106(3):231-3.
35. Reaven G M, Lardinois C K, Greenfield M S, Schwartz H C, Vreman H J. Effect of acarbose on carbohydrate and lipid metabolism in NIDDM patients poorly controlled by sulfonylureas. Diabetes Care. 1990; 13 Suppl 3:32-6.
36. Jenney A, Proietto J, O'Dea K, Nankervis A, Traianedes K, D'Embden H. Low-dose acarbose improves glycemic control in NIDDM patients without changes in insulin sensitivity. Diabetes Care. 1993; 16(2):499-502.
37. Kinoshita T, Maeda H, Urata S, Hirao K. Effect of acarbose versus sulfonylurea therapy on insulin sensitivity: an insulin clamp study. Curr Ther Res. 1999; 61(2):97-104.
38. Fischer S, Patzak A, Rietzsch H, Schwanebeck U, Köhler C, Wildbrett J, Fuecker K, Temelkova-Kurktschiev T, Hanefeld M. Influence of treatment with acarbose or glibenclamide on insulin sensitivity in type 2 diabetic patients. Diabetes Obes Metab. 2003; 5(1):38-44.
39. Hillebrand I, Boehme K, Graefe K H, Wehling K. The effect of new alpha-glucosidase inhibitors (BAY m 1099 and BAY o 1248) on meal-stimulated increases in glucose and insulin levels in man. Klin Wochenschr. 1986; 64(8):393-6.
40. Hillebrand I, Boehme K, Frank G, Fink H, Berchtold P. The effects of the alpha-glucosidase inhibitor BAY g 5421 (Acarbose) on meal-stimulated elevations of circulating glucose, insulin, and triglyceride levels in man. Res Exp Med (Berl). 1979; 175(1):81-6.
41. Hanefeld M, Haffner S M, Menschikowski M, Koehler C, Temelkova-Kurktschiev T, Wildbrett J, Fischer S. Different effects of acarbose and glibenclamide on proinsulin and insulin profiles in people with type 2 diabetes. Diabetes Res Clin Pract. 2002; 55(3):221-7.
42. Uttenthal L O, Ukponmwan O O, Wood S M, Ghiglione M, Ghatei M A, Trayner I M, Bloom S R. Long-term effects of intestinal alpha-glucosidase inhibition on postprandial glucose, pancreatic and gut hormone responses and fasting serum lipids in diabetics on sulphonylureas. Diabet Med. 1986; 3(2):155-60.
43. Hoffmann J, Spengler M. Efficacy of 24-week monotherapy with acarbose, glibenclamide, or placebo in NIDDM patients. The Essen Study. Diabetes Care. 1994; 17(6):561-6.
44. Inoue I, Takahashi K, Noji S, Awata T, Negishi K, Katayama S. Acarbose controls postprandial hyperproinsulinemia in non-insulin dependent diabetes mellitus. Diabetes Res Clin Pract. 1997; 36(3):143-51.
45. Rosak C, Haupt E, Walter T, Werner J. The effect of combination treatment with acarbose and glibenclamide on postprandial glucose and insulin profiles: additive blood glucose lowering effect and decreased hypoglycaemia. Diabetes Nutr Metab. 2002; 15(3):143-51.
46. Seifarth C, Bergmann J, Holst J J, Ritzel R, Schmiegel W, Nauck M A. Prolonged and enhanced secretion of glucagon-like peptide 1 (7-36 amide) after oral sucrose due to alpha-glucosidase inhibition (acarbose) in type 2 diabetic patients. Diabet Med. 1998; 15(6):485-91.
47. Gutzwiller J P. Glucagon like peptide-1 is a physiologic regulator of food intake in humans. Gastroenterology. 1997; 112:A1153.
48. DeFronzo R A, Tobin J D, Andres R. Glucose clamp technique: a method for quantifying insulin secretion and resistance. Am J Physiol. 1979; 237(3):E214-23.
49. Holman R R, Cull C A, Turner R C. A randomized double-blind trial of acarbose in type 2 diabetes shows improved glycemic control over 3 years (U.K. Prospective Diabetes Study 44). Diabetes Care. 1999; 22(6):960-4.
50. Paolisso G, Amato L, Eccellente R, Gambardella A, Tagliamonte M R, Varricchio G, Carella C, Giugliano D, D'Onofrio F. Effect of metformin on food intake in obese subjects. Eur J Clin Invest. 1998; 28(6):441-6.
51. Hermann L S. Metformin: a review of its pharmacological properties and therapeutic use. Diabete Metab. 1979; 5(3):233-45.
52. Lee A, Morley J E. Metformin decreases food consumption and induces weight loss in subjects with obesity with type II non-insulin-dependent diabetes. Obes Res. 1998; 6(1):47-53.
53. Caspary W F. Biguanides and intestinal absorptive function. Acta Hepatogastroenterol (Stung). 1977; 24(6):473-80.
54. Czyzyk A, Tawecki J, Sadowski J, Ponikowska I, Szczepanik Z. Effect of biguanides on intestinal absorption of glucose. Diabetes. 1968; 17(8):492-8.
55. Berger W, Kunzli H. Effect of dimethylbiguanide on insulin, glucose and lactic acid contents observed in portal vein blood and peripheral venous blood in the course of intraduodenal glucose tolerance tests. Diabetologia. 1970; 6:37.

56. Gyr M, Berger W, Fridrich R, Denes A, Stadler G A. Der Einfluss von Dimethylbiguanid auf die Magenentleerung and die orale glucosetoleranz. Schw Med Wschr. 1971; 101:1876-9.
57. Adnitt P, Frayn K N. Effect of metformin on intestinal absorption and intravenous glucose tolerance in man. J Pharmacol. 1971; 2:202-4.
58. Fossati P, Fontaine P, Beuscart R, Romon M, Bourdelle-Hego M F, LePoutre-Vaast D. Escape of non insulin dependent diabetes (NIDD) to the oral hypoglycemic agents control. Rev Fr Endocrinol Clin. 1985; 26:105-16.
59. Cuber J C, Bosshard A, Vidal H, Vega F, Wiernsperger N, Rapin J R. Metabolic and drug distribution studies do not support direct inhibitory effects of metformin on intestinal glucose absorption. Diabete Metab. 1994; 20(6):532-9.
60. Bailey C J. Metformin and intestinal glucose handling. Diabetes Metab Rev. 1995; 11 Suppl 1:S23-32.
61. Caspary W F, Creutzfeldt W. Analysis of the inhibitory effect of biguanides on glucose absorption: inhibition of active sugar transport. Diabetologia. 1971; 7(5):379-85.
62. Lorch E Inhibition of intestinal absorption and improvement of oral glucose tolerance by biguanides in the normal and in the streptozotocin-diabetic rat. Diabetologia. 1971; 7(3):195-203.
63. Coupar I M, McColl I. Glucose absorption from the rat jejunum during acute exposure to metformin and phenformin. J Pharm Pharmacol. 1974; 26(12):997-8.
64. Wilcock C, Bailey C J. Accumulation of metformin by tissues of the normal and diabetic mouse. Xenobiotica. 1994; 24(1):49-57.
65. Wilcock C, Bailey C J. Reconsideration of inhibitory effect of metformin on intestinal glucose absorption. J Pharm Pharmacol. 1991; 43(2):120-1.
66. Kessler M, Meier W, Storelli C, Semenza G. The biguanide inhibition of D-glucose transport in membrane vesicles from small intestine brush borders. Biochim Biophys Acta. 1975; 413(3):444-52.
67. Jackson R A, Hawa M I, Jaspan J B, Sim B M, Disilvio L, Featherbe D, Kurtz A B. Mechanism of metformin action in non-insulin-dependent diabetes. Diabetes. 1987; 36(5):632-40.
68. Pénicaud L, Hitier Y, Ferré P, Girard J. Hypoglycaemic effect of metformin in genetically obese (fa/fa) rats results from an increased utilization of blood glucose by intestine. Biochem J. 1989; 262(3):881-5.
69. Bailey C J, Mynett K J, Page T. Importance of the intestine as a site of metformin-stimulated glucose utilization. Br J Pharmacol. 1994; 112(2):671-5.
70. Bailey C J, Wilcock C, Day C. Effect of metformin on glucose metabolism in the splanchnic bed. Br J Pharmacol. 1992; 105(4):1009-13.
71. Iozzo P, Hallsten K, Oikonen V, Virtanen K A, Parkkola R, Kemppainen J, Solin O, Lonnqvist F, Ferrannini E, Knuuti J, Nuutila P. Effects of metformin and rosiglitazone monotherapy on insulin-mediated hepatic glucose uptake and their relation to visceral fat in type 2 diabetes. Diabetes Care. 2003; 26(7):2069-74.
72. Stumvoll M, Nurjhan N, Perriello G, Dailey G, Gerich J E. Metabolic effects of metformin in non-insulin-dependent diabetes mellitus. N Engl J Med. 1995; 333(9):550-4.
73. Hundal R S, Krssak M, Dufour S, Laurent D, Lebon V, Chandramouli V, Inzucchi S E, Schumann W C, Petersen K F, Landau B R, Shulman G I. Mechanism by which metformin reduces glucose production in type 2 diabetes. Diabetes. 2000; 49(12):2063-9.
74. Tiikkainen M, Hakkinen A M, Korsheninnikova E, Nyman T, Makimattila S, Yki-Järvinen H. Effects of rosiglitazone and metformin on liver fat content, hepatic insulin resistance, insulin clearance, and gene expression in adipose tissue in patients with type 2 diabetes. Diabetes. 2004; 53(8):2169-76.
75. Sharma P K, Bhansali A, Sialy R, Malhotra S, Pandhi P. Effects of pioglitazone and metformin on plasma adiponectin in newly detected type 2 diabetes mellitus. Clin Endocrinol (Oxf). 2006; 65(6):722-8.
76. Mather K J, Verma S, Anderson T J. Improved endothelial function with metformin in type 2 diabetes mellitus. J Am Coll Cardiol. 2001; 37(5):1344-50.
77. Salpeter S R, Buckley N S, Kahn J A, Salpeter E E. Meta-analysis: metformin treatment in persons at risk for diabetes mellitus. Am J Med. 2008; 121(2):149-57.e2.
78. Inzucchi S E, Maggs D G, Spollett G R, Page S L, Rife F S, Walton V, Shulman G I. Efficacy and metabolic effects of metformin and troglitazone in type II diabetes mellitus. N Engl J Med. 1998; 338(13):867-72.
79. Bailey C J, Flatt P R, Ewan C. Anorectic effect of metformin in lean and genetically obese hyperglycaemic (ob/ob) mice. Arch Int Pharmacodyn Ther. 1986; 282(2): 233-9.
80. Smith S R, De Jonge L, Volaufova J, Li Y, Xie H, Bray G A. Effect of pioglitazone on body composition and energy expenditure: a randomized controlled trial. Metabolism. 2005; 54(1):24-32.
81. Strowig S M, Raskin P. The effect of rosiglitazone on overweight subjects with type 1 diabetes. Diabetes Care. 2005; 28(7):1562-7.
82. Cominacini L, Young M M, Capriati A, Garbin U, Fratta Pasini A, Campagnola M, Davoli A, Rigoni A, Contessi G B, Lo Cascio V. Troglitazone increases the resistance of low density lipoprotein to oxidation in healthy volunteers. Diabetologia. 1997; 40(10):1211-8.
83. Bajaj M, Suraamornkul S, Pratipanawatr T, Hardies L J, Pratipanawatr W, Glass L, Cersosimo E, Miyazaki Y, DeFronzo R A. Pioglitazone reduces hepatic fat content and augments splanchnic glucose uptake in patients with type 2 diabetes. Diabetes. 2003; 52(6):1364-70.
84. Kawamori R, Matsuhisa M, Kinoshita J, Mochizuki K, Niwa M, Arisaka T, Ikeda M, Kubota M, Wada M, Kanda T, Ikebuchi M, Tohdo R, Yamasaki Y. Pioglitazone enhances splanchnic glucose uptake as well as peripheral glucose uptake in non-insulin-dependent diabetes mellitus. AD-4833 Clamp-OGL Study Group. Diabetes Res Clin Pract. 1998; 41(1):35-43.
85. Gastaldelli A, Miyazaki Y, Pettiti M, Santini E, Ciociaro D, Defronzo R A, Ferrannini E. The effect of rosiglitazone on the liver: decreased gluconeogenesis in patients with type 2 diabetes. J Clin Endocrinol Metab. 2006; 91(3): 806-12.
86. Langenfeld M R, Forst T, Hohberg C, Kann P, Li bben G, Konrad T, Füllert S D, Sachara C, Pfiitzner A. Pioglitazone decreases carotid intima-media thickness independently of glycemic control in patients with type 2 diabetes mellitus: results from a controlled randomized study. Circulation. 2005; 111(19):2525-31.
87. Goldberg R B, Kendall D M, Deeg M A, Buse J B, Zagar A J, Pinaire J A, Tan M H, Khan M A, Perez A T, Jacober S J, GLAI Study Investigators. A comparison of lipid and glycemic effects of pioglitazone and rosiglitazone in patients with type 2 diabetes and dyslipidemia. Diabetes Care. 2005; 28(7):1547-54.
88. Deeg M A, Buse J B, Goldberg R B, Kendall D M, Zagar A J, Jacober S J, Khan M A, Perez A T, Tan M H, GLAI Study Investigators. Pioglitazone and rosiglitazone have different effects on serum lipoprotein particle concentrations and sizes in patients with type 2 diabetes and dyslipidemia. Diabetes Care. 2007; 30(10):2458-64.
89. Yatagai T, Nakamura T, Nagasaka S, Kusaka I, Ishikawa S E, Yoshitaka A, Ishibashi S. Decrease in serum C-reactive protein levels by troglitazone is associated with pretreatment insulin resistance, but independent of its effect on glycemia, in type 2 diabetic subjects. Diabetes Res Clin Pract. 2004; 63(1):19-26.
90. Miyazaki Y, Matsuda M, DeFronzo R A. Dose-response effect of pioglitazone on insulin sensitivity and insulin secretion in type 2 diabetes. Diabetes Care. 2002; 25(3): 517-23.
91. Miyazaki Y, DeFronzo R A. Rosiglitazone and pioglitazone similarly improve insulin sensitivity and secretion, glucose tolerance and adipocytokines in type 2 diabetic patients. Diabetes Obes Metab. 2008; 10(12):1204-11.
92. Grossman S P. The role of glucose, insulin and glucagon in the regulation of food intake and body weight. Neurosci Biobehav Rev. 1986; 10(3):295-315.
93. Grossman M I, Stein I F Jr. Vagotomy and the hunger-producing action of insulin in man. J Appl Physiol. 1948; 1(4):263-9.
94. Thompson D A, Campbell R G. Hunger in humans induced by 2-deoxy-D-glucose: glucoprivic control of taste preference and food intake. Science. 1977; 198 (4321):1065-8.
95. Westphal S A, Palumbo P J. Weight gain and management concerns in patients on insulin therapy. Insulin. 2007; 2:31-6.
96. Henry R R, Gumbiner B, Ditzler T, Wallace P, Lyon R, Glauber H S. Intensive conventional insulin therapy for type II diabetes. Metabolic effects during a 6-mo outpatient trial. Diabetes Care. 1993; 16(1):21-31.
97. Makimattila S, Nikkilä K, Yki-Järvinen H. Causes of weight gain during insulin therapy with and without metformin in patients with type II diabetes mellitus. Diabetologia. 1999; 42(4):406-12.
98. Lindström T, Eriksson P, Olsson A G, Arnqvist H J. Long-term improvement of glycemic control by insulin treatment in NIDDM patients with secondary failure. Diabetes Care. 1994; 17(7):719-21.
99. Yki-Järvinen H, Ryysy L, Kauppila M, Kujansuu E, Lahti J, Marjanen T, Niskanen L, Rajala S, Salo S, Seppälä P, Tulokas T, Viikari J, Taskinen M R. Effect of obesity on the response to insulin therapy in noninsulin-dependent diabetes mellitus. J Clin Endocrinol Metab. 1997; 82(12):4037-43.
100. Mudaliar S, Edelman S V. Insulin therapy in type 2 diabetes. Endocrinol Metab Clin North Am. 2001; 30(4): 935-82.
101. Rodin J, Wack J, Ferrannini E, DeFronzo R A. Effect of insulin and glucose on feeding behavior. Metabolism. 1985; 34(9):826-31.
102. Heller S. Weight gain during insulin therapy in patients with type 2 diabetes mellitus. Diabetes Res Clin Pract. 2004; 65 Suppl 1:S23-7.
103. Andrews W J, Vasquez B, Nagulesparan M, Klimes I, Foley J, Unger R, Reaven G M. Insulin therapy in obese, non-insulin-dependent diabetes induces improvements in insulin action and secretion that are maintained for two weeks after insulin withdrawal. Diabetes. 1984; 33(7): 634-42.
104. Ohkubo Y, Kishikawa H, Araki E, Miyata T, Isami S, Motoyoshi S, Kojima Y, Furuyoshi N, Shichiri M. Intensive insulin therapy prevents the progression of diabetic microvascular complications in Japanese patients with non-insulin-dependent diabetes mellitus: a randomized prospective 6-year study. Diabetes Res Clin Pract. 1995; 28(2):103-17.
105. Inukai K, Watanabe M, Nakashima Y, Sawa T, Takata N, Tanaka M, Kashiwabara H, Yokota K, Suzuki M, Kurihara S, Awata T, Katayama S. Efficacy of glimepiride in Japanese type 2 diabetic subjects. Diabetes Res Clin Pract. 2005; 68(3):250-7.
106. Koshiba K, Nomura M, Nakaya Y, Ito S. Efficacy of glimepiride on insulin resistance, adipocytokines, and atherosclerosis. J Med Invest. 2006; 53(1-2):87-94.
107. Scarlett J A, Gray R S, Griffin J, Olefsky J M, Kolterman O G. Insulin treatment reverses the insulin resistance of type II diabetes mellitus. Diabetes Care. 1982; 5(4):353-63.
108. Garvey W T, Olefsky J M, Griffin J, Hamman R F, Kolterman O G. The effect of insulin treatment on insulin secretion and insulin action in type II diabetes mellitus. Diabetes. 1985; 34(3):222-34.
109. Dorkhan M, Frid A, Groop L. Differences in effects of insulin glargine or pioglitazone added to oral anti-diabetic therapy in patients with type 2 diabetes: what to add—insulin glargine or pioglitazone? Diabetes Res Clin Pract. 2008; 82(3):340-5.
110. Li J, Tian H, Li Q, Wang N, Wu T, Liu Y, Ni Z, Yu H, Liang J, Luo R, Li Y, Huang L. Improvement of insulin sensitivity and beta-cell function by nateglinide and repaglinide in type 2 diabetic patients—a randomized controlled double-blind and double-dummy multicentre clinical trial. Diabetes Obes Metab. 2007; 9(4):558-65.
111. Uwaifo G I, Ratner R E. Differential effects of oral hypoglycemic agents on glucose control and cardiovascular risk. Am J Cardiol. 2007; 99(4A):51B-67B.
112. Genuth S. Insulin use in NIDDM. Diabetes Care. 1990; 13(12):1240-64.
113. Groop L, Wåhlin-Boll E, Groop P H, Tötterman K J, Melander A, Tolppanen E M, Fyhrqvist F. Pharmacokinetics and metabolic effects of glibenclamide and glipizide in type 2 diabetics. Eur J Clin Pharmacol. 1985; 28(6):697-704.
114. Strange P, Schwartz S L, Graf R J, Polvino W, Weston I, Marbury T C, Huang W C, Goldberg R B. Pharmacokinetics, pharmacodynamics, and dose-response relationship of repaglinide in type 2 diabetes. Diabetes Technol Ther. 1999; 1(3):247-56.
115. McLeod J F. Clinical pharmacokinetics of nateglinide: a rapidly-absorbed, short-acting insulinotropic agent. Clin Pharmacokinet. 2004; 43(2):97-120.
116. Plank J, Wutte A, Brunner G, Siebenhofer A, Semlitsch B, Sommer R, Hirschberger S, Pieber T R. A direct comparison of insulin aspart and insulin lispro in patients with type 1 diabetes. Diabetes Care. 2002; 25(11):2053-7.
117. Mudaliar S R, Lindberg F A, Joyce M, Beerdsen P, Strange P, Lin A, Henry R R. Insulin aspart (B28 asp-insulin): a fast-acting analog of human insulin: absorption kinetics and action profile compared with regular human insulin in healthy nondiabetic subjects. Diabetes Care. 1999; 22(9):1501-6.
118. Heinemann L, Linkeschova R, Rave K, Hompesch B, Sedlak M, Heise T. Time-action profile of the long-acting insulin analog insulin glargine (HOE901) in comparison with those of NPH insulin and placebo. Diabetes Care. 2000; 23(5):644-9.

119. Heine R J, Bilo H J, Fonk T, van der Veen E A, van der Meer J. Absorption kinetics and action profiles of mixtures of short- and intermediate-acting insulins. Diabetologia. 1984; 27(6):558-62.

120. Lepore M, Pampanelli S, Fanelli C, Porcellati F, Bartocci L, Di Vincenzo A, Cordoni C, Costa E, Brunetti P, Bolli G B. Pharmacokinetics and pharmacodynamics of subcutaneous injection of long-acting human insulin analog glargine, NPH insulin, and ultralente human insulin and continuous subcutaneous infusion of insulin lispro. Diabetes. 2000; 49(12):2142-8.

121. Rosskamp R, Wernicke-Panten K, Draeger E. Clinical profile of the novel sulphonylurea glimepiride. Diabetes Res Clin Pract. 1996; 31 Suppl:S33-42.

122. Kabadi M U, Kabadi U M. Effects of glimepiride on insulin secretion and sensitivity in patients with recently diagnosed type 2 diabetes mellitus. Clin Ther. 2004; 26(1):63-9.

123. Natali A, Toschi E, Camastra S, Gastaldelli A, Groop L, Ferrannini E. Determinants of postabsorptive endogenous glucose output in non-diabetic subjects. European Group for the Study of Insulin Resistance (EGIR). Diabetologia. 2000; 43(10):1266-72.

124. Hotamisligil G S, Shargill N S, Spiegelman B M. Adipose expression of tumor necrosis factor-alpha: direct role in obesity-linked insulin resistance. Science. 1993; 259(5091):87-91.

125. Yudkin J S, Stehouwer C D, Emeis J J, Coppack S W. C-reactive protein in healthy subjects: associations with obesity, insulin resistance, and endothelial dysfunction: a potential role for cytokines originating from adipose tissue? Arterioscler Thromb Vasc Biol. 1999; 19(4):972-8.

126. Mohamed-Ali V, Goodrick S, Rawesh A, Katz D R, Miles J M, Yudkin J S, Klein S, Coppack S W. Subcutaneous adipose tissue releases interleukin-6, but not tumor necrosis factor-alpha, in vivo. J Clin Endocrinol Metab. 1997; 82(12):4196-200.

127. Lundgren C H, Brown S L, Nordt T K, Sobel B E, Fujii S. Elaboration of type-1 plasminogen activator inhibitor from adipocytes. A potential pathogenetic link between obesity and cardiovascular disease. Circulation. 1996; 93(1):106-10.

128. Dandona P, Aljada A, Mohanty P, Ghanim H, Hamouda W, Assian E, Ahmad S. Insulin inhibits intranuclear nuclear factor kappaB and stimulates IkappaB in mononuclear cells in obese subjects: evidence for an anti-inflammatory effect? J Clin Endocrinol Metab. 2001; 86(7):3257-65.

129. Aljada A, Ghanim H, Mohanty P, Kapur N, Dandona P. Insulin inhibits the pro-inflammatory transcription factor early growth response gene-1 (Egr)-1 expression in mononuclear cells (MNC) and reduces plasma tissue factor (TF) and plasminogen activator inhibitor-1 (PAI-1) concentrations. J Clin Endocrinol Metab. 2002; 87(3):1419-22.

130. Dandona P, Aljada A, Bandyopadhyay A. Inflammation: the link between insulin resistance, obesity and diabetes. Trends Immunol. 2004; 25(1):4-7.

131. Crook M A, Tutt P, Pickup J C. Elevated serum sialic acid concentration in NIDDM and its relationship to blood pressure and retinopathy. Diabetes Care. 1993; 16(1):57-60.

132. Pickup J C, Mattock M B, Chusney G D, Burt D. NIDDM as a disease of the innate immune system: association of acute-phase reactants and interleukin-6 with metabolic syndrome X. Diabetologia. 1997; 40(11):1286-92.

133. Schmidt M I, Duncan B B, Sharrett A R, Lindberg G, Savage P J, Offenbacher S, Azambuja M I, Tracy R P, Heiss G. Markers of inflammation and prediction of diabetes mellitus in adults (Atherosclerosis Risk in Communities study): a cohort study. Lancet. 1999; 353(9165): 1649-52.

134. Duncan B B, Schmidt M I, Pankow J S, Ballantyne C M, Couper D, Vigo A, Hoogeveen R, Folsom A R, Heiss G, Atherosclerosis Risk in Communities Study. Low-grade systemic inflammation and the development of type 2 diabetes: the atherosclerosis risk in communities study. Diabetes. 2003; 52(7):1799-805.

135. Duncan B B, Schmidt M I, Chambless L E, Folsom A R, Carpenter M, Heiss G. Fibrinogen, other putative markers of inflammation, and weight gain in middle-aged adults—the ARIC study. Atherosclerosis Risk in Communities. Obes Res. 2000; 8(4):279-86.

136. Pradhan A D, Manson J E, Rifai N, Buring J E, Ridker P M. C-reactive protein, interleukin 6, and risk of developing type 2 diabetes mellitus. JAMA. 2001; 286(3):327-34.

137. Barzilay J I, Abraham L, Heckbert S R, Cushman M, Kuller L H, Resnick H E, Tracy R P. The relation of markers of inflammation to the development of glucose disorders in the elderly: the Cardiovascular Health Study. Diabetes. 2001; 50(10):2384-9.

138. Han T S, Sattar N, Williams K, Gonzalez-Villalpando C, Lean M E, Haffner S M. Prospective study of C-reactive protein in relation to the development of diabetes and metabolic syndrome in the Mexico City Diabetes Study. Diabetes Care. 2002; 25(11):2016-21.

139. Pradhan A D, Cook N R, Buring J E, Manson J E, Ridker P M. C-reactive protein is independently associated with fasting insulin in nondiabetic women. Arterioscler Thromb Vasc Biol. 2003; 23(4):650-5.

Example 2

This Example illustrates that, in accordance with the method of the invention, patients managed on the glucose supply side would have fewer cardiovascular events versus those managed on the insulin demand side. In order to test this, the electronic medical records of a group model health maintenance organization were queried to compile a population of patients meeting the following inclusion criteria: (i) T2D; (ii) known date of T2D diagnosis; (iii) ICD-9 or CPT code identification and chart review confirmation of a first major cardiovascular event (myocardial infarction, coronary artery bypass graft, or angioplasty); (iv) 5 years of continuous eligibility, and (v) on antidiabetic therapy at the beginning of the 5-year observation period. These patients were subsequently matched (1:1) to T2D patients meeting the same criteria that had not experienced an event and analyzed for differences in glucose control ($HbA_1C$), the glucose: insulin supply dynamic (SD ratio), and categorical combinations of both parameters.

To help explain the situation where long-term, cardiovascular outcome trials have resulted in counterintuitive outcomes, we have in Example 1 presented data for a pharmacokinetic/pharmacodynamic model that characterizes the effect of conventional antidiabetic therapies on the glucose supply and insulin demand dynamics. To determine if pharmacotherapeutic strategies that favor the glucose supply or insulin demand dynamic are associated with cardiovascular benefit, we retrospectively identified patients with 5-years of eligibility prior to experiencing an initial event, matched them to patients not experiencing an event, and assessed the impact of the glucose supply:insulin demand (SD) ratio in conjunction with measured glucose control (HbA1c).

Methods.

The supporting literature and methods used to calculate the SD ratio for each of the antidiabetic agents included in this Example was described in Example 1. In this Example, to test whether patients managed on the glucose supply side would have fewer cardiovascular events versus those managed on the insulin demand side, the electronic medical records of a group model health maintenance organization were queried. From the electronic medical record, de-identified health care claims, medical progress notes, and laboratory data with dates of service spanning Jan. 1, 1997, and Dec. 31, 2008, were reviewed to compile a population of patients meeting the following inclusion criteria: (i) T2D; (ii) known date of T2D diagnosis; (iii) ICD-9 or CPT code identification[5,6] and chart review confirmation of a first major cardiovascular event (myocardial infarction, coronary artery bypass graft, or angioplasty); (iv) 5 years of continuous eligibility, including medical and prescription claims, preceding the initial cardiovascular event; and (v) on antidiabetic therapy at the beginning of the 5-year observation period. From the database of 194,268 patients, an initial query identified 16,007 patients (8.2%) to have ICD-9 code 250 in their medical claims history. Of these, 15,349 (95.9%) were confirmed to have a diagnosis of T2D and 11,751 to have a diagnosis date referenced in their medical history. Within the group of patients with T2D and a known date of diagnosis, 1107 had an initial event, and 50 met the final inclusion parameters of 5 years of continuous medical and prescription claims preceding the event and presence of antidiabetic therapy at the index date. These patients were subsequently matched (1:1) to T2D patients meeting the same criteria that had not experienced an event. Primary baseline matching criteria included age, gender, T2D duration, BMI, and HbA1c. Secondary matching criteria included a composite profile of blood pressure (systolic, diastolic) and cholesterol [low-density lipoprotein, high-density lipoprotein, triglycerides (TG)]. All baseline values were determined, as an average, from the first 6 months of the 5-year observation period. The University at Buffalo's Health Sciences Institutional Review Board previously approved the de-identified database for exempt status; informed consent was not required.

Based on the evidence presented in the aforementioned cardiovascular outcome trials in the T2D population, it was not anticipated that average HbA1c or categorical HbA1c breakpoints would be independently associated with a reduction in cardiovascular outcomes. Similarly, because the SD ratio is a measure of the pharmacologic impact on glucose supply and insulin demand dynamics, it was not anticipated that the average SD ratio or categorical SD ratio breakpoints would be independently associated with a reduction in events. However, we reasoned that combing the optimal SD ratio breakpoint that minimized event rate and the ADA-recommended HbA1c breakpoint (7%) would realize the greatest cardiovascular benefit. Therefore, in addition to evaluating the associations of mean HbA1c, categorical HbA1c (≥7% vs. <7%), mean SD ratio, and categorical SD ratios (≥1, ≥1.25, ≥1.5) with cardiovascular events, we determined the optimal SD ratio breakpoint that minimized event rate, coupled the breakpoint with the recommended HbA1c threshold (7%), and analyzed the combined parameter for an association with event rate. All statistical assessments of baseline characteristics and cardiovascular outcomes were conducted with the Student's t-test (continuous data) or Chi-square/Fisher's exact test (categorical data).

Results

Application of the Glucose Supply and Insulin Demand Model to Cardiovascular Events. 50 patients with an initial event and known date of occurrence were case matched with noncardiovascular event controls per aforementioned criteria. Baseline characteristics for the event and control patients are presented in Table 2.

TABLE 2

|  | Cardiovascular event | Controls | p value |
| --- | --- | --- | --- |
| Age (years) | 64.6 ± 10.5 | 64.8 ± 11.0 | .926 |
| Gender (male) | 25 | 25 | 1.00 |
| Duration of T2D (years) | 10.6 ± 5.9 | 10.5 ± 3.6 | .885 |
| Weight | 203.5 ± 50.5 | 203.1 ± 46.5 | .972 |
| BMI (kg/m$^2$) | 32.4 ± 7.1 | 32.5 ± 6.4 | .958 |
| Systolic blood pressure (mmHg) | 142.2 ± 14.3 | 145.0 ± 13.5 | .308 |
| Diastolic blood pressure (mmHg) | 81.1 ± 8.6 | 82.4 ± 9.8 | .466 |
| Low-density lipoprotein (mg/dl) | 114.2 ± 29.9 | 117.5 ± 23.6 | .536 |
| High-density lipoprotein (mg/dl) | 43.0 ± 10.9 | 46.4 ± 11.3 | .129 |
| TG (mg/dl) | 288.8 ± 313.1 | 176.0 ± 81.8 | .017 |
| FPG (mg/dl) | 156.7 ± 49.5 | 163.4 ± 51.9 | .510 |
| HbA1c (%) | 7.7 ± 1.4 | 7.5 ± 1.19 | .484 |
| SD Ratio | 1.1 ± 0.3 | 1.2 ± 0.3 | .051 |
| ACEI/ARB (%) | 32.5 ± 43.6 | 47.6 ± 45.2 | .090 |
| Statin (%) | 29.1 ± 40.3 | 41.3 ± 39.5 | .130 |

ACEI = angiotensin converting enzyme inhibitor,
ARB = angiotensin receptor blocking agent,
BMI = body mass index,
FPG = fasting plasma glucose,
HbA1c = hemoglobin A$_1$C,
SD = glucose supply:insulin demand,
TG = triglycerides Age, gender, duration of T2D, and metabolic characteristics were similar between groups, with the exception of TG that were significantly higher in the cardiovascular event cohort (288.8±313.1 mg/dl versus 176.0±81.8 mg/dl; p=0.017). No significant differences in nondiabetes-related therapies were observed between groups, although more control patients tended to be on angiotensin-converting enzyme inhibitors/angiotensin receptor blocking agents (47.6±45.2% vs. 32.5±43.6%; p=0.090) and also to have higher SD ratio values at baseline (1.2±0.3 vs. 1.1±0.3; p=0.051).

Over the course of the 5-year observation period, there was no significant difference observed for the average HbA1c between event patients and controls (7.5±1.0% vs. 7.3±0.9%; p=0.275, respectively). There was also no difference in event rate between the cohorts when patients were categorized at the HbA1c≥7% breakpoint (72% vs. 64%; p=0.391, respectively). Like HbA1c, the mean SD ratio was not significantly different between the cohorts (1.2±0.3 vs. 1.3±0.3; p=0.205, respectively), and there was also no difference in event rate between the cohorts at the ≥1 (68% vs. 76%; p=0.373, respectively), ≥1.25 (42% vs. 56%; p=0.161, respectively), or ≥1.5 (22% vs. 30%; p=0.362) breakpoints.

Figure 5:
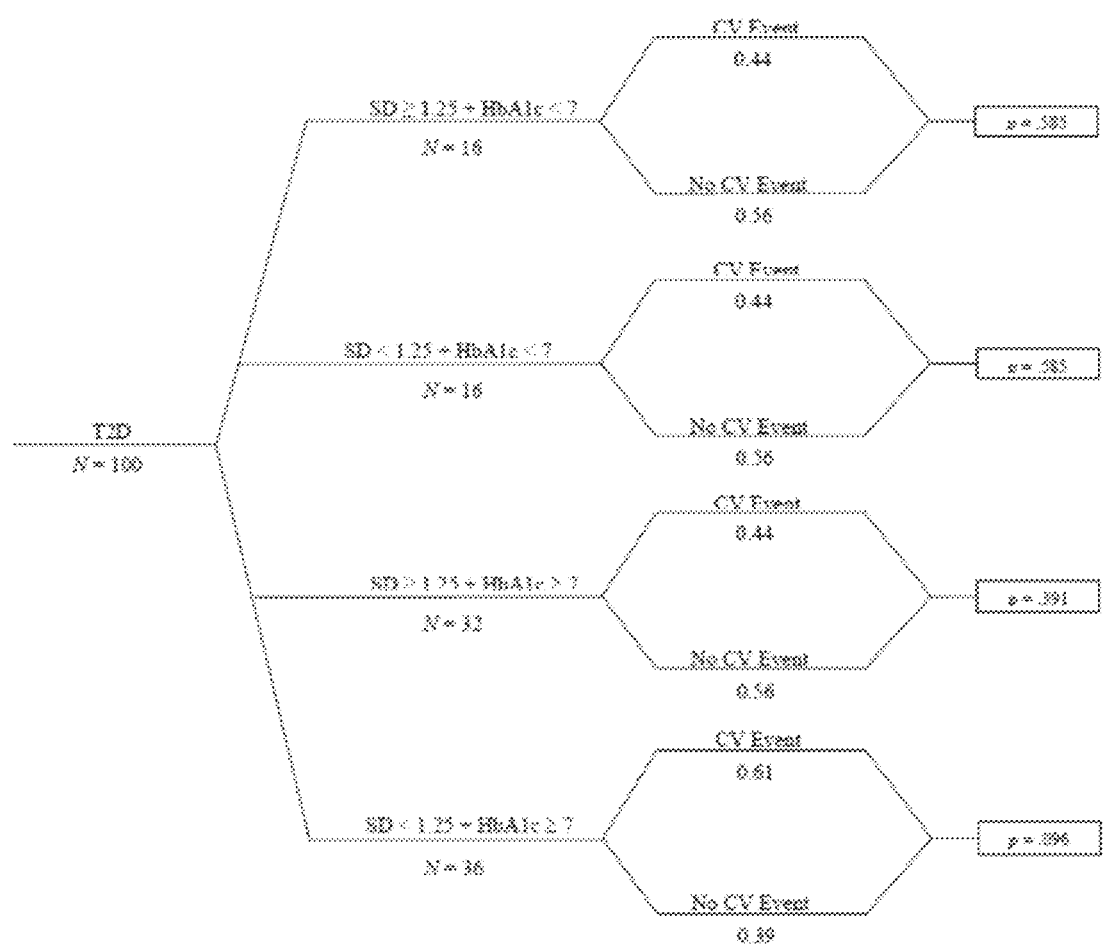
FIG. 5 is a chart illustrating the combined impact of the HbA1c and SD ratio on cardiovascular (CV) event.

We determined that more aggressive HbA1c reduction and higher SD ratio values were not independently associated with a reduction in cardiovascular events. FIG. 5 presents data for the combined impact of the recommended HbA1c breakpoint (<7%) and optimal SD ratio breakpoint (≥1.25) on cardiovascular outcomes. Identical event rates were observed for patients managed to an HbA1c<7% and SD ratio≥1.25, HbA1c<7% and SD ratio<1.25, and HbA1c≥7% and SD ratio≥1.25 (44%). Compared to the remainder of the population, the only group demonstrating a trend toward greater cardiovascular event risk were those managed at higher glucose values and on the insulin demand side of the model (HbA1c≥7% and an SD ratio<1.25; 61% vs. 39%; p=0.096).

As can be seen from the foregoing description, the overwhelming evidence that intensive blood glucose management does not confer a corresponding reduction in macrovascular events requires evaluation of the interventions used to attain the reductions in HbA1c. The impact of pharmacologic intervention has been largely dismissed in the assessment of recent T2D cardiovascular outcome trials.[1-3] Close inspection of therapies utilized during the trials demonstrates a focus on agents that predominantly increase PIE and peripheral glucose disposal. At baseline of the ADVANCE trial, patients in the intensive and standard groups were predominantly on sulfonylurea- (71.8% and 71.1%) and metformin- (61.0% and 60.2%) based regimens with minimal insulin utilization (1.5% and 1.4%). At end of follow-up, sulfonylurea (92.4%) and insulin utilization (40.5%) spiked in the intensive treatment group, while in the standard group, sulfonylurea utilization decreased (58.7%) and insulin use moderately increased (24.1%).[2] Similarly, the ACCORD trial featured greater secretagogue and insulin exposure in those receiving intensive therapy versus standard therapy (86.6% and 73.8% vs. 77.3% and 55.4%, respectively).[1] The VADT determined initial treatment class by BMI, metformin+rosiglitazone when ≥27 kg/m$^2$, glimepiride+rosiglitazone when <27 kg/m$^2$. Subsequently, the intensive management cohort received maximal doses, while standard therapy received one-half the maximal dose.[3] Notably, before any changes in oral medications were made, insulin was added to patients in the intensive management cohort not achieving a HbA1c<6% and only to standard-therapy patients not achieving a HbA1c<9%. Thus, in summary, by analyzing the relationship between cardiovascular events, blood glucose reduction, and the SD ratio, our invention indicates that for patients managed at higher HbA1c values (≥7%), there may be a protective cardiovascular effect if pharmacologically managed on the glucose supply side (SD ratio≥1.25).

References for Example 2

1. Action to Control Cardiovascular Risk in Diabetes Study Group, Gerstein H C, Miller M E, Byington R P, Goff D C Jr, Bigger J T, Buse J B, Cushman W C, Genuth S, Ismail-Beigi F, Grimm R H Jr, Probstfield J L, Simons-Morton D G, Friedewald W T. Effects of intensive glucose lowering in type 2 diabetes. N Engl J Med. 2008; 358 (24):2545-59.
2. ADVANCE Collaborative Group, Patel A, MacMahon S, Chalmers J, Neal B, Billot L, Woodward M, Marre M, Cooper M, Glasziou P, Grobbee D, Hamet P, Harrap S, Heller S, Liu L, Mancia G, Mogensen C E, Pan C, Poulter N, Rodgers A, Williams B, Bompoint S, de Galan B E, Joshi R, Travert F. Intensive blood glucose control and vascular outcomes in patients with type 2 diabetes. N Engl J Med. 2008; 358(24):2560-72.
3. Duckworth W, Abraira C, Moritz T, Reda D, Emanuele N, Reaven P D, Zieve F J, Marks J, Davis S N, Hayward R, Warren S R, Goldman S, McCarren M, Vitek M E, Henderson W G, Huang G D, VADT Investigators. Glucose control and vascular complications in veterans with type 2 diabetes. N Engl J Med. 2009; 360(2):129-39.
4. Editor to Reference for Parent Paper (Manuscript 1)
5. Newton K M, Wagner E H, Ramsey S D, McCulloch D, Evans R, Sandhu N, Davis C. The use of automated data to identify complications and comorbidities of diabetes: a validation study. J Clin Epidemiol. 1999; 52(3):199-207.
6. Pladevall M, Goff D C, Nichaman M Z, Chan F, Ramsey D, Ortiz C, Labarthe D R. An assessment of the validity of ICD Code 410 to identify hospital admissions for myocardial infarction: The Corpus Christi Heart Project. Int J Epidemiol. 1996; 25(5):948-52.
7. Bays H E, Goldberg R B. The 'forgotten' bile acid sequestrants: is now a good time to remember? Am J Ther. 2007; 14(6):567-80.
8. Stulnig T M, Oppermann U, Steffensen K R, Schuster G U, Gustafsson J A. Liver X receptors downregulate 11beta-hydroxysteroid dehydrogenase type 1 expression and activity. Diabetes. 2002; 51(8):2426-33.
9. Cao G, Liang Y, Broderick C L, Oldham B A, Beyer T P, Schmidt R J, Zhang Y, Stayrook K R, Suen C, Otto K A, Miller A R, Dai J, Foxworthy P, Gao H, Ryan T P, Jiang X C, Burris T P, Eacho P I, Etgen G J. Antidiabetic action of a liver x receptor agonist mediated by inhibition of hepatic gluconeogenesis. J Biol Chem. 2003; 278(2): 1131-6.
10. Laffitte B A, Chao L C, Li J, Walczak R, Hummasti S, Joseph S B, Castrillo A, Wilpitz D C, Mangelsdorf D J, Collins J L, Saez E, Tontonoz P. Activation of liver X receptor improves glucose tolerance through coordinate regulation of glucose metabolism in liver and adipose tissue. Proc Natl Acad Sci USA. 2003; 100(9):5419-24.
11. Efanov A M, Sewing S, Bokvist K, Gromada J. Liver X receptor activation stimulates insulin secretion via modulation of glucose and lipid metabolism in pancreatic beta-cells. Diabetes. 2004; 53 Suppl 3:S75-8.
12. Ma K, Saha P K, Chan L, Moore D D. Farnesoid X receptor is essential for normal glucose homeostasis. J Clin Invest. 2006; 116(4):1102-9.
13. Mitro N, Mak P A, Vargas L, Godio C, Hampton E, Molteni V, Kreusch A, Saez E. The nuclear receptor LXR is a glucose sensor. Nature. 2007; 445(7124):219-23.
14. Thomson A B, Keelan M. Feeding rats diets containing cheno- or ursodeoxycholic acid or cholestyramine modifies intestinal uptake of glucose and lipids. Digestion. 1987; 38(3):160-70.
15. Feldman E B, Watt R, Feldman D S. Conjugated dihydroxy bile salt inhibition of glucose influx in rat jejunum in vitro. Am J Dig Dis. 1977; 22(5):415-8.
16. Kogire M, Gomez G, Uchida T, Ishizuka J, Greeley G H Jr, Thompson J C. Chronic effect of oral cholestyramine, a bile salt sequestrant, and exogenous cholecystokinin on insulin release in rats. Pancreas. 1992; 7(1):15-20.
17. Brand S J, Morgan R G. Stimulation of pancreatic secretion and growth in the rat after feeding cholestyramine Gastroenterology. 1982; 83(4):851-9.
18. Koide M, Okabayashi Y, Otsuki M. Role of endogenous bile on basal and postprandial CCK release in humans. Dig Dis Sci. 1993; 38(7):1284-90.
19. Gomez G, Upp J R Jr, Lluis F, Alexander R W, Poston G J, Greeley G H Jr, Thompson J C. Regulation of the release of cholecystokinin by bile salts in dogs and humans. Gastroenterology. 1988; 94(4):1036-46.
20. Katsuma S, Hirasawa A, Tsujimoto G. Bile acids promote glucagon-like peptide-1 secretion through TGR5 in a murine enteroendocrine cell line STC-1. Biochem Biophys Res Commun 2005; 329(1):386-90.

21. Inoue Y, Yu A M, Yim S H, Ma X, Krausz K W, Inoue J, Xiang C C, Brownstein M J, Eggertsen G, Björkhem I, Gonzalez F J. Regulation of bile acid biosynthesis by hepatocyte nuclear factor 4alpha. J Lipid Res. 2006; 47(1):215-27.
22. De Fabiani E, Mitro N, Gilardi F, Caruso D, Galli G, Crestani M. Coordinated control of cholesterol catabolism to bile acids and of gluconeogenesis via a novel mechanism of transcription regulation linked to the fasted-to-fed cycle. J Biol Chem. 2003; 278(40):39124-32.
23. Bays H E, Cohen D E. Rationale and design of a prospective clinical trial program to evaluate the glucose-lowering effects of colesevelam HCl in patients with type 2 diabetes mellitus. Curr Med Res Opin. 2007; 23(7): 1673-84.
24. Gustafsson B E, Angelin B, Einarsson K, Gustafsson J A. Influence of cholestyramine on synthesis of cholesterol and bile acids in germfree rats. J Lipid Res. 1978; 19(8):972-7.
25. DeFronzo R A, Okerson T, Viswanathan P, Guan X, Holcombe J H, MacConell L. Effects of exenatide versus sitagliptin on postprandial glucose, insulin and glucagon secretion, gastric emptying, and caloric intake: a randomized, cross-over study. Curr Med Res Opin. 2008; 24(10): 2943-52.
26. Scott K A, Moran T H. The GLP-1 agonist exendin-4 reduces food intake in nonhuman primates through changes in meal size. Am J Physiol Regul Integr Comp Physiol. 2007; 293(3):R983-7.
27. Edwards C M, Stanley S A, Davis R, Brynes A E, Frost G S, Seal L J, Ghatei M A, Bloom S R. Exendin-4 reduces fasting and postprandial glucose and decreases energy intake in healthy volunteers. Am J Physiol Endocrinol Metab. 2001; 281(1):E155-61.
28. Cervera A, Wajcberg E, Triplitt C, Fernandez M, Joya J, Zuo P, DeFronzo R A, Cersosimo E. Different effects of acute vs. chronic exenatide administration on the mechanism of attenuation of post-meal glucose in T2DM. American Diabetes Association 68th Scientific Sessions 2008, Jun. 6-10, 2008, San Francisco, Calif.
29. Cervera A, Wajcberg E, Sriwijitkamol A, Fernandez M, Zuo P, Triplitt C, Musi N, DeFronzo R A, Cersosimo E. Mechanism of action of exenatide to reduce postprandial hyperglycemia in type 2 diabetes. Am J Physiol Endocrinol Metab. 2008; 294(5):E846-52.
30. Kolterman O G, Buse J B, Fineman M S, Gaines E, Heintz S, Bicsak T A, Taylor K, Kim D, Aisporna M, Wang Y, Baron A D. Synthetic exendin-4 (exenatide) significantly reduces postprandial and fasting plasma glucose in subjects with type 2 diabetes. J Clin Endocrinol Metab. 2003; 88(7):3082-9.
31. Raz I, Hanefeld M, Xu L, Caria C, Williams-Herman D, Khatami H, Sitagliptin Study 023 Group. Efficacy and safety of the dipeptidyl peptidase-4 inhibitor sitagliptin as monotherapy in patients with type 2 diabetes mellitus. Diabetologia. 2006; 49(11):2564-71.
32. Chapman I, Parker B, Doran S, Feinle-Bisset C, Wishart J, Strobel S, Wang Y, Burns C, Lush C, Weyer C, Horowitz M. Effect of pramlintide on satiety and food intake in obese subjects and subjects with type 2 diabetes. Diabetologia. 2005; 48(5):838-48.
33. Pullman J, Darsow T, Frias J P. Pramlintide in the management of insulin-using patients with type 2 and type 1 diabetes. Vasc Health Risk Manag. 2006; 2(3):203-12.
34. Hollander P, Maggs D G, Ruggles J A, Fineman M, Shen L, Kolterman O G, Weyer C. Effect of pramlintide on weight in overweight and obese insulin-treated type 2 diabetes patients. Obes Res. 2004; 12(4):661-8.
35. Hollander P, Ratner R, Fineman M, Strobel S, Shen L, Maggs D, Kolterman O, Weyer C. Addition of pramlintide to insulin therapy lowers HbA1c in conjunction with weight loss in patients with type 2 diabetes approaching glycaemic targets. Diabetes Obes Metab. 2003; 5(6):408-14.
36. Hollander P A, Levy P, Fineman M S, Maggs D G, Shen L Z, Strobel S A, Weyer C, Kolterman O G. Pramlintide as an adjunct to insulin therapy improves long-term glycemic and weight control in patients with type 2 diabetes: a 1-year randomized controlled trial. Diabetes Care. 2003; 26(3):784-90.
37. Ratner R E, Want L L, Fineman M S, Velte M J, Ruggles J A, Gottlieb A, Weyer C, Kolterman O G. Adjunctive therapy with the amylin analogue pramlintide leads to a combined improvement in glycemic and weight control in insulin-treated subjects with type 2 diabetes. Diabetes Technol Ther. 2002; 4(1):51-61.
38. Whitehouse F, Kruger D F, Fineman M, Shen L, Ruggles J A, Maggs D G, Weyer C, Kolterman O G. A randomized study and open-label extension evaluating the long-term efficacy of pramlintide as an adjunct to insulin therapy in type 1 diabetes. Diabetes Care. 2002; 25(4):724-30.
39. Vella A, Lee J S, Camilleri M, Szarka L A, Burton D D, Zinsmeister A R, Rizza R A, Klein P D. Effects of pramlintide, an amylin analogue, on gastric emptying in type 1 and 2 diabetes mellitus. Neurogastroenterol Motil. 2002; 14(2):123-31.
40. Kong M F, King P, Macdonald I A, Stubbs T A, Perkins A C, Blackshaw P E, Moyses C, Tattersall R B. Infusion of pramlintide, a human amylin analogue, delays gastric emptying in men with IDDM. Diabetologia. 1997; 40(1): 82-8.
41. Kong M F, Stubbs T A, King P, Macdonald I A, Lambourne J E, Blackshaw P E, Perkins A C, Tattersall R B. The effect of single doses of pramlintide on gastric emptying of two meals in men with IDDM. Diabetologia. 1998; 41(5):577-83.
42. Kong M F, Macdonald I A, Tattersall R B. Gastric emptying in diabetes. Diabet Med. 1996; 13(2):112-9.
43. Kellmeyer T A, Kesty N C, Wang Y, Frias J P, Fineman M S. Pharmacokinetics of an oral drug (acetaminophen) administered at various times relative to subcutaneous injection of pramlintide in subjects with type 2 diabetes. J Clin Pharmacol. 2007; 47(7):798-805.
44. Fineman M, Weyer C, Maggs D G, Strobel S, Kolterman O G. The human amylin analog, pramlintide, reduces postprandial hyperglucagonemia in patients with type 2 diabetes mellitus. Horm Metab Res. 2002; 34(9):504-8.
45. Fineman M S, Koda J E, Shen L Z, Strobel S A, Maggs D G, Weyer C, Kolterman O G. The human amylin analog, pramlintide, corrects postprandial hyperglucagonemia in patients with type 1 diabetes. Metabolism. 2002; 51(5):636-41.
46. Nyholm B, Orskov L, Hove K Y, Gravholt C H, Møller N, Alberti K G, Moyses C, Kolterman O, Schmitz O. The amylin analog pramlintide improves glycemic control and reduces postprandial glucagon concentrations in patients with type 1 diabetes mellitus. Metabolism. 1999; 48(7): 935-41.
47. Ceriello A, Lush C W, Darsow T, Piconi L, Corgnali M, Nanayakkara N, Frias J P, Maggs D. Pramlintide reduced markers of oxidative stress in the postprandial period in patients with type 2 diabetes. Diabetes Metab Res Rev. 2008; 24(2):103-8.

48. Orskov L, Nyholm B, Yde Hove K, Gravholt C H, Møller N, Schmitz O. Effects of the amylin analogue pramlintide on hepatic glucagon responses and intermediary metabolism in type 1 diabetic subjects. Diabet Med. 1999; 16(10):867-74.

Example 3

This Example provides a description and illustrative examples of expected results obtained by implementation of the method of the invention under several exemplary scenarios.

Illustrative Case Example: Baseline Patient Presentation: Patient AB is a 5′8, 94.3 kg (body mass index of 31.6 kg/m²), 53 yo male with new onset type 2 diabetes mellitus (T2D). Upon the advice of his physician ten years ago he quit smoking. At present, he is negative for cardiovascular complications of peripheral arterial disease, coronary artery disease, coronary revascularization procedures, myocardial infarction, or ischemic stroke. Clinical evaluation and consultation reveals that his blood pressure is slightly elevated (138/82 mmHg), his diet is high in fat and carbohydrate, and he does not participate in aerobic activities. Laboratory analysis revealed his hemoglobin $A_1C$ to be 7.2%, LDL cholesterol to be 102 mg/dL, HDL cholesterol to be 42 mg/dL, and triglycerides to be 187 mg/dL. His current medication regimen includes only Lisinopril 10 mg daily and Simvastatin 40 mg at bedtime.

Management Scenario 1: Patient AB is given Insulin Glargine at a dose of 47 units (0.5 units/kg/day) to be administered subcutaneously once daily at bedtime. He returns to the clinic 3-months later with no significant change in his cardiovascular history and his blood pressure (136/84 mmHg), body mass index (31.6 kg/m²), dietary habits, and physical activity habits have not significantly changed. His hemoglobin $A_1C$ has declined to 6.7%, while his LDL cholesterol (104 mg/dL), HDL cholesterol (43 mg/dL), and triglycerides (168 mg/dL) have not significantly changed. His medication regimen now includes the Insulin Glargine 47 units daily, Lisinopril 10 mg daily, and Simvastatin 40 mg at bedtime.

Management Scenario 2: Patient AB is given Metformin at an oral dose of 1,000 mg twice daily. He returns to the clinic 3-months later with no significant change in his cardiovascular history and his blood pressure (136/84 mmHg), body mass index (31.6 kg/m²), dietary habits, and physical activity habits have not significantly changed. His hemoglobin $A_1C$ has declined to 6.7%, while his LDL cholesterol (104 mg/dL), HDL cholesterol (43 mg/dL), and triglycerides (168 mg/dL) have not significantly changed. His medication regimen now includes the Metformin 1,000 mg twice daily, Lisinopril 10 mg daily, and Simvastatin 40 mg at bedtime.

Management Scenario 3: Patient AB elects to undergo Roux-en-Y gastric bypass. He returns to the clinic 3-months later with a hemoglobin $A_1C$ reduction to 6.7% without significant change in his cardiovascular history, blood pressure (136/84 mmHg), LDL cholesterol (104 mg/dL), HDL cholesterol (43 mg/dL), triglycerides (168 mg/dL) or medications. He has lost 22.7 kg reducing his body mass index to 24.0 kg/m². Because of the surgery he can only eat low carb, low fat meals or he gets extremely nauseous and he has yet to start exercising. Supply/Demand Calculations for Antidiabetic Therapeutic Interventions:

Supply/Demand (SD) Calculation for Metformin 2000 mg Daily (Table 3):

TABLE 3

| Category | Score | Supply (1 + (CE + HGU + GNG + IR)) | Demand (1 + (PIE + PGU)) | Ratio (Supply/ Demand) |
|---|---|---|---|---|
| CE | 0.15 | 2.28 | 1.04 | 2.20 |
| HGU | 0.40 | | | |
| HGI | 0.35 | | | |
| IR | 0.38 | | | |
| PIE | −0.10 | | | |
| PGU | 0.14 | | | |

Supply/Demand Calculation for Glyburide 10 mg Daily (Table 4):

TABLE 4

| Category | Score | Supply (1 + (CE + HGU + GNG + IR)) | Demand (1 + (PIE + PGU)) | Ratio (Supply/ Demand) |
|---|---|---|---|---|
| CE | 0.00 | 1.21 | 1.57 | 0.77 |
| HGU | 0.14 | | | |
| HGI | 0.07 | | | |
| IR | 0.00 | | | |
| PIE | 0.21 | | | |
| PGU | 0.36 | | | |

Supply/Demand Calculation for Pioglitazone 45 mg Daily (Table 5):

TABLE 5

| Category | Score | Supply (1 + (CE + HGU + GNG + IR)) | Demand (1 + (PIE + PGU)) | Ratio (Supply/ Demand) |
|---|---|---|---|---|
| CE | 0.00 | 1.97 | 1.49 | 1.32 |
| HGU | 0.40 | | | |
| HGI | 0.21 | | | |
| IR | 0.35 | | | |
| PIE | −0.10 | | | |
| PGU | 0.59 | | | |

Supply/Demand Calculation for Insulin Glargine 0.5 U/Kg Daily (Table 6):

TABLE 6

| Category | Score | Supply (1 + (CE + HGU + GNG + IR)) | Demand (1 + (PIE + PGU)) | Ratio (Supply/ Demand) |
|---|---|---|---|---|
| CE | 0.00 | 1.34 | 1.72 | 0.78 |
| HGU | 0.24 | | | |
| HGI | 0.10 | | | |
| IR | 0.00 | | | |
| PIE | 0.30 | | | |
| PGU | 0.42 | | | |

Supply/Demand Calculation for Insulin Glargine 1.0 U/Kg Daily (Table 7):

TABLE 7

| Category | Score | Supply (1 + (CE + HGU + GNG + IR)) | Demand (1 + (PIE + PGU)) | Ratio (Supply/ Demand) |
|---|---|---|---|---|
| CE | 0.00 | 1.68 | 2.44 | 0.69 |
| HGU | 0.48 | | | |
| HGI | 0.20 | | | |
| IR | 0.00 | | | |

TABLE 7-continued

| Category | Score | Supply (1 + (CE + HGU + GNG + IR)) | Demand (1 + (PIE + PGU)) | Ratio (Supply/ Demand) |
|---|---|---|---|---|
| PIE | 0.60 | | | |
| PGU | 0.84 | | | |

Supply/Demand Calculation for Metformin 2000 mg Daily+ Insulin Glargine 0.5 U/Kg Daily (Table 8):

TABLE 8

| Category | Score | Supply (1 + (CE + HGU + GNG + IR)) | Demand (1 + (PIE + PGU)) | Ratio (Supply/ Demand) |
|---|---|---|---|---|
| CE | 0.15 | 2.62 | 1.76 | 1.49 |
| HGU | 0.64 | | | |
| HGI | 0.45 | | | |
| IR | 0.38 | | | |
| PIE | 0.20 | | | |
| PGU | 0.56 | | | |

Supply/Demand Calculation for pH Encapsulated Glucose, 3.0 Grams/Day Between Meals (Table 9):

TABLE 9

| Category | Score | Supply (1 + (CE + HGU + GNG + IR)) | Demand (1 + (PIE + PGU)) | Ratio (Supply/ Demand) |
|---|---|---|---|---|
| CE | 0.45 | 2.85 | 1.00 | 2.85 |
| HGU | 0.75 | | | |
| HGI | 0.45 | | | |
| IR | 0.20 | | | |
| PIE | −0.15 | | | |
| PGU | 0.15 | | | |

Supply/Demand Calculation for Roux-En-Y Gastric Bypass (Table 10):

TABLE 10

| Category | Score | Supply (1 + (CE + HGU + GNG + IR)) | Demand (1 + (PIE + PGU)) | Ratio (Supply/ Demand) |
|---|---|---|---|---|
| CE | 0.75 | 3.80 | 0.80 | 4.75 |
| HGU | 0.85 | | | |
| HGI | 0.75 | | | |
| IR | 0.45 | | | |
| PIE | −0.35 | | | |
| PGU | 0.15 | | | |

Figure 8:
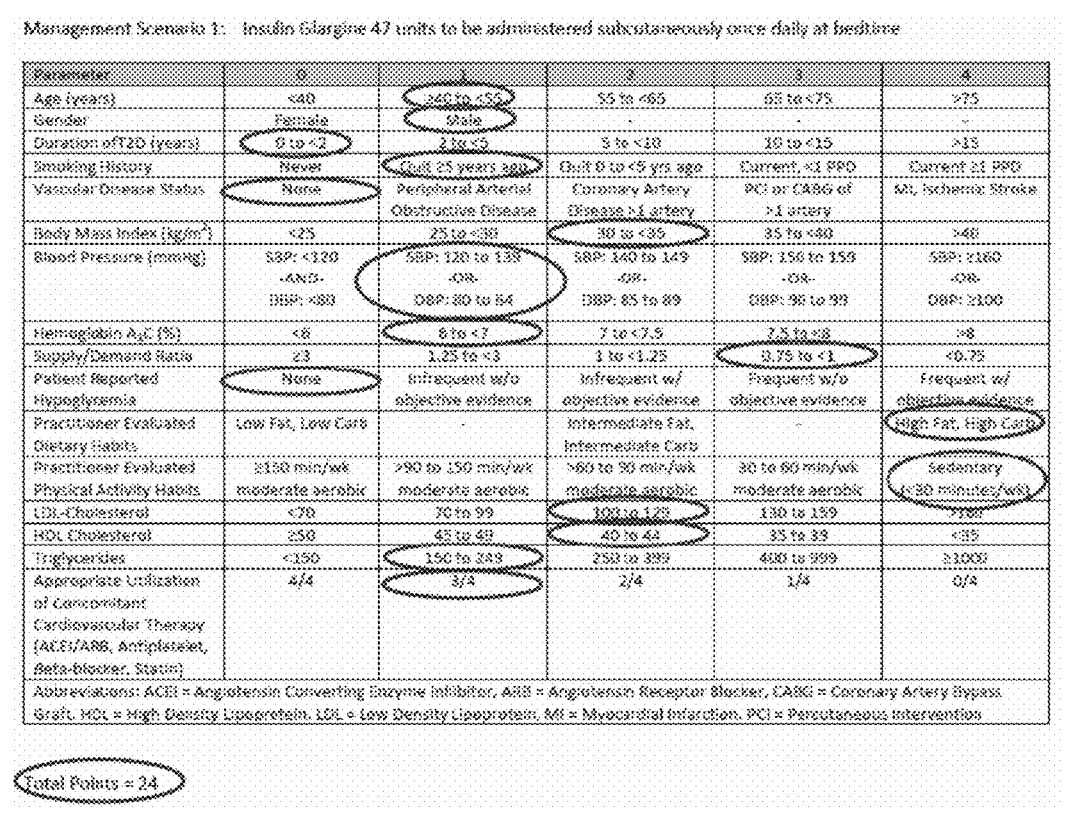

A Risk scoring table for Predicting Macrovascular Events (Myocardial Infarction, Stroke, CV-related Death) in Patients Afflicted with Type 2 Diabetes Mellitus (the Look-Up table) is presented in FIG. 6. Baseline Scoring for Patient AB is presented in FIG. 7. The risk scoring table for Management Scenario 1 (Insulin Glargine 47 units to be administered subcutaneously once daily at bedtime) is presented in FIG. 8. The risk scoring table for Management Scenario 2 (Metformin 1,000 mg orally twice daily) is presented in FIG. 9. The risk scoring table for Management Scenario 3 (Roux-en-Y Gastric Bypass) is presented in FIG. 10.

Case Summary and Rationale for Supply Side Management of T2D:

Pharmacotherapeutic Management Strategies (Scenario 1 and Scenario 2)

In the above case summary three management strategies are presented for example patient AB. In the first management example, utilizing Insulin Glargine at a dose of 47 units daily (0.5 units/kg/day) was able to significantly reduce the hemoglobin $A_1C$, but was not able to diminish the macrovascular event score because of an increase in the Supply/Demand score with all other variables being held constant. Conversely, the Metformin regimen was able to reduce the macrovascular event score at the same level of hemoglobin $A_1C$ lowering because the Supply/Demand score was also reduced while holding all other variables constant. In this particular patient case, there was no occurrence of worsening dietary habits, weight gain, and/or hypoglycemic events that are common with anti-diabetic agents such as Insulin and Secretagogues, but not Amylinomimetics, Alpha-glucosidase Inhibitors, Bile-acid Sequestrants, Dopamine Agonists, DPP-IV inhibitors, GLP-1 agonists, Metformin, and Thiazolidinediones. Therefore, because worsening dietary habits, weight gain, and/or hypoglycemic events would elevate the macrovascular event risk score, it is possible that macrovascular detriment may be seen when administering Insulin and Secretagogue therapy despite an improvement in the hemoglobin $A_1C$. Moreover, this Supply side model of macrovascular disease progression in the T2D patient provides both an explanation for why neutral/poor outcomes were observed in large-scale randomized controlled trials that more aggressively reduced hemoglobin $A_1C$ and also a therapeutic algorithm to maximize the benefit of antidiabetic therapies that lower blood glucose.

Intestinal Glucose Regulation Management Strategies (Scenario 3)

In the remaining management strategy, Roux-en-Y gastric bypass was performed resulting in improved dietary habits and a significant reduction in weight within a 3-month period. Holding all other variables constant (age, gender, T2D duration, smoking history, vascular disease history, blood pressure, hypoglycemia, physical activity, LDL-cholesterol, HDL cholesterol, triglycerides, concomitant cardiovascular therapies) and at the same degree of $HbA_1C$ lowering, the Roux-en-Y gastric bypass procedure was able to most effectively reduce the macrovascular event score because the dietary score (from carbohydrate and fat reductions), body mass index score (from significant weight loss), and the Supply/Demand score (from surgical induced physiologic effects, primarily on the intestine) were all significantly reduced. In this model of macrovascular disease progression in the T2D patient, the Roux-en-Y gastric bypass procedure (and also extending to other bariatric malabsorptive and restrictive procedures) is a non-pharmacologic example that demonstrates macrovascular benefit beyond glucose lowering that is consistent with the teachings of the Supply side management algorithm. The use of pH encapsulated glucose would be expected to yield results similar, but of slightly lesser magnitude to Roux-en-Y gastric bypass because of similar physiologic effects at the level of the intestine. Therefore, in patients that are either unable or unwilling to undergo bariatric surgical intervention, pH encapsulated glucose would serve as a next best treatment approach because it would be expected to demonstrate superior dietary alterations, weight loss, and Supply/Demand dynamics in comparison to all other pharmacologic approaches, but in particular those that would decrease the Supply/Demand ratio and increase the likelihood for continuing poor dietary habits as well as hypoglycemia, weight gain, and physical inactivity (i.e. insulin and secretagogues).

Example 4

This Example provides a description and illustrative examples of expected results obtained by implementation of the method of the invention under several exemplary scenarios, and in particular discloses use of the SD index to calculate the FS index, as well as the use of the FS index in tools for assessment, therapy, monitoring treatment, and treatment of MS. In particular, the invention provides for determination of the FS index of MS and its use in reducing cardiovascular risk associated with it.

This Example provides patient specific calculations of SD and FS indices and demonstrates the invention in terms of therapeutic approaches which improve or resolve metabolic syndrome and lower associated cardiovascular risk. This Example also discloses application of the invention in identifying drug therapies beneficial to the resolution or control of metabolic syndrome, as defined by FS index measurements.

The FS index can be calculated and used in a method for determining cardiovascular risk for an individual suspected of having, at risk for, or diagnosed with MS. The method comprises some or all of the following steps:

a) obtaining from an individual one or more biological parameters, and from the biological parameters:

b) determining the FS index, wherein the FS index is calculated as:

$$\frac{0.11\left[(FBG+TG)+HBA1c\times\frac{HBA1c\times20}{5}+BMI\times\frac{FBG+TG}{150}+AST\times\frac{TG\times4}{100}+FB\text{ insulin}\times(BMI-22)\right]}{S/D\text{ ratio}}$$

wherein the FBG is Fasting Blood Glucose in mg/dl; the TG is Triglycerides in mg/dl; the HBA1c is hemoglobin A1c in %; the BMI is body mass index in kg/m$^2$; AST is Aspartate Transferase in IU/liter; FB insulin is fasting Blood insulin concentration in nmol/liter.

The SD ratio, as explained above, is a ratio of Glucose Supply Index (S) to Insulin Demand Index (D) calculated as follows:

1+[aggregate of carbohydrate exposure (CE)+hepatic glucose uptake (HGU)+hepatic gluconeogenesis (GNG) and +insulin resistance (IR)], and (D) calculated as follows:

1+[aggregate of peripheral glucose uptake (PGU)+ peripheral insulin exposure (PIE)].

The FS ratio results in a numerical value which can be used as an MS assessment tool in a variety of ways. For example, it is considered that an FS index value of greater than 60 indicates that the individual is in need of therapy for MS, or that the individual is at risk for at least one cardiovascular complication associated with MS. As the FS index rises above 250 the cardiovascular (CV) risk is very high, and as it falls to values below 50, and preferably to values as low as 20, the CV risk profile of the patient is greatly improved. In this way the invention provides for therapeutic and/or surgical interventions that are guided by a determination of the FS index. For instance, upon determining an FS index value of greater than 60, the invention in certain embodiments further comprises initiating or modifying a therapeutic approach designed to address MS and/or one of its underlying cardiovascular conditions. In one embodiment, the invention includes administering a drug, alone or in combination with other drugs, to the individual based on a determination of an FS index higher than 60. In a preferred embodiment the drug is pH-encapsulated glucose as described in detail in PCT/US09/005016. This is a form of therapeutic agent which comprises glucose which is formed such that the glucose is released in the intestine at jejunum or ileum at a pH at or above 7.0. Based on studies performed to compare the potency of this formulation of pH encapsulated glucose to patients having RYGB bariatric surgery, this formulation is considered to provide an SD value of 3.5. In another embodiment, the individual is treated with bariatric surgery. Bariatric surgery is considered to provide an SD value of 4.0.

The invention also provides compositions that comprise combinations of pH encapsulated glucose and other, additional anti-diabetes and/or anti-MS drugs. Those skilled in the art, given the benefit of the present disclosure, will recognize that combining such agents according to achieve a more desirable FS index will result in a higher SD ratio. A higher SD ratio accordingly results in a lowering of the FS index, which correlates with improvements in cardiovascular function and a host of other, related beneficial effects, such as prophylaxis and/or therapy of Type 2 diabetes. In certain embodiments, the drug combinations provided by the invention can have an additive, or greater than additive effect on the SD value. In certain embodiments, pH encapsulated glucose is combined with immediate release versions of Metformin, Sitagliptin, statins, insulins, GLP-1 drugs, DPP-IV drugs, Glucokinase activators, DGAT inhibitors, SGLT2 inhibitors or combinations thereof. The formulations can be prepared using any suitable technique, and can be designed to release the active ingredients simultaneously, or sequentially, and can be fast acting or time-release formulations. Additional agents that can be used in drug combinations and/or separately administered to the patient to reduce the cardiovascular risk in metabolic syndrome include but are not necessarily limited to hormones, GLP-1 lipids, proteins, amino-acids, and other sugars or carbohydrates, and combinations thereof.

The invention is suitable for use with individuals who have been diagnosed with MS, or are at risk of developing MS (which can be ascertained by way of the FS index) or who are being treated for MS with at least one drug which may be intended for therapy of MS or any of its individual manifestations. For such patients, a first FS index value can be obtained and the patient can continue treatment with the drug for a period of time, during or after which a second FS index value is determined. A lower second FS value as compared to the first FS index value shows that the drug is effective for treating the MS. However, a higher second FS value relative to the first FS index value is evidence that the individual is in need of a change in dosing of the first drug, or is in need of a change to a different drug, or is a candidate for bariatric surgery, or combinations thereof.

In certain embodiments, the individual for which a first FS index is determined is an individual who is not being treated with pH-encapsulated glucose drug, and wherein a higher second SD ratio value relative to the first SD ratio value is determined. In such cases, the invention provides for initiation of therapy with a pH-encapsulated glucose drug. It will be apparent that this therapy will reduce the FS index because when the SD ratio is increased by the addition of the drug therapy (or by gastric bypass surgery), the SD ratio value increases, which decreases the FS index.

In certain embodiment, at the time the FS index is determined, the individual is not being treated with a Type I diabetes drug or an MS drug, and the SD value is 1.0. As with the SD value, the FS value can be determined using a computer, microprocessor, or a programmable spreadsheet, or combinations thereof.

In certain embodiments, subsequent to administration of the pH-encapsulated glucose alone or in combination with anti-diabetes drugs that together result in a lower SD ratio, severity of one or more of the cardiovascular complications associated with MS is reduced.

The following provides a description of the development and use of the FS index.

Methods:

The FS index of MS comprises the following parameters: Fasting Blood Glucose, Fasting Insulin, HBA1c, BMI, AST, Triglycerides, Glucose Supply-Demand (S/D) index, and in certain cases, Proinsulin. Each parameter was mathematically arranged to increase as MS worsened, and weighted approximately equally in the prediction of MS progression and risk for CV events. The FS index was then applied to well-studied patient populations described in Examples 1-3 using a neural net model. The database used to derive the FS index and test the prediction of lower cardiovascular risk profiles included 50 patients with T2D having AMIs, 50 precisely matched T2D controls without AMIs as described above, 100 patients with RYGB surgery and reversal of MS, 61 patients with T2D given metformin, 12 patients on Metformin and Januvia, 33 patients on metformin and Byetta and 18 patients given Brake therapy for Hepatitis C, T2D, NAFLD, or prediabetes. FS index values were calculated from serial laboratory and clinical data over timeframes ranging between 2 and 10 years. In these patient populations, a normal FS index value is between 20-50. Patients with two or more manifestations of MS and increased CV risk profiles have FS index values above 200. Maximum FS index values are above 500, typical when nearly every MS component is highly abnormal.

Results:

High FS index values predicted CV risk in this patient population, regardless of the specific components of MS that were abnormal. Abnormal and rising FS index values predicted AMI and other MACE events. When MS is studied as the equal weight of its components using the FS index, it is apparent why clinical strategies treating only one component of MS do not remove all risk of CV events. The index also explains why drug therapies that improve one aspect of MS but worsen others may not mitigate CV risk or remove events. Abnormal FS index values subsequently normalized, indicated resolution of each component of MS syndrome, raising the possibility that specific treatments of MS might halt progression or reverse MS entirely. For example, changes in FS index in patients with RYGB surgery were dramatic, taking scores of these patients from above 250 to values below 20 in most cases. FS index responses to oral Brake were similar to RYGB, even though Brake treated patients did not lose as much weight.

There are many isolated laboratory predictors for the presence of individual diseases such as diabetes predicted by HBA1c or fasting blood glucose. Such parameters predict the disease and can be used to monitor the control of the parameter, such as when insulin lowers the blood glucose. Laboratory predictors of diseases are designed to be applied to disease detection over very broad populations of heterogeneous patients. These patients may have complex mixtures of diseases and treatments, and thus a broadly applicable but single parameter index such as "high LDL cholesterol" might separate some of the more obvious high risk atherosclerosis patients who have underlying lipid abnormalities, but not perform well on individuals who might deviate from the core metabolic syndrome model used to derive the index. In the case of the ubiquitous disease Type 2 diabetes, there is obvious increased CV risk on any general index because there is always an element of atherosclerosis, but it was necessary to invent the glucose supply insulin demand (SD) ratio as described above when it became clear that the primary cause of cardiovascular events in type 2 diabetes was an oversupply of refined sugar. SD ratio defines how the sugar overdrive leads to CV risk when interacting with the diabetes drugs taken by the patient. None of the indexes created before SD had considered the primary cause (glucose) nor are any prior indices sensitive to the primary means of cure (Roux-en-Y Gastric Bypass (RYGB) bariatric surgery or ileal delivery of glucose) of Type 2 diabetes. This gap resulted in our development of SD ratio as a means of monitoring the important aspects of type 2 diabetes. Since many of these patients have more than one metabolic syndrome parameter abnormal, the present invention provides an application of the SD ratio to patients who have other metabolic syndrome associated diseases concomitant with diabetes, such as Congestive Heart Failure, fatty Liver disease, Hepatitis C, Chronic Obstructive Pulmonary Disease (COPD), Alzheimer's disease, sepsis and others.

Prior to the priority date of the present application, there was no index which predicts the risk of CV events in metabolic syndrome, and in fact there are still very few researchers that consider all of these diseases to be phenotypic manifestations of an underlying metabolic syndrome pattern of CV progression. In Examples 1-3 of the present application, the S/D ratio described is for CV risk prediction in patients with diabetes, but diabetes is just one of many end organ manifestations of metabolic syndrome, which is too narrow a viewpoint.

The presently provided FS index addresses the common manifestations of MS, each of which has historically been thought to be variably related to CV endpoints. Thus, the presently provided FS index is designed to broadly model the important aspects of metabolic syndrome (weight, triglycerides, liver inflammation, insulin production and SD ratio) and derive CV risk therefrom. There is evidence from RYGB that the present invention can facilitate a reversal of atherosclerosis, and surprisingly it is expected that administration of pH encapsulated glucose will have the same or a similar effect.

We used the FS index in conjunction with neural net models to analyze a broad population of patients for changes in CV risk using the index and clearly show that RYGB surgery (and oral pH encapsulated glucose) lowers CV risk profile of all aspects of metabolic syndrome. Thus, use of the FS index as described herein can result in all of the beneficial aspects of RYGB surgery, and the administration of pharmaceutical compositions comprising pH encapsulated glucose.

In one embodiment, calculation of the FS index is used to define improvement in patient well-being after RYGB or Brake therapy, especially from the standpoint of lowering CV risk, and the associated improvement in functioning of Liver, Pancreas, GI tract, Heart, Lungs and Brain. All of these areas of the body are regenerated by administration of pH encapsulated glucose to the ileal brake.

The consensus definition of Metabolic Syndrome includes five components: Abdominal Obesity (Male>40 in waist, Female>35 inch waist), Elevated Triglycerides (>150), Low HDL Cholesterol (<40 male, <50 female), High blood pressure (>135/85), and Hyperglycemia (FBS>120 or HBA1c>7) (1-14). There are several other variants within the consensus definitions as might be anticipated by a research community that does not consider this all to have a common cause or a common treatment methodology. Use of the FS index in certain embodiments to measure each patient's baseline insulin output and integrating the mass balance effects of diet, food composition, insulin output and weight change, is a preferred method for sorting out the relative impact of diet versus the impact of RYGB on pancreatic function and insulin output in MS and T2D (and is expected to have the same benefit on Type 1 diabetes). Since we can establish the baseline insulin output, we can take better advantage of tools such as metabolic syndrome indices, S/D ratios, and the present FS index, along with specific food component analyses (sugar, CHOs, protein, etc). The end result of these parameters and biomarkers is control of metabolic syndrome, and we are now able to determine the novel impact of the invented indexes on the risk of CV disease.

Without intending to be constrained by theory, it is considered that metabolic syndrome leads to an end organ manifestation such as T2D via a continual supply of immediately available carbohydrates, which drives excessive output of the pancreatic beta cells. Glucose supply driven pancreatic stress in absence of ileal hormone signaled pancreatic repair leads to pancreatic exhaustion, acceleration of insulin resistance, Type 2 diabetes, NAFLD and obesity, all of which are core end-organ manifestations of Glucose Supply Side driven metabolic syndrome.

Occurring in parallel, but heretofore undiscovered, the patient under accelerating glucose load and pancreatic stress has a progressive loss of hormone mediated pancreatic, Liver, GI and other organ repair and regeneration capabilities. The pace of metabolic syndrome damage increases as endogenous repair and regenerate pathways shut down under the increasing load of rapidly absorbed sugars and other refined foods.

Again without intending to be bound by any particular theory, it is considered that glucose, hunger and MS all relate to continued hunger as the driver of glucose supply side driven MS, and there are accelerating hunger signals emitted from the L-cells of the ileum in absence of sufficient supply of distally available carbohydrate to satisfy the needs of the bacterial flora in the ileum, and in fact the L-cells themselves. Alterations of intestinal microflora numbers and species, and their need for nutrition continues to signal hunger to the host by use of L-cell signaling procedures to turn off satiety signals, with the core driver being the demand for nutrition by the organisms. In the absence of carbohydrates and certain lipids at the level of the ileum, the host and host bacterial signal is for continued hunger; the combined signal from absence of these substances in the presence of hungry organisms suppress the ileal hormone output from the L-cells. As the human consumes more and more nutrition, eventually the resulting host over-nutrition spills over to the ileum, removing the bacterial suppression of the ileal hormones and allowing a satiety signal until absence begins the cycle again. In certain conditions such as malabsorption or RYGB surgery, excessive carbohydrates arrive at the ileum and in this case, the signals completely over-ride hunger. Ileal Hormone outputs not only produce satiety but also begin to trigger the endogenous repair of pancreas, liver and GI tract cells. Together, these are the novel "stop and repair" processes that are programmed into our bodies to optimize the balance between ingestion and nutritional needs. As these systems are mainly programmed to satisfy basic needs for nutrition, they are most efficient in a relative lack of glucose as nutrition. Our current excessive nutrient ingestion patterns, especially a growing preference for rapidly absorbed immediate release and duodenally absorbed sugars that deny nutrition to distal intestinal bacteria, create an overdrive of the hunger pathways directly to organ exhaustion and obesity without the benefit of the triggered repair. A simple fix for over-nutrition with rapidly absorbed sugars is to perform RYGB surgery. However, it is less invasive to provide oral formulations of carbohydrates that are directly released at the L-cells in a dose sufficient to trigger the stop and repair processes that protect us from accelerations in metabolic syndrome and obesity. In concert with this, the present invention provides pharmaceutical compositions and methods of regenerating organs and tissues in a patient afflicted with one or more organ or tissue manifestations of glucose supply side associated metabolic syndrome, when the syndrome is accompanied by suppressed regenerating processes and progressively failing organs. A pharmaceutical composition in an effective dosage is provided to an MS patient, which wakes up the dormant ileal brake sensor and initiates renewed hormonal signals to regenerate candidate organs and tissues including but not limited to the pancreas, the liver, the enterocytes of the GI tract and the associated signal transmitting neurons. These actions are controlled by measured biomarkers of both the ileal hormone process and the resolution of metabolic syndrome and organ repair. By way of example, directly regenerating pancreas, liver and gastrointestinal tract functions are specifically described herein and attributed to treatment with a specific pharmaceutical composition.

Serially Measured biomarkers of metabolic syndrome progression or regression, in this case the components of the FS index in patients given Brake or taken to RYGB surgery, demonstrate the successful regeneration of organs, t Once regeneration is accomplished by Brake or RYGB surgery, the regenerated organs then signal the patient, to resume adequate nutrition seeking behavior as directed by restored signals of hunger. Specific actions on organ regeneration are confirmed by measured biomarkers and analysis of the results. Dependent on reserve capabilities of the patient at hand, and depending on composition and administered dosage of the pharmaceutical composition, the present invention relates to dramatic improvement or potential cure of metabolic syndrome manifestations including but not limited to diabetes, hyperlipidemia, atherosclerosis, insulin resistance, hypertension, and obesity.

Specific actions on organ regeneration are confirmed at each stage of treatment by measured biomarkers and FS index calculation, and analysis of the results and use of the index to adjust dosage and duration of treatment with the pharmaceutical composition. Dependent on reserve capabilities of the patient at hand, and depending on composition and administered dosage of the pharmaceutical composition, the present invention relates to dramatic improvement or potential cure of metabolic syndrome manifestations including but not limited to diabetes, hyperlipidemia, atherosclerosis, insulin resistance, hypertension, and obesity. The FS index demonstrates these effects of said composition to the treating physician and thereby provides a roadmap to the regeneration of organs and tissues and associated lowering of cardiovascular risk.

Graphics Methodology and Display of Parameters Except where specifically noted, standard deviations for each parameter are displayed on the Y axis, as this factor normalizes the different range of parameters for visual illustration of behavior patterns in groups on a common Y axis. Unless otherwise noted, the X-axis displays time throughout this report.

Neural Net Models and Data Display Methods. The initial association of biomarker-mortality response surface was confirmed and extended by performing subset analyses to identify the most informative input biomarkers on cardiovascular events and outcomes. Throughout this description of the invention, raw data from each patient are displayed vs. time, and cumulative graphics are either displayed or otherwise in our possession. Unless otherwise stated, standard deviations (z-score) vs. time are presented in the individual and mean population graphics.

For purposes of analysis, clinical and laboratory parameters were converted into modified z-scores as follows:

A mean normal value (described as "mean" in the following) was selected based on review of literature and various published laboratory compendia. The Standard Deviation (SD) of each parameter was set to one half of the normal range. The modified z-score is calculated as follows:

$$z = (\text{Patient value} - \text{"mean"})/SD$$

On the graphs, the z-score is reported as the number of SD.

For data discussed below, the "mean" and standard deviations are provided for selected parameters.

Laboratory Biomarkers

Laboratory blood tests collected serially on the FS index model development population included the following:

Complete Blood Count (Hemoglobin, Hematocrit, WBC, differential, platelet count)

Serum Chemistry (Na, K, Cl, glucose, Calcium, BUN, Creatinine, ALT, AST, Alkaline Phosphatase, Lactate Dehydrogenase, total bilirubin)

Coagulation: PT, INR, fibrinogen, platelet count

For each study patient, we had complete access to all raw data, measured vital signs, culture results, and clinician assessments. Many of these measures were incorporated as inputs into the neural net models, and are also illustrated on the Y axis as standard deviations above the defined normal mean of the parameter. The primary aim of the neural net modeling effort was to model CV events and CV mortality in relation to time course of Input parameters, with a second primary effort to model time course of organ failure as a metric in relation to Input factors such as those in the laboratory biomarkers listed above.

Concomitant Diabetes in Metabolic Syndrome Patients: S/D Ratio and CV Events

Examples 1-3 present a T2D disease progression model that characterizes the effect of conventional antidiabetic therapies on the glucose supply and insulin demand dynamic that defines metabolic syndrome associated T2D, and links this S/D index to cardiovascular risk specific to the treatment of T2D patients.

For microvascular outcomes, there is compelling historical and contemporary evidence for intensive blood glucose reduction in patients with either T1D or T2D. There is also strong evidence to support macrovascular benefit with intensive blood glucose reduction in T1D. Similar evidence remains elusive for T2D. Because cardiovascular outcome trials utilizing conventional algorithms to attain intensive blood glucose reduction have not demonstrated superiority to less aggressive blood glucose reduction, it should be considered that the means by which the blood glucose is reduced may be as important as the actual blood glucose.

SD ratio derivation, testing methods: By identifying quantitative differences between antidiabetic agents on carbohydrate exposure (CE), hepatic glucose uptake (HGU), hepatic gluconeogenesis (GNG), insulin resistance (IR), peripheral glucose uptake (PGU), and peripheral insulin exposure (PIE), we created a pharmacokinetic/pharmacodynamic model to characterize the effect of the agents on the glucose supply and insulin demand dynamic. Glucose supply was defined as the cumulative percentage decrease in CE, increase in HGU, decrease in GNG, and decrease in IR, while insulin demand was defined as the cumulative percentage increase in PIE and PGU. With the glucose supply and insulin demand effects of each antidiabetic agent summated, the glucose supply (numerator) was divided by the insulin demand (denominator) to create a value representative of the glucose supply and insulin demand dynamic (SD ratio). Alpha-glucosidase inhibitors (1.25), metformin (2.20), and thiazolidinediones (TZDs; 1.25-1.32) demonstrate a greater effect on glucose supply (SD ratio>1), while secretagogues (0.69-0.81), basal insulin (0.77-0.79), and bolus insulin (0.62-0.67) demonstrate a greater effect on insulin demand (SD ratio<1). From these studies we conclude that Alpha-glucosidase inhibitors, metformin, and TZDs demonstrate a greater effect on glucose supply, while secretagogues, basal insulin, and bolus insulin demonstrate a greater effect on insulin demand. Because T2D cardiovascular outcome trials have not demonstrated macrovascular benefit with more aggressive blood glucose reduction when using conventional algorithms that predominantly focus on insulin demand, it would appear logical to consider a model that incorporates both the extent of blood glucose lowering as HBA1c and the means by which the blood glucose was reduced (SD ratio) when considering macrovascular outcomes.

It was our objective to test the hypothesis that, in conjunction with HBA1c, patients managed on the glucose supply side of the model would have fewer CV events versus those managed on the insulin demand side. To test this hypothesis, the electronic medical records of a group model health maintenance organization were queried to compile a population of patients meeting the following inclusion criteria: (1) type 2 diabetes mellitus T2D, (2) known date of T2D diagnosis; (3) ICD-9 or CPT code identification and chart review confirmation of a first major cardiovascular event (myocardial infarction, coronary artery bypass graft, or angioplasty), (4) five years of continuous eligibility, and (5) on antidiabetic therapy at the beginning of the 5-year observation period. These patients were subsequently matched (1:1) to T2D patients meeting the same criteria who had not experienced an event and were analyzed for differences in glucose control (HbA1C), the glucose supply: insulin demand dynamic (SD ratio), and categorical combinations of both parameters. RESULTS: Fifty cardiovascular event patients met inclusion criteria and were matched to controls. No difference was observed for the average HbA1c or SD ratio between patients experiencing an event and controls (7.5+/−1.0% versus 7.3+/−0.9%, p=0.275, and 1.2+/−0.3 versus 1.3+/−0.3, p=0.205, respectively). Likewise, for categorical representations, there were no differences in event rate at the pre-identified breakpoints (HbA1c>or=7% versus <7%; 72% versus 64%, p=0.391, and SD ratio>or=1 versus <1; 68% versus 76%, p=0.373, >or=1.25 versus <1.25; 42% versus 56%, p=0.161, >or=1.5 versus <1.5; 22% versus 30%, p=0.362, respectively). Analyzing the combined effect of glucose control and the SD dynamic, patients managed at higher glucose values and on the insulin demand side of the model (HbA1c>or=7% and SD ratio<1.25) tended to have greater cardiovascular risk than those managed at an HbA1c<7%, or HbA1c>or=7% with an SD ratio>or=1.25 (61% versus 39%; p=0.096). Independently, more aggressive HBA1c reduction and higher SD ratio values were not independently associated with a reduction in cardiovascular outcomes. Combining the parameters, it would appear that patients managed at higher glucose values and on the insulin demand side of the model may have increased cardiovascular risk.

FS Index of Metabolic Syndrome: Risk Factors for Cardiovascular Events

We tested the hypothesis that, in conjunction with HBA1c, patients managed on the glucose supply side of the model would have fewer CV events versus those managed on the insulin demand side. As a test of this hypothesis, the electronic medical records of a group model health maintenance organization were queried to compile a population of patients meeting the following inclusion criteria: (1) T2D, (2) known date of T2D diagnosis; (3) ICD-9 or CPT code identification and chart review confirmation of a first major cardiovascular event (myocardial infarction, coronary artery bypass graft, or angioplasty), (4) five years of continuous eligibility and serial monitoring of FS index component parameters, and (5) on antidiabetic therapy at the beginning of the 5-year observation period. These patients were subsequently matched (1:1) to T2D patients meeting the same criteria who had not experienced an event and were analyzed for differences in glucose control (using HBA1C), the glucose supply:insulin demand dynamic (using SD ratio), and categorical combinations of both parameters. Fifty cardiovascular event patients met inclusion criteria and were matched to controls. No difference was observed for the average HBA1c or SD ratio between patients experiencing an event and controls (7.5+/−1.0% versus 7.3+/−0.9%, p=0.275, and 1.2+/−0.3 versus 1.3+/−0.3, p=0.205, respectively). Analyzing the combined effect of glucose control and the SD dynamic, patients managed at higher glucose values and on the insulin demand side of the model (HBA1c>or=7% and SD ratio<1.25) tended to have greater cardiovascular risk than those managed at an HBA1c<7%, or HBA1c>or=7% with an SD ratio>or=1.25 (61% versus 39%; p=0.096). Independently, more aggressive HBA1c reduction and higher SD ratio values were not independently associated with a reduction in cardiovascular outcomes. Combining the parameters, it would appear that patients managed at higher glucose values and on the insulin demand side of the model may have increased cardiovascular risk. (15, 16)

We have extended this concept from the T2D-centric HBA1c-SD parameter described in Examples 1-3 to create the FS index as a global index of metabolic syndrome, thus providing a quantitative means of describing progression of MS in Patients. The FS index is meant in certain embodiments to track the beneficial changes in metabolic syndrome as it is managed by RYGB or by Brake, in turn a link to measurement of regeneration in the systems affected by the underlying common metabolic syndrome of these patients.

As underlying Metabolic Syndrome has many different manifestations in addition to those considered reflective of T2D, the FS index includes hyperlipidemia, obesity and NAFLD, in order to facilitate tracking progression of MS in patient populations that may have any or all of these conditions to varying degree. As one non-limiting example of the utility of why FS, it is known that antidiabetic drugs lower glucose but raise lipids or BP, and thus the net effect is to worsen the Metabolic Syndrome and increase CV risk. It was our hypothesis that improved risk scoring could be accomplished via an index that considered a composite of Metabolic Syndrome system components.

The FS index considered the following: Fasting Blood Glucose, Fasting Insulin, HBA1c, BMI, AST, Triglycerides, Glucose Supply-Demand (S/D) index, and in some cases Proinsulin. As proinsulin was not available to us in datasets used herein, the index was used without considering these data. Each of these parameters was mathematically arranged to increase as Metabolic Syndrome worsened, and weighted approximately equally in the prediction of Metabolic Syndrome progression and risk for CV events.

The FS index was then applied to well-studied patient populations using a neural net model.

Patient Populations

The study is a comprehensive analysis of a large managed care population of metabolic syndrome patients, wherein we have obtained use of long term data from 194,000 patients that have been followed for up to 20 years. The database contains a large amount of information per patient that is routinely collected in clinical practice and hospitals. We also have complete electronic medical records of 100,000 patients who are hospital inpatients in Western NY, and these cases sometimes include the complete hospitalization records of the Managed care population with metabolic syndrome. Throughout these electronic records, we have refills of each prescription coded to NDC number, so all patients can be tracked for adherence to therapy on a long term basis. It is important to point out that the data had to be extracted and tabulated to be specific to the purposes of this study, and that required data analyst time and considerable amounts of medical review. Thus the first study task was to create a metabolic syndrome subset from the available electronic medical records of all these patients.

Each metabolic syndrome patient and applicable controls was characterized in relationship to all treatments and pharmaceuticals given over the entire period of monitoring. Each patient also had adequate records to characterize long term progression of the disease, and a complete record of potential cardiovascular events that can be studied against exposure in a classical time and event progression model. Each patient is examined both separately and as part of subgroups by exposure against each relevant endpoint.

The data analysis leading to an index useful for defining CV events within a patient population with varying degrees of underlying metabolic syndrome becomes a database assembly task and then a comprehensive analysis and mathematical modeling of a large managed care population of metabolic syndrome patients. The data assembly task consists of integration of the data in SQL and then porting the records to MatLab, which is how all of the data in our large Electronic Medical Records database of metabolic syndrome patients is treated after complete de-identification. The end result is common fields and meaningful endpoints for analysis and modeling across the entire dataset.

Structure of Longitudinal Data, Interpolations, Carry-Forwards.

To enable analysis of disparate data (laboratory and clinical) that is not necessarily complete nor synchronous, discrete measurements of each input and output parameter were used to populate continuous longitudinal "waveforms" with a time resolution of 30-90 days. Measurements were placed in the longitudinal "waveform" at the time point corresponding to the date closest the date of the actual measurement (which might be up to 15 days before or after the actual measurement date). If the time delay between subsequent observations was more than 45 days, a 3 step interpolation was used. To generate the time ramp the initial value was used for the first ⅓ of the period between the two observations, the second value for the final ⅓, and a linear interpolation linked those two values. Values prior to the first observation and after the last observation were set to 0 (normal).

Load and Load Metric

Load metric was calculated for known toxins such as cigarettes as, for example the primary driver of lung injury in a load model with an endpoint of COPD, and for FS index as the primary driver of CV and MACE events in metabolic syndrome patients with CV endpoints. Each component parameter of Load was normalized by subtracting the population mean and dividing by a population standard deviation. These normalized metrics were then summated to calculate the Load Metric.

Organ Failure Metric—Example of Component Organ Definitions Used in Models

Organ Failure Metric (OrganMetric or OM) is the primary calculated parameter used to operate the time related progression model with respect to evolution of organ failures. OrganMetric is created by adding together z-scores for individual organ failures; details of this process are listed for each component of the metric in the descriptions below. Higher scores reflect increasing abnormality. Therefore, when an abnormality in a parameter is indicated by negative value, its z-score is subtracted from the OrganMetric to reflect increase in abnormality.

Liver:

Bilirubin total from local laboratory was the primary measure of hepatic function if available, otherwise bilirubin from central lab if available. Normalized (mean 0.7, SD 2.0) and used only values above 0, any values below 0 (normal) were set to 0.

Kidney:

Serum creatinine was the primary measure of renal function. Normalized (mean 0.8, SD 1.0) and used only values above 0, any values below 0 (normal) were set to 0.

Lungs:

Pulmonary abnormalities reflect defects in oxygenation. "LungProduct" was used if available. LungProduct is defined as $(PaO_2/F_iO_2)$/respiratory rate. If ventilator rate was available, it was used instead of respiratory rate. LungProduct was first calculated using actual values of respiratory rate, $F_iO_2$ and/or $PaO_2$ and then normalized (mean 25, SD 5). A negative value of LungProduct reflects pathology; values>0 were set to 0 and the value of LungProduct was subtracted from the composite OrganMetric.

Platelets:

Normalized actual platelet count based on normal values (mean 300, SD 150). In metabolic syndrome the primary platelet abnormality is thrombocytopenia. Therefore the value of this parameter was subtracted when calculating composite OrganMetric.

Blood Pressure and Hypotension:

The database contains numerous systolic and diastolic blood pressure readings, which were displayed as standard deviations from normal values.

Input/Output Considerations—Organ Metric as Representative of Each Metric Used

The OrganMetric was then calculated for every recorded time period using the component parts as described above. Normalization for the number of components was done based on the components that were present at any time in the data set, so as to provide an average metric over the parameters that were available for each patient.

If the "sum" or AUC of the OrganMetric was being used as an input, the hourly components were added for the full duration of the data set. In this manner a patient who had an average organ metric of 2 for 2 days, would have the same AUC as a patient who had an average organ metric of 1 for 4 days.

At the final integration stage of the modeling, the score was normalized by the number of data values that were available from each patient. The final OrganMetric for a patient was the average metric over all organs with available data.

A neural net approach defines a modeling system that can stratify metabolic syndrome into patterns of response, and by so doing can identify an enriched population of individuals who will be specifically responsive to metabolic syndrome therapies based on upon their interactions with biomarkers and drug exposure.

A neural net was used to perform a multiple parameter logistic regression while allowing for non-linear (usually sigmoidal) dependence of responses on input parameters. Candidate input parameters are first used individually to model the desired output and are then ranked based on the error in these single parameter models. A small number (usually 2 or 3 in this project) of the best input parameters are then chosen and used to create the final multi-parametric model which yields a lower modeling error than the original single parameter models.

Model Design

Structural Modeling of complex biological events like metabolic syndrome progression may be problematic due to the incompleteness of the available knowledge about the underlying mechanisms and to the lack of an adequate observational data set. As a novel aspect of the present invention, non-linear approaches to input-output systems such as neural networks offer a valid alternative to classical structural modeling in settings with sparse data. In practice, classical statistical methods, which assume linear dynamics of the system from input-output data, fail when the experimental data set is poor either in size or quality, or the system to be modeled is non-linear or when input-output relationships are offset in time. In the case of metabolic syndrome progression to MACE events, there are many clearly evident nonlinear and time dependent input-output processes. Therefore to overcome this fundamental data management problem, a neural net was used to link input data to desired outputs while allowing for non-linear and time dependent behavior in both input and output functions.

The modeling approach used to produce the present invention is a hybrid approach intended to overcome the problems listed above. The metabolic syndrome variables were modeled with neural networks using MatLab over the time-course of metabolic syndrome progression. All enrolled cases were initially considered candidates for modeling but in some cases there were insufficient data for some parameters to be useful.

Neural networks were used to select informative patient behavior patterns from the overall study population of metabolic syndrome patients followed over a sufficient time-period to identify the link between biomarkers and efficacy of metabolic syndrome treatments in a large fraction of the study population. The enriched population was found by using the neural net to rank order inputs candidates for a given output, the primary output being mortality as affected by treatment (drug or placebo).

Sets (typically two or three) of highly ranked input parameters where then chosen to model the CV events and progression of CV events output. Once a pair of input parameters was chosen, a new neural net model was formed to predict mortality based on this input pair. All analysis and modeling was performed in MatLab.

The neural net model looks for subtle differences in correlations between input parameters and endpoints based on longitudinal data, and can find relationships that are non-linear or that only occur for patients with a certain pattern of parameters. When we have a population of patients (some treated and some not) with a varying degree of drug response, the neural net model was used to identify subpopulations enriched for a response parameter to a drug or a risk parameter from a drug or its absence. We call this process enrichment and it is a novel approach to the analysis of pharmaceutical data that allows greater learning from smaller subsets of patients, amply justifying the size of the database used to develop the FS index and used herein The neural net clearly identifies different response patterns in the cardiovascular risk profile of metabolic syndrome patients.

Because this is a case series and the outcomes are time related endpoints linked to exposure parameters, the statistical analysis approach is based on subgroups (cells) formed from drug exposure categories by actual prescription refill records over time. Thus the data are adjusted in the beginning for patient compliance.

Statistical Plan

Classical statistical analysis of longitudinal data such as the merged databases would employ Kaplan-Meier plots of time vs. a survival function produced from categorical events. Although many of these endpoints of interest in our patients are categorical events, by contrast our analysis methodology placed its emphasis on time to events and most importantly the linkages between cumulative treatment exposure over the disease progression and the time in the disease course that events occur. This approach strengthens the impact of associations between variables, because it converts events to dose response metrics which are inherently more robust in progression modeling. Independent variables become absolute and time related quantitative exposure to a treatment can be precisely measured if background progression in its absence is precisely characterized. This "cumulative exposure per unit of time" approach is better for characterizing disease progression rates and response to timely interventions that are often mixed with times of drug free progression of the disease.

Within each subgroup, there will be sufficient power to assess the impact of cumulative exposure to glucose modified by SD ratio drugs on each of the primary time related endpoints, but in common with statistically driven meta-analysis projects of similar size, this analysis may not be sufficiently powered to assess exposure subgroup differences in overall mortality, even though there were many promising signals with respect to CV events. The same viewpoint is likely true for even attributable mortality, although a robust definition of attributable mortality does improve these types of correlation. Nevertheless, evaluation of these outcomes data generally consists primarily of summary statistics, specifically, estimation of response rates and 95% confidence intervals.

Modifying variables in these analyses are not pre-specified, rather the data are analyzed to derive informative covariates.

Within each exposure cell, a parallel statistical approach is employed, including a multivariate logistic regression model created to determine which co-factors were associated with progression of diabetes to endpoints such as numbers of CV events, mortality and time to adverse events linked to drug therapies. The pool of candidate regressors in the companion statistical models include patient demographics, prior medical conditions, impact of smoking history as pack years, and impact of environmental exposures in the work environment, available biomarkers of inflammation and infection, any prior antibiotic within 90 days. Since the number of candidate regressors in these statistical models are too large even within a relatively large database, the final multivariate statistical model is configured to consider only those variables with $p<0.25$ in an initial bivariate analysis. The Neural Net MatLab model, on the other hand, carries all factors forward without forming subgroups, and defines their relative importance to the endpoints.

Statistical analyses of the data within multiple logistic regression models were then used to link efficacy and biomarkers as population variables to selected outcomes in the informative sub-populations (i.e. the population selected by the enrichment algorithm).

Descriptive statistics were only applied to the data in the tables, primarily using chi square calculations. Demographics were compared with chi-square/Fischer's Exact Test for categorical items and 2-way ANOVA for continuous variables. Clinical response was assessed by chi-square/Fischer's Exact Test.

All statistical tests were run as two-sided with the probability of a Type I error $p<0.05$ considered statistically significant.

Approach to Display of Progression Modeling Results

Outputs of the many runs of the database thru the Neural Net models are presented herein, both in graphical format and tables. In general, we use graphical displays for individual patients and groups of similar patients, and we use tables to present the results of runs of aggregate analyses performed on the individual patients. The general theme of presenting some highlights of the results is outlined as follows:

Input/Output Plots for:
Groups of patients
Subsets of metabolic syndrome patients with common characteristics
Individual patients with top 10 informative parameters displayed over time In each Input/Output graphic, the x axis is time and the y axis is multiples of SD over the normal value which is set at zero. This allows all parameters approximately equal weight in the display, recognizing that parameters behaving in a non-linear fashion will always appear more important in terms of large changes and that display bias cannot be completely removed from the display.

Ranked Correlation Lists for:
diabetes events
CV events
Pharmacoeconomic Analyses
Drug impacts on metabolic syndrome endpoints Tables of rank ordered correlation parameters provided herein are all based on the somewhat time independent link between Inputs (usually the baseline parameter value at time of metabolic syndrome diagnosis) and Outputs calculated as cumulative or AUC variables; the multiples here stated are used to rank order the input in connection to the magnitude of the output, connecting inputs and outputs regardless of timing. Output Error is the Root Mean Squared (RMS) error between the enrichment model based on the input parameter (in this case the baseline biomarker) and the desired output of (for example, CV risk or COPD progression by GLG score), based on each input parameter for all the patients. A lower output error means that the parameter on its own is a better predictor, and the model seeks to find the best single parameter in all cases of RMS rank ordering.

3D Displays Applied to Ranked Correlation Parameters

These displays generally use the top two parameters for a ranked correlation and display them in 3D against a Z axis parameter of defined importance, such as cumulative CV events or cumulative organ failures, etc. In some settings we use a parameter of interest even when it does not achieve "top 2 status" in ranked correlation, simply because it allows the study of the parameter more specifically across the entire population Ordered correlations of Z-axis displays, which position each patients rank and calculate magnitude of differences over null.

These two dimensional graphical displays order the x-axis to start with the patient of lowest risk at zero, and the patient of highest risk at the last value. The y-axis is the risk score itself. Then we use color to define which patients have the event in question. For example, we show increasing risk for CV events on these graphs, and then apply a marking symbol to identify the patients with the actual events vs their risk in an easy to identify display. Calculations of relative risk over zero (the point separating half above and half below) allows an overall estimate of increasing or decreasing probability that roughly follows the more widely applied odds ratio. The advantage of doing the analysis with a neural net is that non-linear behavior is not excessively weighted over linear behavior Tables Aggregating Behavior and Identifying Subsets for Enrichment Studies Final tables aggregating patterns of population behavior are derived from analysis of each individual, once again rank ordering inputs to outputs. In this run of the neural net, the task is to identify the top 2-4 inputs for the particular behavior pattern of interest, such as cardiovascular events as used herein to develop the FS index. The tabulation of these data elements, rank ordered, are then used to define subsets that might be a focus for enrichment studies Summary of Modeling Results (Figures Table Text in the Examples Beyond 00200)

In the art of medicine, physicians consider each of the various aspects of metabolic syndrome to be a single disease, and they use a single lab test to diagnose or monitor treatment progress. An example would be the use of BMI to diagnose or monitor obesity, HBA1c or glucose to diagnose or monitor diabetes, or cholesterol to diagnose or monitor hyperlipidemia. None of these approaches consider direct effects of pharmaceutical treatments, which themselves change the CV risk within each disease, as well as overall. None of these indices consider relative importance if all the aspects are present within each patient, as usually occurs in the art of medicine. None of these single lab test parameters is a useful predictor of cardiovascular events. As we sought an index that would apply to metabolic syndrome and predict the cardiovascular risk therefrom, we initially worked on the diabetes predictor, and that lead to the discovery of the SD ratio, which incorporates a glucose driven approach to diabetes and a CV risk driven partly by how the various treatments alter CV risk within the glucose supply and insulin demand pathway to CV events. On this basis, we were able to improve the art of selecting better drug treatments for diabetes and for the first time provided a novel explanation why RYGB surgery is a better means of lowering CV risk in T2D over any current drug therapy, which is disclosed in Examples 1-3. It is notable that the superior outcomes of bariatric surgery over drug treatment in type 2 diabetes have been published recently, but the authors did not provide any explanation or the mechanism of the superior effects in this paper. Both SD ratio and FS index were invented to explain this mechanistic pathway, and of necessity to invent a new treatment for type 2 diabetes, which is pH encapsulated glucose. As we further examined patients and their CV risk, we then explained diabetes as one aspect of an underlying metabolic syndrome but then realized that we needed to consider all of the other components of metabolic syndrome to fully explain CV risk in patients. Patients with one component of metabolic syndrome such as T2D usually have elements of additional components, such as NAFLD, elevated triglycerides, hypertension and others, each of which clearly impacts their CV risk profile. There was heretofore no available index of metabolic syndrome that links each element to cardiovascular risk. Thus it was necessary to invent a metabolic syndrome index which was predictive of CV events overall in patients who had elements of more than one individual component of metabolic syndrome. Thus, we have extended the discovery of CV risk prediction based on the SD ratio beyond the DIABETES-centric HBA1c-SD parameter as shown in Examples 1-3 to create a global index of metabolic syndrome, i.e., the FS index, to provide a quantitative means of describing progression of Metabolic Syndrome in Patients. The FS index has been designed as a means of identifying patients whose CV risk is elevated by any or all components of metabolic syndrome, and measuring benefit when their metabolic syndrome it is managed by RYGB or by the oral RYGB mimetic drug Brake. These latter two approaches to putative cure of metabolic syndrome are thus far the only means of definitively lowering CV risk in patients with one or more "disease" manifestations of their underlying metabolic syndrome. Without intending to be bound by theory, it is considered that the combined teaching of FS index, RYGB and Brake is that there is one primary cause of all of the manifested disease components that are defined as metabolic syndrome, and there is one general approach to lowering this risk and resolving the individual components, which activation of the ileal brake directly via surgery, or orally with Brake, the target defined ileal hormone releasing substance.

As underlying Metabolic Syndrome has many different manifestations in addition to those considered reflective of T2D, the FS index included hyperlipidemia, obesity and NAFLD, in order to facilitate tracking progression of Metabolic Syndrome in patient populations that may have any or all of these conditions to varying degree. We now use tests for each component of Metabolic Syndrome. As one non-limiting examples of why FS index is meaningful, it is known that antidiabetic drugs lower glucose but raise lipids or BP, and thus the net effect is to worsen the Metabolic Syndrome and increase CV risk. It was our hypothesis that improved risk scoring could be accomplished via an index that considered a composite of Metabolic Syndrome system components. This lead to the discovery of the beneficial effects of an oral ileal brake hormone releasing substance.

Specific Example A

FS Index as a Measure of Treatment Response to Brake Treatment of Metabolic Syndrome In particular, the present invention generally proceeds when the steps in practice of the invention include the testing the patient for laboratory biomarker patterns, use of the results of testing to calculate the FS index, determining the risk of CV events from the FS index calculation, then personalized treatment to lower the FS index, most preferably by the administration of a pharmaceutical composition targeted to a specific receptor cell in the distal intestine, in a dosage and duration of treatment to lower the FS index of the patient upon repeat measurements. The effect of the medicament on the measured biomarkers demonstrates beneficial properties of the ileal brake hormone releasing substance on the laboratory tests that comprise the FS index. In the ordinary assessment of the precise sequence of hormonally produced events, the patient experiences cessation of hunger. With respect to the sequence of signaling molecules from the ileum, a response to the medicament, there is a wake up stimulation of distal intestinal L-cells that have been quieted by actions of intestinal bacteria or metabolic disease; there is a release of hormones and signals from said L-cells; said released hormones traveling in portal blood to pancreas, liver and GI tract, said organs regenerated from available growth factors and hormone signals, measured biomarkers of the FS index demonstrating the successful regeneration and said regenerated organs then signaling the patient, preferably a human, to resume adequate nutrition seeking behavior as directed by restored signals of hunger.

In Examples 1-3 we presented a T2D disease progression model that characterizes the effect of conventional antidiabetic therapies on the glucose supply and insulin demand dynamic that defines metabolic syndrome associated T2D, and links this S/D index to cardiovascular risk specific to the treatment of T2D patients. In this Example, we tested the hypothesis that, in conjunction with HBA1c, patients managed on the glucose supply side of the model would have fewer cardiovascular events versus those managed on the insulin demand side. As a test of this hypothesis, the electronic medical records of a group model health maintenance organization were queried to compile a population of patients meeting the following inclusion criteria: (1) T2D, (2) known date of T2D diagnosis; (3) ICD-9 or CPT code identification and chart review confirmation of a first major cardiovascular event (myocardial infarction, coronary artery bypass graft, or angioplasty), (4) five years of continuous eligibility and serial monitoring of FS index component parameters, and (5) on antidiabetic therapy at the beginning of the 5-year observation period. These patients were subsequently matched (1:1) to T2D patients meeting the same criteria who had not experienced an event and were analyzed for differences in glucose control (using HBA1C), the glucose supply:insulin demand dynamic (using SD ratio), and categorical combinations of both parameters. Fifty cardiovascular event patients met inclusion criteria and were matched to controls. No difference was observed for the average HBA1c or SD ratio between patients experiencing an event and controls (7.5+/−1.0% versus 7.3+/−0.9%, p=0.275, and 1.2+/−0.3 versus 1.3+/−0.3, p=0.205, respectively). Analyzing the combined effect of glucose control and the SD dynamic, patients managed at higher glucose values and on the insulin demand side of the model (HBA1c>or=7% and SD ratio<1.25) tended to have greater cardiovascular risk than those managed at an HBA1c<7%, or HBA1c>or=7% with an SD ratio>or=1.25 (61% versus 39%; p=0.096). Independently, more aggressive HBA1c reduction and higher SD ratio values were not independently associated with a reduction in cardiovascular outcomes. Combining the parameters indicates that patients managed at higher glucose values and on the insulin demand side of the model may have increased cardiovascular risk.

As discussed above, the FS index measures the following: Fasting Blood Glucose, Fasting Insulin, HBA1c, BMI, AST, Triglycerides, Glucose Supply-Demand (S/D) index, and Proinsulin. Each of these parameters was mathematically arranged to increase as Metabolic Syndrome worsened, and weighted approximately equally in the prediction of Metabolic Syndrome progression and risk for CV events.

FS Index Equation:

$$\frac{0.11\left((FBG+TG)+HBA1c\times\dfrac{HBA1c\times 20}{5}+BMI\times\dfrac{FBG+TG}{150}+AST\times\dfrac{TG\times 4}{100}+FB\text{ insulin}\times(BMI-22)\right)}{S/D\text{ ratio}}$$

Where
FBG is Fasting Blood Glucose in mg/dl and normal value is 100 mg/dl
TG is Triglycerides in mg/dl normal value is <150
HBA1c is hemoglobin A1c in %, normal value is <6%
BMI is body mass index as kg/m2 where a normal value is 20 and obese begins above 25
AST is Aspartate Transferase also called SGOT in IU/liter and a normal value is 5-50
FB insulin is fasting Blood insulin concentration in nmol/liter, a normal value is 4.0

It should be noted that the 45 and 41 patients of the S/D ratio described in Examples 1-3 were included as part of the FS Index population. The reason additional subgroups were added in the Example is to get beyond the use of HBA1c as a tool for diabetes alone, and thus model all the rest of the actions of metabolic syndrome. HBA1c alone considers diabetes, which is one aspect of metabolic syndrome. On the other hand, the FS index considers all aspects of metabolic syndrome so it allows patients who have a multitude of Metabolic syndrome diseases, alone and in combination to be scored and monitored for changes caused by drug treatments. The FS index permits an assessment of the impact of drug therapy on the total metabolic syndrome profile of the patient at risk for CV events.

Results:

The database included previously published 50 patients with T2D having CV events principally myocardial infarctions, and controls of a precisely matched group of 50 T2D patients without these events. Each of these patients had at least 5 years of data. FS index values were calculated for these patients from serial laboratory and clinical data over timeframes ranging 2-10 years. In these patient populations, a normal FS index value is 20-50, and values in this range are low CV risk. Patients with two or more manifestations of Metabolic Syndrome are above 200 and the highest values are above 500, values seen only when nearly every Metabolic Syndrome component is abnormal, as might be observed in an extremely overweight T2D patient prior to RYGB surgery. It should be noted that RYGB can take the FS index of the aforementioned patient to a normal value, providing evidence that each component of metabolic syndrome responds to stimulation of the ileal brake releasing hormones. This is a highly unexpected response and therefore new evidence for a novel mechanism for control of metabolic syndrome and its complicating cardiovascular risk The outcomes of FS index calculations for the Myocardial Infarction patients vs their matched controls are shown in FIGS. 11 and 12.

Figure 11:
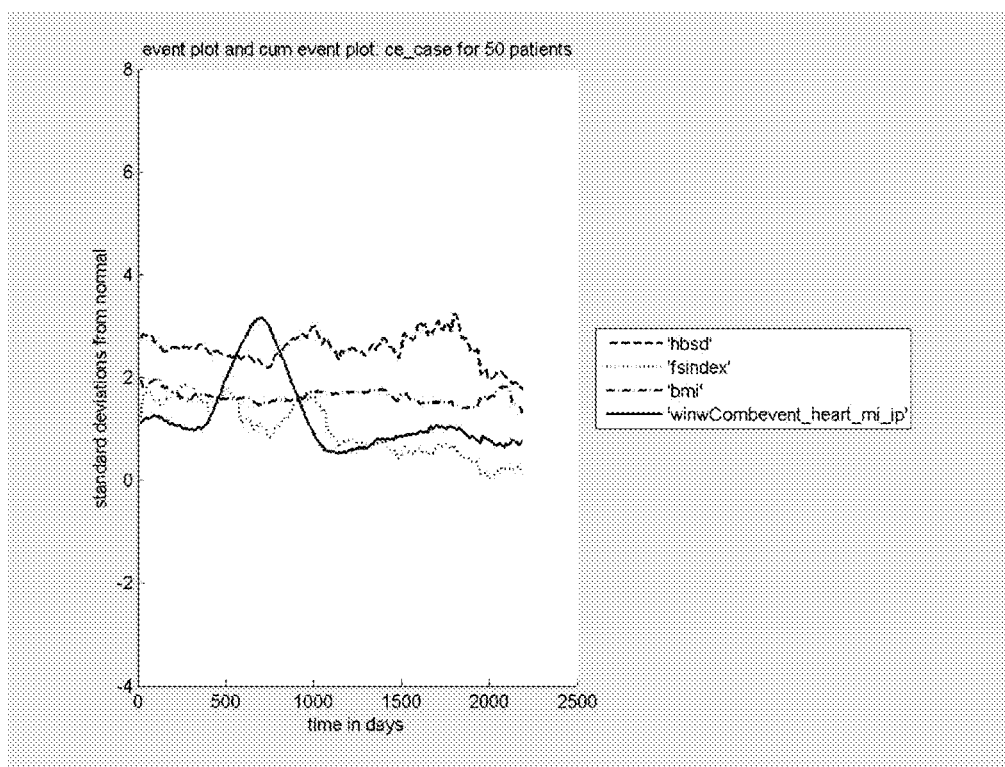
FIG. 11 provide FS index values, BMI, HBA1c/SD ratio (HBSD) in 50 T2D patients with cardiovascular events (winwCombevent_heart_mi_ip) over 5 years of monitoring.

FIG. 11. FS index values, BMI, HBA1c/SD ratio (HBSD) in 50 T2D patients with cardiovascular events (winw-Combevent_heart_mi_ip) over 5 years of monitoring Here and In the graphics that follow (FIGS. 12-18), both FS index and HBA1c to SD ratio (HBSD) are displayed as output parameters over time, along with CV risk which is denoted by output parameter shown on the graph as (+) and defined in the legend as winwCombevent_heart_MI_ip.

High FS index values preceded and therefore predicted CV events in this metabolic syndrome patient population of patients, regardless of the specific components of Metabolic Syndrome that were abnormal. Abnormal and rising FS index values predicted AMI although did not predict the time of the event. A rapid rise in the FS index over 3-6 months was a good predictor of impending CV events. When Metabolic Syndrome is studied as the equal weight of its components using the FS index, it is apparent why clinical strategies treating only one component of Metabolic Syndrome do not predict or remove all risk of CV events.

Figure 12:
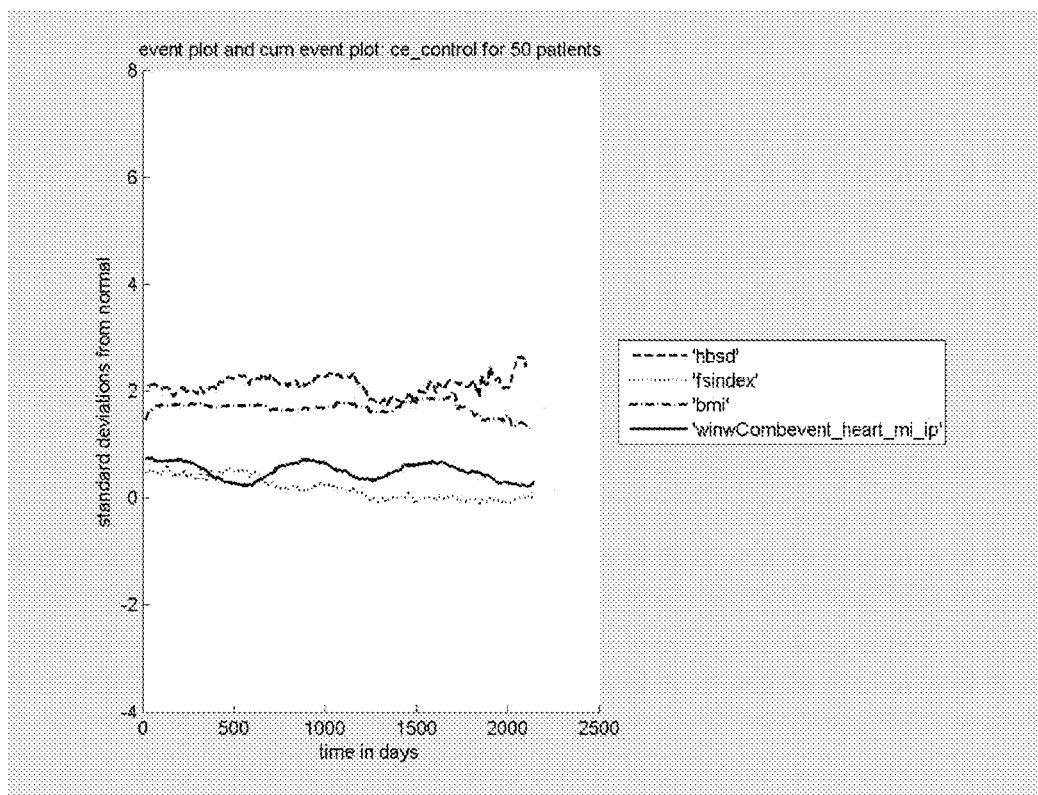
FIG. 12 shows data of patients with diabetes, but who do not have CV events. These patients differ in FS index values overall from patients with diabetes that do have CV events.
Figure 13:
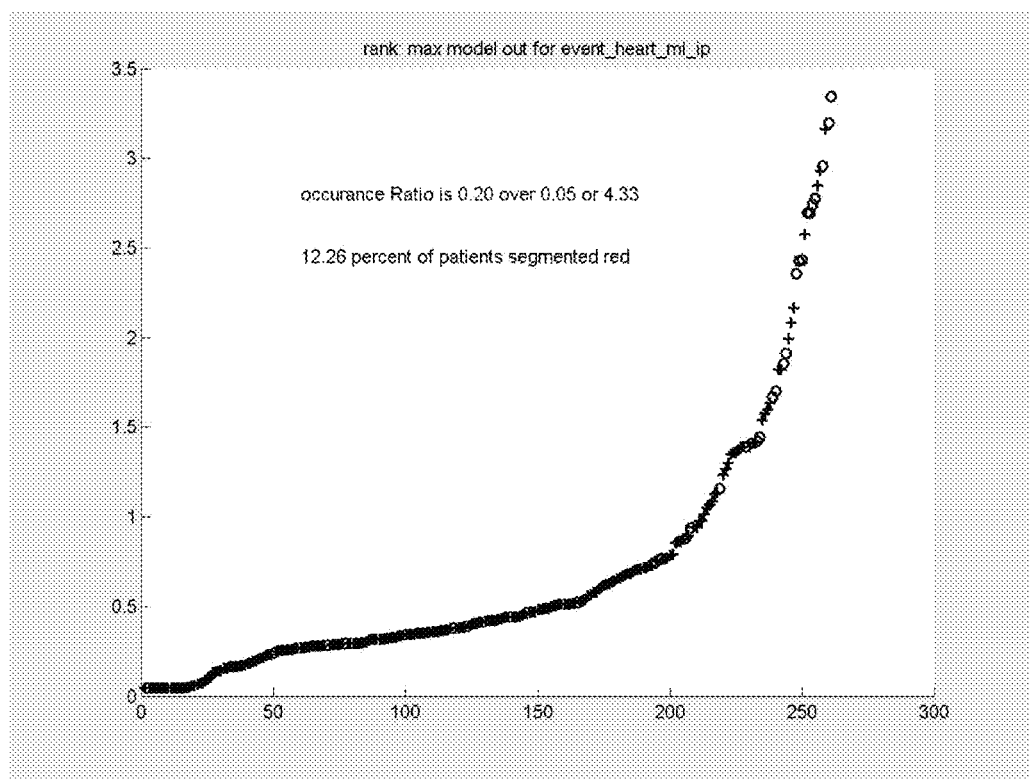
FIG. 13 displays the rank ordered CV output signal over our combined patient populations that comprise this model.

FIG. 12. Patients with diabetes, but who do not have CV events differ in FS index values overall from patients with diabetes that do have CV events.

Abnormal FS index values subsequently normalized, indicated resolution of each component of Metabolic Syndrome, raising the possibility that specific treatments of Metabolic Syndrome might halt progression or reverse Metabolic Syndrome entirely.

The index also at least and partially explains why drug therapies that improve one aspect of Metabolic Syndrome, but worsen others, may not mitigate CV risk or remove CV events in complex Metabolic Syndrome patients. The index does also show that combination therapies consisting of individual drugs, each used for one component of metabolic syndrome my lower FS index by altering each component. One advantage of using the FS index is its perspective on the importance of combination therapy and in these specific examples to follow the FS index shows the importance of certain combination therapy beneficial on the glucose supply side, such as RYGB surgery and the oral RYGB mimetic Brake.

Specific Example B

Cumulative CV Risk Signal from FS Index Elements; Illustration of Patients with MI Across the Entire Modeling Population of 250 Patients FIG. 13 displays the rank ordered CV output signal over our combined patient populations that comprise this model. There are over 250 patients in this analysis, and in FIG. 13 the patients are arranged by lowest risk near the y axis intercept to highest risk at the opposite end of the graphic display. Patients with myocardial infarctions are marked with plus (+) signs in all cases, and it is clear that the majority of these MI patients are found in patients with FS index assigned high baseline risk for CV events. This indicates that the neural net model predicts cardiovascular risk across all the diverse patients in this data analysis, itself a new finding because heretofore there has been no laboratory test predictive of the risk of cardiovascular events when many risk factors are present.

Results of the neural net model are illustrated over time for each subset of patients studied.

Specific Example C

Figure 14:
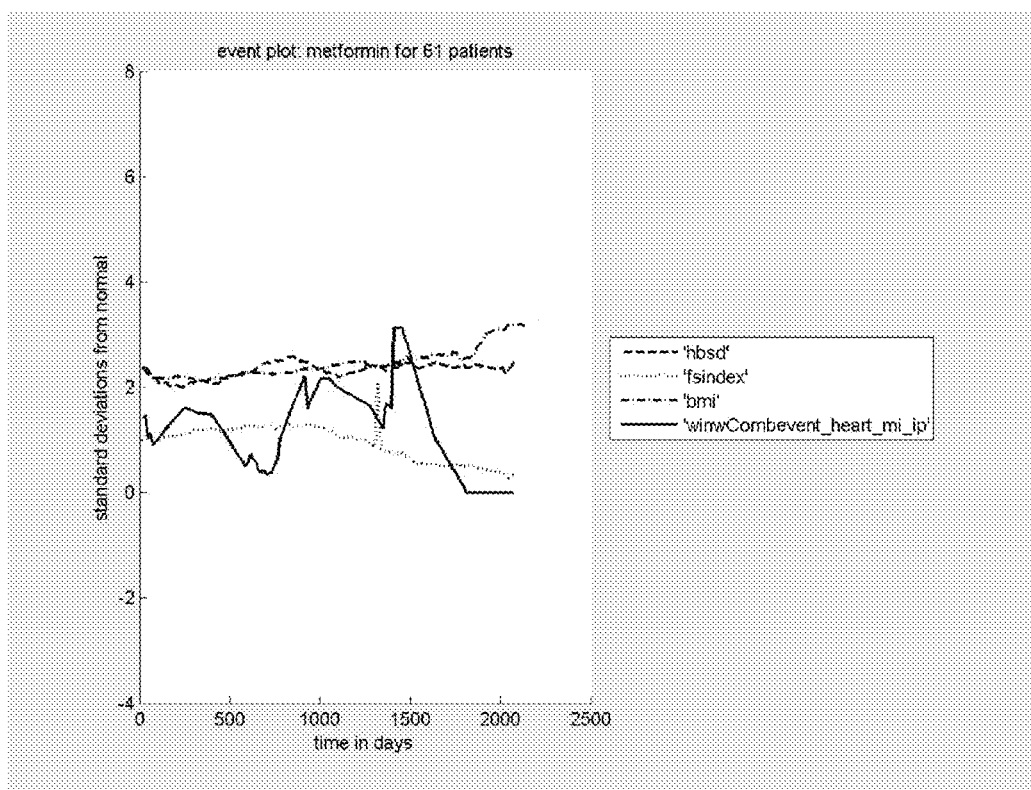
FIG. 14 illustrates the use of the neural net model applied to a T2D population of 61 patients initially treated with metformin alone, and a calculation of parameters such as FS index, HBA1c/SD ratio, and a calculated cumulative CV risk.

Illustration of Metformin Response and CV Events in 61 Patients with T2D Treated with Metformin FIG. 14 illustrates our use of the neural net model applied to a T2D population of 61 patients initially treated with metformin alone, and a calculation of parameters such as FS index, HBA1c/SD ratio, and a calculated cumulative CV risk. Clearly, CV risk is relatively low with metformin, but the T2D slowly progresses and as shown in FIG. 14 the patients all slowly worsen. Their FS index rises, their HBSD rises, they gain weight and there is a progressive increase in FS index indicating a slow progression of CV risk. The progressive loss of diabetic control leads to a quantified need for added therapy to the metformin regimen. In extreme cases the best approach may be to apply RYGB surgery in an effort to control the underlying metabolic syndrome of the patient who is rapidly gaining weight with their T2D. Thus the FS index can point to a time to add anti-diabetic drugs beneficial to the treatment of the underlying metabolic syndrome. In one particularly beneficial example, patients with rising FS index on metformin alone can be given Brake therapy, and when this combination is used their FS index will become normal. We have used this combination treatment approach guided by FS index and have shown its benefit, an observation that justifies initial use of Metformin combined with Brake early in diabetes as metformin alone does not control the T2D or the underlying metabolic syndrome.

As shown in FIG. 14, the usual pattern of FS index is flat or slowly rising in patients given metformin alone. This indicates that metformin is not a treatment alone for metabolic syndrome.

Specific Example D

Figure 15:
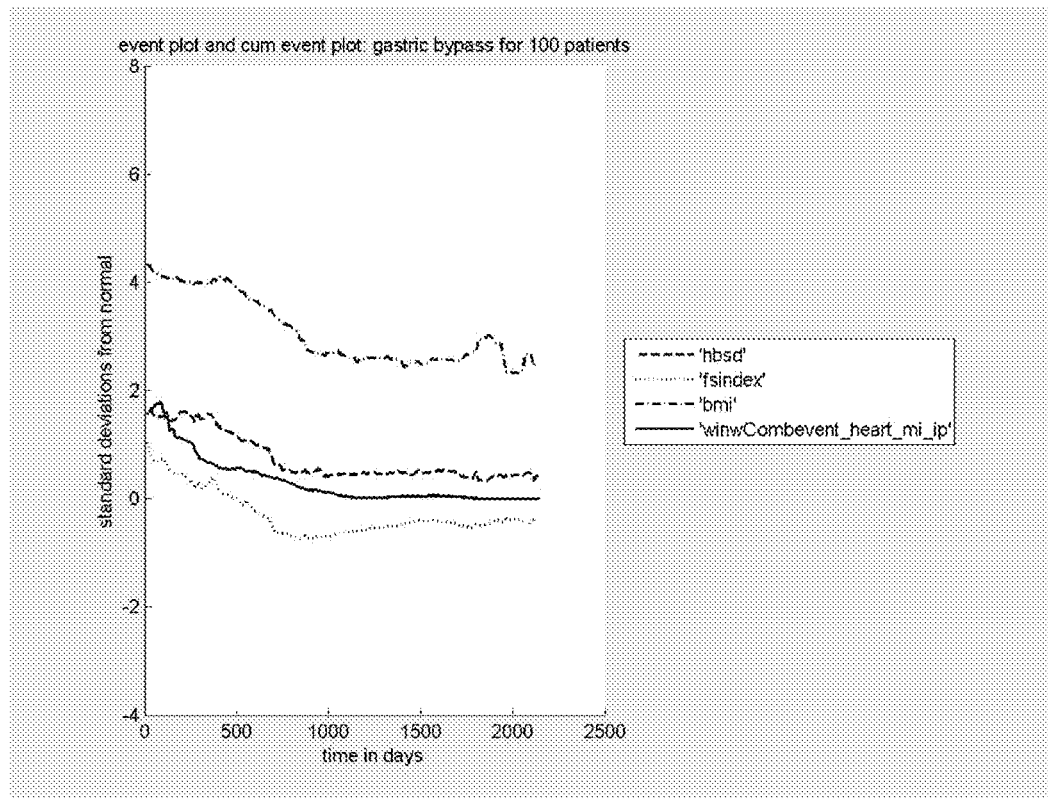
FIG. 15 shows the improvement in FS index in 100 RYGB surgery patients, with almost a complete lowering of CV risk to normal by 6-12 months after the RYGB surgery procedure.

Illustration of Model Output for RYGB Surgery in 100 Patients with Surgery to Control Obesity Alone or Concomitantly with T2D In contrast to metformin and most other approaches to T2D where there is little change in FS index, RYGB surgery greatly improves FS index as illustrated in FIG. 15. Furthermore, FS index improves rapidly as metabolic syndrome improves and glucose supply declines. FIG. 15 shows this improvement in 100 RYGB surgery patients, with almost a complete lowering of CV risk to normal by 6-12 months after the RYGB surgery procedure. Many of said patients remain on metformin but they are usually no longer requiring insulin for their T2D.

Specific Example E

Figure 16:
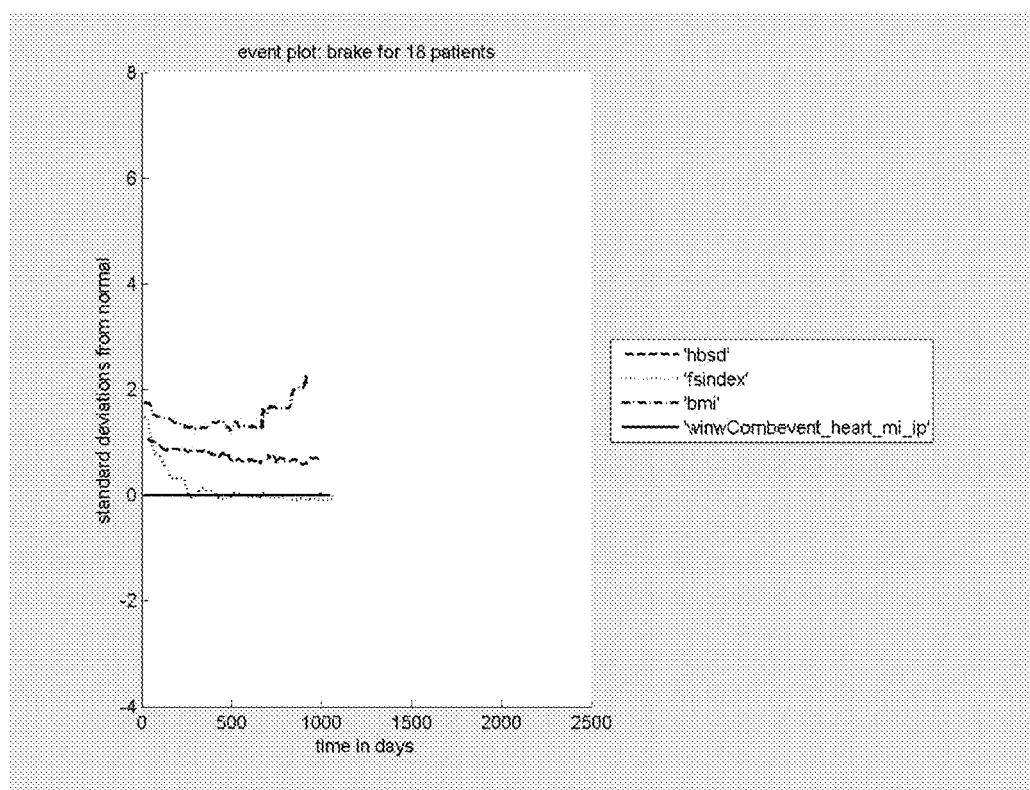
FIG. 16 shows the improvement in FS index and other parameters of metabolic syndrome for 18 patients treated with Brake, which is an oral mimetic of the hormonal effects of bariatric surgery

Modeling Results for 18 Patients Treated with Brake for Obesity, Hyperlipidemia, T2D or NAFLD, with Illustrated Method for Study of these Patients in Real Time In FIG. 16, the improvement in FS index and other parameters of metabolic syndrome is shown for 18 patients treated with Brake The results of treatment displayed in FIG. 16 show that there is about the same lowering of FS index from Brake as RYGB, an observation that is predictive of both of these interventions lowering CV risk in patients.

The data from these patients shows a broad spectrum effect of Brake therapy, in that Brake controls the patient's hyperglycemia and HBA1c, controls elevated Triglycerides, controls elevated blood pressure, controls NAFLD and lowers all of the elevated hepatic enzymes, and rapidly lowers FB insulin and glucose, thus lowering insulin resistance. The combination of all of these effects from Brake is predicted by FS index and in fact results in a normal FS index value in each patient by 3-4 months of therapy.

In this manner an expanded benefit can be defined for either RYGB or the oral mimetic of RYGB called Brake.

Specific Example F

Figure 17:
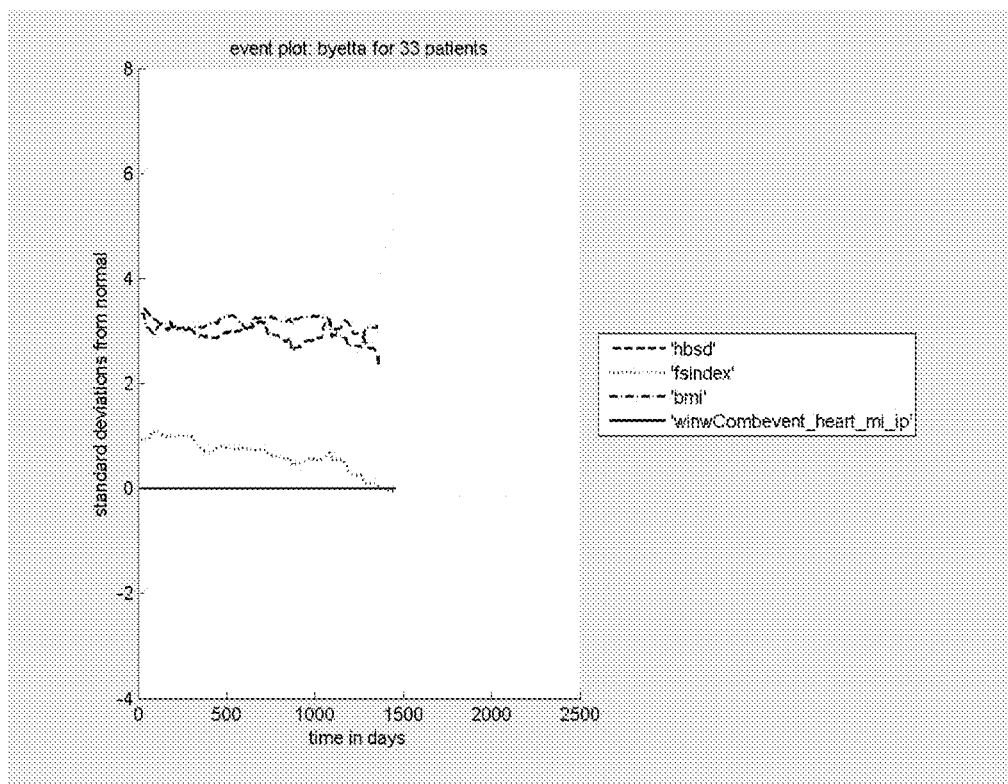
FIG. 17 shows FS index calculations to define the response to exenatide, trade-named Byetta. The response to this incretin hormone drug (a form of GLP-1 therapy) was a progressive lowering of FS index and a small change in BMI and HBSD.

Modeling Results for 33 Patients Treated with Exenatide (Byetta) for T2D, with Illustrated Method for Treatment of these Patients In FIG. 17, we employed FS index calculations to define the response to exenatide, trade-named Byetta. As shown in FIG. 17, the response to this incretin hormone drug (a form of GLP-1 therapy) was a progressive lowering of FS index and a small change in BMI and HBSD.

The FS index calculation results displayed in FIG. 17 indicate beneficial response to the diabetes component of metabolic syndrome, although there is not a major impact of Byetta on any other component of metabolic syndrome beyond obesity. Specifically, lipid abnormalities do not resolve and NAFLD abnormalities do not resolve. None of these biomarker responses of FS index components are linked specifically to GLP-1 responses alone, so this narrow band of effect of Byetta alone on only the glucose supply side of T2D is typically dealt with by adding additional pharmaceutical treatments to patients in need. Common additions to Byetta include a statin drug for lipid control, Omega3 products for lowering of Triglycerides, an ACE inhibitor to control blood pressure. There is no FDA approved treatment for NAFLD. Thus Brake or RYGB have roles in the treatment of NAFLD. However, the condition remains untreated in most patients given typical treatments for type 2 diabetes. Affecting these laboratory biomarkers would be reflected in the FS index as a beneficial lowering of CV risk, and would show benefit of adding Brake as a lowering of CV risk overall.

Patients given Byetta for treatment of T2D may be given oral Brake to provide control of NAFLD, elevated triglycerides, blood pressure, insulin resistance, and weight. It should be evident to those skilled in the art that any other GLP-1 injectable drugs employed in patients with T2D would also benefit from adding Brake therapy, specific examples would be stated to include but not be limited to Liraglutide (Victoza).

Specific Example G

Figure 18:
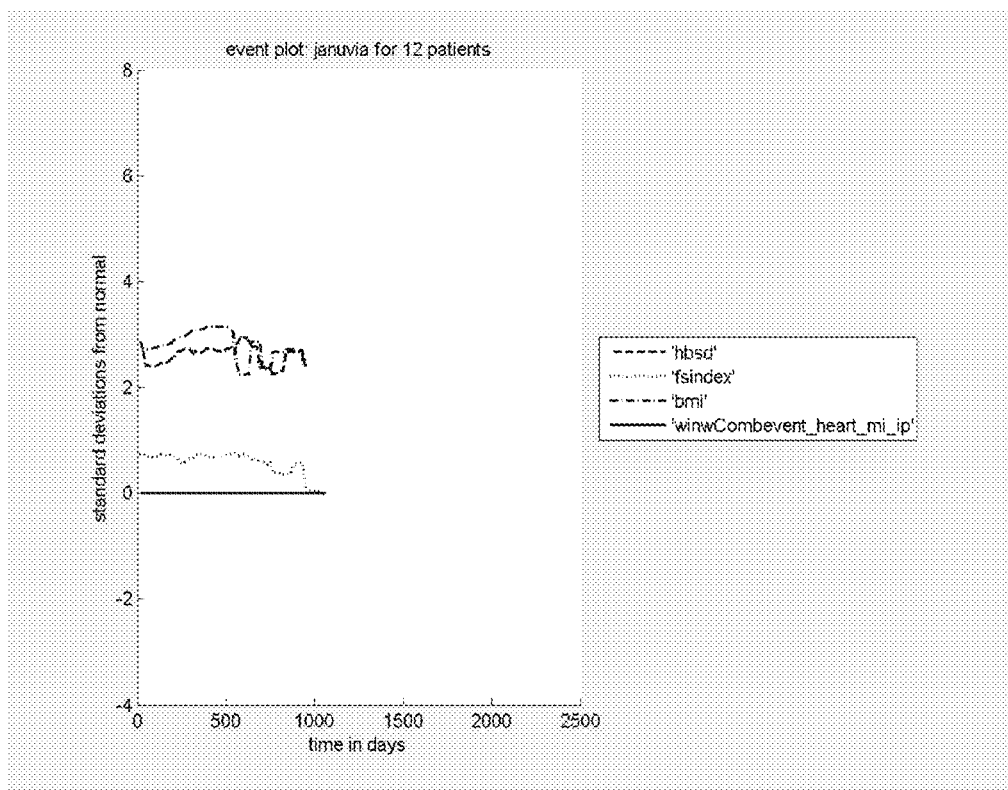
FIG. 18 illustrates the FS index response to treatment with sitagliptin, aka Januvia, in 12 T2D patients treated therewith and with the data used to analyzed changes in FS index produced by the treatment.

Modeling Results for 12 Patients Treated with Sitagliptin (Januvia) for T2D, with Illustrated Method for Treatment of these Patients FIG. 18 illustrates the FS index response to treatment with sitagliptin, aka Januvia, in 12 T2D patients treated therewith and with the data used to analyzed changes in FS index produced by the treatment.

The FS index calculation results displayed in FIG. 18 indicate beneficial response to the diabetes component of metabolic syndrome, although there is not a major impact of Sitagliptin (Januvia) on any other component of metabolic syndrome beyond hyperglycemia. Specifically, weight slowly increases or stays the same, lipid abnormalities do not resolve and NAFLD abnormalities do not resolve. None of these biomarker responses of FS index components are linked specifically to GLP-1 responses alone, so this narrow band of effect of Januvia alone on only the glucose supply side of T2D is typically dealt with by adding additional pharmaceutical treatments to patients in need. Common additions to Januvia include a statin drug for lipid control, Omega3 products for lowering of Triglycerides, an ACE inhibitor to control blood pressure. There is no FDA approved treatment for NAFLD. The other treatments do not affect the condition with the exception of Brake or RYGB, so this part of the condition remains untreated in most patients.

We have treated Patients given Januvia and similar drugs for treatment of T2D at the point where there is stable response but not resolution of T2D, adding oral Brake to the Januvia or other DPP_IV inhibitor to provide control of HBA1c, NAFLD, elevated triglycerides, blood pressure, insulin resistance, and weight. Affecting these laboratory biomarkers would be reflected in the FS index as a beneficial lowering of CV risk, and would show benefit of adding Brake as a lowering of CV risk overall. In at least one of these patients additional decline in HBA1c was shown and the FS index was normal during treatment. It should be evident to those skilled in the art that any other DPP-IV inhibitor employed in patients with T2D would also benefit from adding Brake therapy, specific examples would be stated to include but not be limited to saxagliptin (onglyza) Linagliptin (Tradgenta) alogliptin (if approved by FDA) and others.

Specific Example H

The Use of FS Index in Selection of Patients in Need of Treatment for Metabolic Syndrome and a Means of Defining the Response to Treatment of Said Metabolic Syndrome The final model for implementing this metabolic syndrome CV progression model is an application for individual patients on a computer such as a web-enabled cellphone, an I-pad or a Windows 8 tablet. The application will record weight, food intake, calories from specific type of food, and exercise. From these, each patient's insulin output and CV risk is calculated daily and the metabolic syndrome progression is linked to food and lifestyle. Once the links are established for each patient, the application puts the patient onto an optimization plan that should minimize disease and maximize life expectancy. An example of a weight reduction tracked on said application for one patient is FIG. 19

Figure 19:
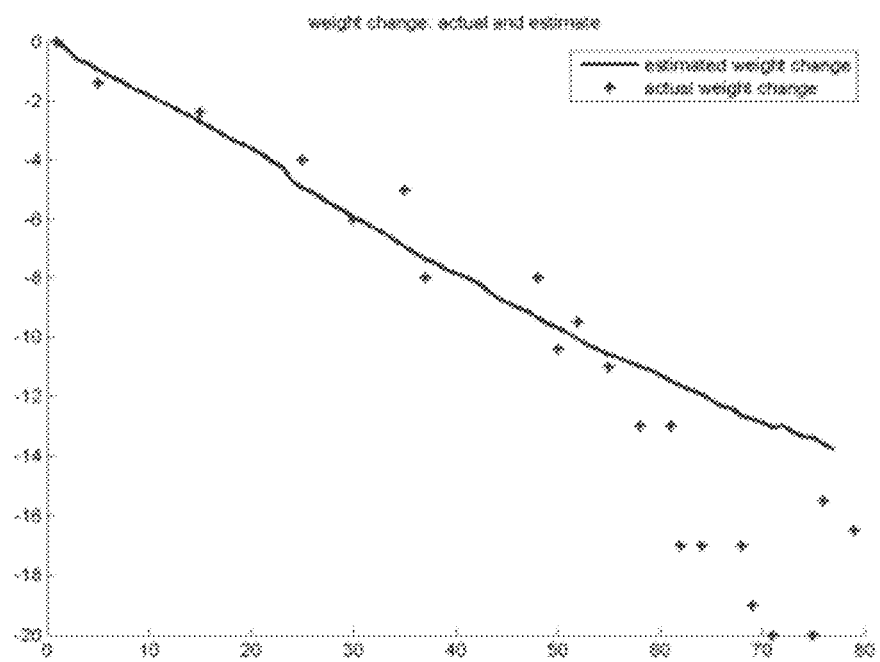
FIG. 19 shows an example of a weight reduction tracked on an I-pad application for one patient over a time of 80 days. This subject, a 55 year old female, was on a weight reduction program only and did not have FS index abnormalities beyond a mild form of dietary associated metabolic syndrome.

Weight is plotted in FIG. 19 as pounds decreased from baseline over a time of 80 days when monitored using said I-pad application. This subject, a 55 year old female, was on a weight reduction program only and did not have abnormalities beyond a mild form of dietary associated metabolic syndrome.

Discussion of Modeling Results

Overall, the FS (Fayad/Schentag) index, which is composed of mostly readily available laboratory and clinical measures, appears to be an effective means of describing progression or amelioration of the end organ manifestations of metabolic syndromes in routine practice, including the changes that occur as a result of organ or system regeneration after RYGB surgery or treatment with Brake. Its use in aggregate or use of its principle components separately are hereby designated as a primary means of demonstrating direction of metabolic syndrome manifestations (improved or worsening) and the impact of therapeutic interventions designed to improve metabolic syndrome via stop and repair mechanisms of action. To avoid doubt, said therapeutic interventions include both RYGB and combinations of pharmaceuticals wherein the composition of said pharmaceuticals includes Brake or its specific components in a dosage range between 7,500 mg and 20,000 mg.

Clinical proof of the utility of the synergistic combination of these therapies for other metabolic syndrome diseases, such as Alzheimer's disease, would necessitate the adoption of biomarkers of metabolic syndrome progression such as the FS index, which is an overall biomarker profile that can point to regenerative processes that respond to RYGB or Brake. Added to the metabolic syndrome biomarker profile of the FS index would be a biomarker profile of Alzheimer's disease progression. This latter progression profile would focus on cognition, genomics where applicable, and imaging where applicable to loss of brain tissue and neuronal mass. To the extent that these biomarkers are improved by donepezil, those effects carry forward. To the extent that the observed improvement is tied to effects beyond those of donepezil, the conclusion would be Brake associated recovery or regeneration of functioning neurons.

References for Example 4

1. Adams R J, Appleton S, Wilson D H, Taylor A W, Dal Grande E, Chittleborough C, et al. Population comparison of two clinical approaches to the metabolic syndrome: implications of the new International Diabetes Federation consensus definition. Diabetes Care. 2005; 28(11):2777-9.
2. Aguilar-Salinas Calif., Rojas R, Gomez-Perez F J, Valles V, Rios-Torres J M, Franco A, et al. Analysis of the agreement between the World Health Organization criteria and the National Cholesterol Education Program-III definition of the metabolic syndrome: results from a population-based survey. Diabetes Care. 2003; 26(5):1635.
3. Alberti K G, Zimmet P, Shaw J. The metabolic syndrome—a new worldwide definition. Lancet. 2005; 366(9491):1059-62.
4. Assmann G, Guerra R, Fox G, Cullen P, Schulte H, Willett D, et al. Harmonizing the definition of the metabolic syndrome: comparison of the criteria of the Adult Treatment Panel III and the International Diabetes Federation in United States American and European populations. Am J Cardiol. 2007; 99(4):541-8.
5. Chen H J, Pan W H. Probable blind spot in the International Diabetes Federation definition of metabolic syndrome. Obesity (Silver Spring). 2007; 15(5):1096-100.
6. de Simone G, Devereux R B, Chinali M, Best L G, Lee E T, Galloway J M, et al. Prognostic impact of metabolic syndrome by different definitions in a population with high prevalence of obesity and diabetes: the Strong Heart Study. Diabetes Care. 2007; 30(7):1851-6.
7. Demacker P N. The metabolic syndrome: definition, pathogenesis and therapy. Eur J Clin Invest. 2007; 37(2):85-9.
8. Grundy S M, Brewer H B, Jr., Cleeman J I, Smith S C, Jr., Lenfant C. Definition of metabolic syndrome: Report of the National Heart, Lung, and Blood Institute/American Heart Association conference on scientific issues related to definition. Circulation. 2004; 109(3):433-8.
9. Heng D, Ma S, Lee J J, Tai B C, Mak K H, Hughes K, et al. Modification of the NCEP ATP III definitions of the metabolic syndrome for use in Asians identifies individuals at risk of ischemic heart disease. Atherosclerosis. 2006; 186(2):367-73.
10. Jorgensen M E, Borch-Johnsen K. The metabolic syndrome—is one global definition possible? Diabet Med. 2004; 21(10):1064-5.
11. Lorenzo C, Williams K, Hunt K J, Haffner S M. The National Cholesterol Education Program—Adult Treatment Panel III, International Diabetes Federation, and World Health Organization definitions of the metabolic syndrome as predictors of incident cardiovascular disease and diabetes. Diabetes Care. 2007; 30(1):8-13.
12. Onat A, Uyarel H, Hergenc G, Karabulut A, Albayrak S, Can G. Determinants and definition of abdominal obesity as related to risk of diabetes, metabolic syndrome and coronary disease in Turkish men: a prospective cohort study. Atherosclerosis. 2007; 191(1):182-90.
13. Sandhofer A, Iglseder B, Paulweber B, Ebenbichler C F, Patsch J R. Comparison of different definitions of the metabolic syndrome. Eur J Clin Invest. 2007; 37(2):109-16.
14. Zimmet P, Magliano D, Matsuzawa Y, Alberti G, Shaw J. The metabolic syndrome: a global public health problem and a new definition. J Atheroscler Thromb. 2005; 12(6):295-300.
15. Monte S V, Schentag J J, Adelman M H, Paladino J A. Characterization of cardiovascular outcomes in a type 2 diabetes glucose supply and insulin demand model. J Diabetes Sci Technol. 2010; 4(2):382-90.
16. Monte S V, Schentag J J, Adelman M H, Paladino J A. Glucose supply and insulin demand dynamics of antidiabetic agents. J Diabetes Sci Technol. 2010; 4(2):365-81.
17. Schauer P R, Kashyap S R, Wolski K, Brethauer S A, Kirwan J P, Pothier C E, et al. Bariatric surgery versus intensive medical therapy in obese patients with diabetes. N Engl J Med. 2012; 366(17):1567-76.

The invention claimed is:

1. A method for determining cardiovascular risk for an individual suspected of having, at risk for, or diagnosed with a Metabolic Syndrome, the method comprising:
   a) obtaining from the individual one or more biological parameters, wherein the biological parameters are selected from the group consisting of fasting Blood Glucose, Triglycerides, Hemoglobin A1c, body mass index, Aspartate Transferase and fasting Blood Insulin, and from the biological parameters:
   b) determining a Fayad/Schentag (FS) index, wherein the FS index is calculated as:

$$\frac{0.11\left((FBG+TG)+HBA1c\times\frac{HBA1c\times 20}{5}+BMI\times\frac{FBG+TG}{150}+AST\times\frac{TG\times 4}{100}+FB\text{ insulin}\times(BMI-22)\right)}{S/D \text{ ratio}}$$

wherein the FBG is Fasting Blood Glucose in mg/dl; the TG is Triglycerides in mg/dl; the HBA1c is hemoglobin A1c in %; the BMI is body mass index in kg/m$^2$; AST is Aspartate Transferase in IU/liter; FB insulin is fasting Blood insulin concentration in nmol/liter; and the S/D ratio (SD) is a ratio of Glucose Supply Index (S) to Insulin Demand Index (D) calculated as follows:
(S) calculated as follows:

1+[aggregate of carbohydrate exposure(CE)+hepatic glucose uptake(HGU)+hepatic gluconeogenesis (GNG) and +insulin resistance(IR)], and (D) calculated as follows:

1+[aggregate of peripheral glucose uptake(PGU)+ peripheral insulin exposure(PIE)];

c) assign the FS index determined in b) to the individual, wherein the FS index is a value of greater than 60 and is thereby indicative that the individual is in need of therapy for Metabolic Syndrome or at risk for at least one cardiovascular complication associated with Metabolic Syndrome, the method further comprising:

d). administering to the individual a drug, wherein the drug is used to treat or resolve Metabolic Syndrome and is a formulation comprising pH encapsulated glucose, wherein said glucose from said pH encapsulated glucose formulation is targeted for release in the ileum of said individual, wherein conditions for release of said glucose from said pH encapsulated glucose formulation are a pH at or above a pH of 7.0.

2. The method of claim 1, wherein the individual has been diagnosed with Metabolic Syndrome, wherein the individual is being treated for Metabolic Syndrome with at least one first drug known to be active against at least one component of the FS index, wherein the at least one first drug with which the individual is being treated is not the pH encapsulated glucose, and wherein the FS index value obtained in step b) is a first FS index value, the method further comprising prior to performing step d) repeating steps a), b) and c) after a period of time during which the individual continues treatment with the at least one first drug to provide a second FS index value, wherein a higher second FS index value relative to the first FS index value indicates that the individual is in need of a change in dosing of the at least one first drug, or a change to a different drug, or is a candidate for bariatric surgery, the method further comprising performing step d).

3. The method of claim 2, wherein each FS index value is determined using a microprocessor.

4. The method of claim 2, wherein the SD ratio is determined using a programmable spreadsheet.

5. The method of claim 1, wherein at the time the determining the FS index value of greater than 60 is performed, the individual is not being treated with a diabetes drug, and wherein the SD ratio is 1.

6. The method of claim 1, wherein the FS index value is determined using a microprocessor.

7. The method of claim 1, wherein the SD ratio is determined using a programmable spreadsheet.

8. The method of claim 1, wherein severity of one or more of the cardiovascular complications associated with Metabolic Syndrome is reduced subsequent to the administration of the formulation comprising pH-encapsulated glucose.

9. The method of claim 8, wherein the glucose in said pH-encapsulated glucose formulation ranges from 5 grams to 20 grams.

10. The method of claim 1, wherein the formulation comprising pH encapsulated glucose is administered in combination with an additional agent selected from the group consisting of anti-diabetes drugs, insulin, statin drugs, hormones, GLP-1 drugs, lipids, proteins, amino-acids, other sugars or carbohydrates, Metformin, Sitagliptin, and combinations thereof.

* * * * *